United States Patent
Fuji et al.

(10) Patent No.: US 9,342,179 B2
(45) Date of Patent: May 17, 2016

(54) STRAIN SENSING ELEMENT, PRESSURE SENSOR, MICROPHONE, BLOOD PRESSURE SENSOR, AND TOUCH PANEL

(71) Applicant: KABUSHIKI KAISHA TOSHIBA, Tokyo (JP)

(72) Inventors: Yoshihiko Fuji, Kawasaki Kanagawa (JP); Hideaki Fukuzawa, Kawasaki Kanagawa (JP); Tomohiko Nagata, Yokohama Kanagawa (JP); Akio Hori, Kawasaki Kanagawa (JP); Yoshihiro Higashi, Komatsu Ishikawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 14/471,226

(22) Filed: Aug. 28, 2014

(65) Prior Publication Data
US 2015/0082917 A1    Mar. 26, 2015

(30) Foreign Application Priority Data
Sep. 20, 2013   (JP) .................................. 2013-196059

(51) Int. Cl.
*G01L 1/12*   (2006.01)
*G06F 3/041*  (2006.01)
(Continued)

(52) U.S. Cl.
CPC .......... *G06F 3/0414* (2013.01); *A61B 5/02141* (2013.01); *G01L 1/125* (2013.01);
(Continued)

(58) Field of Classification Search
CPC .... G01L 9/16; G01L 1/12; A61B 2562/0247; G06F 3/0414
USPC .............................................. 73/862.69, 779
See application file for complete search history.

(56) References Cited

U.S. PATENT DOCUMENTS

| 5,712,751 A * | 1/1998 | Yoda | ..................... B82Y 10/00 360/324.12 |
| 2004/0000415 A1 | 1/2004 | Rizzo et al. | |

(Continued)

FOREIGN PATENT DOCUMENTS

| CN | 1666585 A1 | 9/2005 |
| JP | 05-099775 | 4/1993 |

(Continued)

OTHER PUBLICATIONS

M. Löhndorf et al., "Highly sensitibe strain sensor based on magnetic tunneling junctions", *Applied Physics Letters*, vol. 81, No. 2, pp. 313-315, (2002).

(Continued)

*Primary Examiner* — Max Noori
(74) *Attorney, Agent, or Firm* — Finnegan, Henderson, Farabow, Garrett & Dunner, LLP

(57) ABSTRACT

According to one embodiment, a strain sensing element includes a film unit, and a sensing unit. The film unit has a film surface and is capable of being deformed. The sensing unit includes a first sensing element and a second sensing element. The first sensing element is provided between a part of the film unit and the second sensing element. The first sensing element includes a first magnetic layer having a changeable magnetization with a deformation of the film unit, a second magnetic layer provided apart from the first magnetic layer, and a first spacer layer provided between the first and second magnetic layers. The second sensing element includes a third magnetic layer having a changeable magnetization with the deformation of the film unit, a fourth magnetic layer provided apart from the third magnetic layer, and a second spacer layer provided between the third and fourth magnetic layers.

18 Claims, 29 Drawing Sheets

(51) Int. Cl.
   *G01L 9/16* (2006.01)
   *A61B 5/021* (2006.01)
   *G01L 9/00* (2006.01)
   *H04R 19/00* (2006.01)
   *H04R 19/04* (2006.01)
   *H04R 31/00* (2006.01)
   *A61B 5/00* (2006.01)

(52) U.S. Cl.
   CPC ............. *G01L 9/0041* (2013.01); *G01L 9/16* (2013.01); *H04R 19/005* (2013.01); *H04R 19/04* (2013.01); *H04R 31/00* (2013.01); *A61B 5/6824* (2013.01); *A61B 2562/0247* (2013.01)

(56) References Cited

U.S. PATENT DOCUMENTS

| | | | | |
|---|---|---|---|---|
| 2006/0023376 A1* | 2/2006 | Gill | ............ | G11B 5/3903 360/324.12 |
| 2006/0048304 A1* | 3/2006 | Boyd | ............ | A47C 21/048 5/738 |
| 2007/0186666 A1 | 8/2007 | Ruehrig et al. | | |
| 2011/0295128 A1 | 12/2011 | Yuasa et al. | | |
| 2011/0307214 A1 | 12/2011 | Saitou et al. | | |
| 2012/0079887 A1 | 4/2012 | Giddings et al. | | |
| 2012/0245477 A1 | 9/2012 | Giddings et al. | | |
| 2013/0076687 A1 | 3/2013 | Giddings et al. | | |
| 2013/0079648 A1 | 3/2013 | Fukuzawa et al. | | |
| 2013/0170669 A1 | 7/2013 | Fukuzawa et al. | | |
| 2013/0255069 A1 | 10/2013 | Higashi et al. | | |
| 2013/0255393 A1 | 10/2013 | Fukuzawa et al. | | |
| 2014/0069200 A1 | 3/2014 | Yuasa et al. | | |
| 2014/0090486 A1 | 4/2014 | Fuji et al. | | |
| 2014/0137658 A1 | 5/2014 | Higashi et al. | | |
| 2014/0137668 A1 | 5/2014 | Fukuzawa et al. | | |

FOREIGN PATENT DOCUMENTS

| | | |
|---|---|---|
| JP | 2002-148132 | 5/2002 |
| JP | 2007-180201 | 7/2007 |
| JP | 2011-244936 | 12/2011 |
| JP | 2012-026991 | 2/2012 |
| JP | 2012-078186 | 4/2012 |
| JP | 2012-176294 | 9/2012 |
| JP | 2012-204479 | 10/2012 |
| JP | 2013-070732 | 4/2013 |
| JP | 2013-072712 | 4/2013 |
| JP | 2013-073374 | 4/2013 |
| JP | 2013-165977 | 8/2013 |
| JP | 2013-205255 | 10/2013 |
| JP | 2013-205403 | 10/2013 |
| JP | 2014-052360 | 3/2014 |
| JP | 2014-074606 | 4/2014 |
| JP | 2014-102171 | 6/2014 |
| JP | 2014-103539 | 6/2014 |

OTHER PUBLICATIONS

D. Meyners et al., "Pressure sensor based on magnetic tunnel junctions", *Journal of Applied Physics 105*, pp. 07C914-1-07C914-03, (2009).

Office Action issued by the Taiwanese Intellectual Property Office on Jun. 11, 2015, for Taiwanese Patent Application No. 103129907, and English-language translation thereof.

Decision of Rejection issued by the Taiwanese Intellectual Property Office on Sep. 23, 2015, for Taiwanese Patent Application No. 103129907, and English-language translation thereof.

* cited by examiner

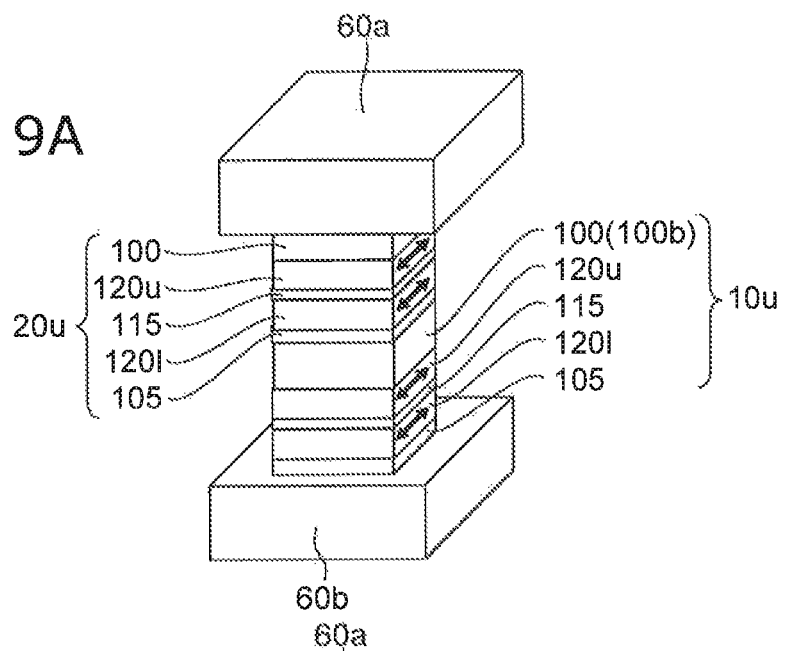
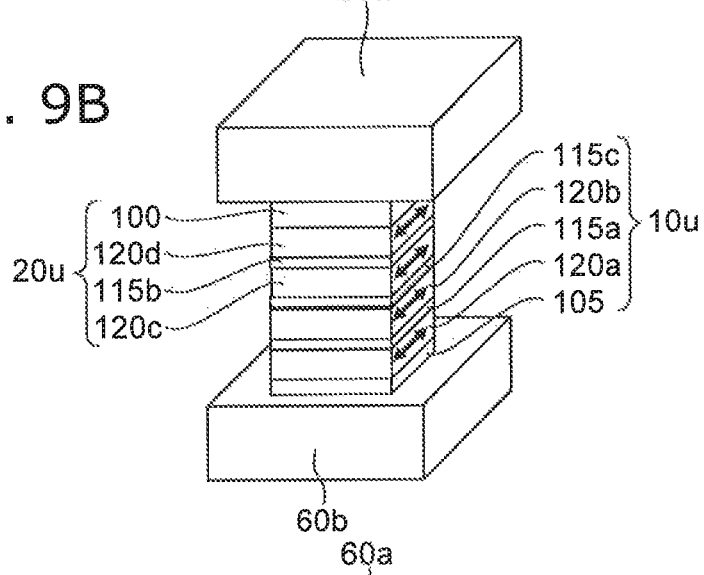
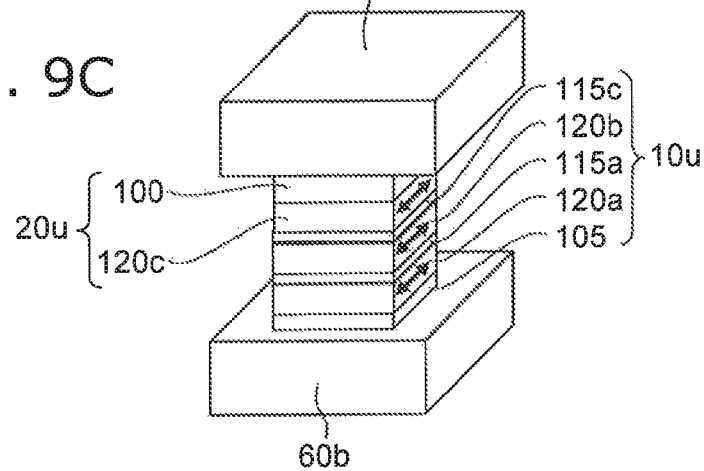

STRAIN SENSING ELEMENT, PRESSURE SENSOR, MICROPHONE, BLOOD PRESSURE SENSOR, AND TOUCH PANEL

CROSS-REFERENCE TO RELATED APPLICATIONS

This application is based upon and claims the benefit of priority from Japanese Patent Application No. 2013-196059, filed on Sep. 20, 2013; the entire contents of which are incorporated herein by reference.

FIELD

Embodiments described herein relate generally to a strain sensing element, a pressure sensor, a microphone, a blood pressure sensor, and a touch panel.

BACKGROUND

For pressure sensors using MEMS (micro electro mechanical systems) technology, there are a piezoresistance change type and an electrostatic capacitance type, for example. On the other hand, a pressure sensor using spin technology is proposed. In the pressure sensor using spin-electronics technology, a resistance change in accordance with strain is sensed. A high-sensitivity pressure sensor using spin-electronics technology is desired.

BRIEF DESCRIPTION OF THE DRAWINGS

FIG. 9A to FIG. 9C are schematic perspective views showing parts of strain sensing elements according to the embodiment.

DETAILED DESCRIPTION

Figure 1A:
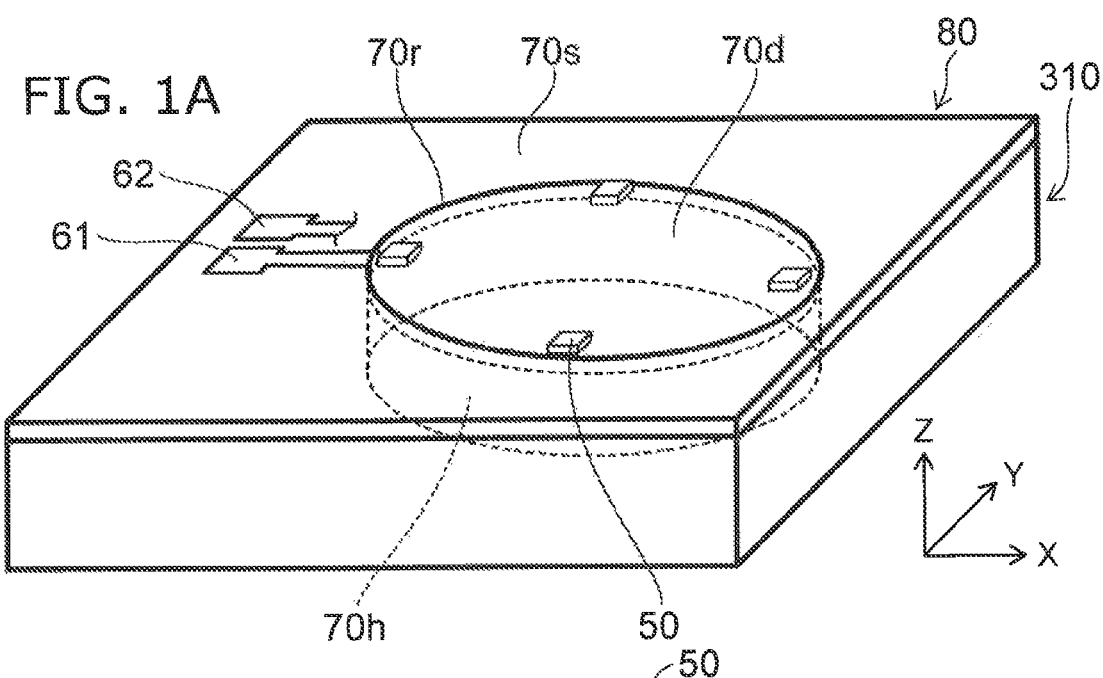
FIG. 1 A to FIG. 1F are schematic views showing a strain sensing element according to a first embodiment.

According to one embodiment, a strain sensing element includes a film unit, and a sensing unit. The film unit has a film surface and is deformable. The sensing unit includes a first sensing element and a second sensing element. The first sensing element is provided between a part of the film unit and the second sensing element. The first sensing element includes a first magnetic layer, a second magnetic layer provided apart from the first magnetic layer in a first direction crossing the film surface, and a first spacer layer provided between the first magnetic layer and the second magnetic layer. A magnetization of the first magnetic layer is configured to change in accordance with a deformation of the film unit. The second sensing element includes a third magnetic layer, a fourth magnetic layer provided apart from the third magnetic layer in the first direction, and a second spacer layer provided between the third magnetic layer and the fourth magnetic layer. A magnetization of the third magnetic layer is configured to change in accordance with the deformation of the film unit.

According to one embodiment, a pressure sensor includes a strain sensing element, and a support supporting the film unit. The strain sensing element includes a film unit, and a sensing unit. The film unit has a film surface and is deformable. The sensing unit includes a first sensing element and a second sensing element. The first sensing element is provided between a part of the film unit and the second sensing element. The first sensing element includes a first magnetic layer, a second magnetic layer provided apart from the first magnetic layer in a first direction crossing the film surface, and a first spacer layer provided between the first magnetic layer and the second magnetic layer. A magnetization of the first magnetic layer is configured to change in accordance with a deformation of the film unit. The second sensing element includes a third magnetic layer, a fourth magnetic layer provided apart from the third magnetic layer in the first direction, and a second spacer layer provided between the third magnetic layer and the fourth magnetic layer. A magnetization of the third magnetic layer is configured to change in accordance with the deformation of the film unit.

According to one embodiment, a microphone includes a pressure sensor. The pressure sensor includes a strain sensing element, and a support supporting the film unit. The strain sensing element includes a film unit, and a sensing unit. The film unit has a film surface and is deformable. The sensing unit includes a first sensing element and a second sensing element. The first sensing element is provided between a part of the film unit and the second sensing element. The first sensing element includes a first magnetic layer, a second magnetic layer provided apart from the first magnetic layer in a first direction crossing the film surface, and a first spacer layer provided between the first magnetic layer and the second magnetic layer. A magnetization of the first magnetic layer is configured to change in accordance with a deformation of the film unit. The second sensing element includes a third magnetic layer, a fourth magnetic layer provided apart from the third magnetic layer in the first direction, and a second spacer layer provided between the third magnetic layer and the fourth magnetic layer. A magnetization of the third magnetic layer is configured to change in accordance with the deformation of the film unit.

According to one embodiment, a blood pressure sensor includes a pressure sensor. The pressure sensor includes a strain sensing element, and a support supporting the film unit. The strain sensing element includes a film unit, and a sensing unit. The film unit has a film surface and is deformable. The sensing unit includes a first sensing element and a second sensing element. The first sensing element is provided between a part of the film unit and the second sensing element. The first sensing element includes a first magnetic layer, a second magnetic layer provided apart from the first magnetic layer in a first direction crossing the film surface, and a first spacer layer provided between the first magnetic layer and the second magnetic layer. A magnetization of the first magnetic layer is configured to change in accordance with a deformation of the film unit. The second sensing element includes a third magnetic layer, a fourth magnetic layer provided apart from the third magnetic layer in the first direction, and a second spacer layer provided between the third magnetic layer and the fourth magnetic layer. A magnetization of the third magnetic layer is configured to change in accordance with the deformation of the film unit.

According to one embodiment, a touch panel includes a touch panel. The pressure sensor includes a strain sensing element, and a support supporting the film unit. The strain sensing element includes a film unit, and a sensing unit. The film unit has a film surface and is deformable. The sensing unit includes a first sensing element and a second sensing element. The first sensing element is provided between a part of the film unit and the second sensing element. The first sensing element includes a first magnetic layer, a second magnetic layer provided apart from the first magnetic layer in a first direction crossing the film surface, and a first spacer layer provided between the first magnetic layer and the second magnetic layer. A magnetization of the first magnetic layer is configured to change in accordance with a deformation of the film unit. The second sensing element includes a third magnetic layer, a fourth magnetic layer provided apart from the third magnetic layer in the first direction, and a second spacer layer provided between the third magnetic layer and the fourth magnetic layer. A magnetization of the third magnetic layer is configured to change in accordance with the deformation of the film unit.

Various embodiments will be described hereinafter with reference to the accompanying drawings.

The drawings are schematic or conceptual; and the relationships between the thickness and width of portions, the proportions of sizes among portions, etc, are not necessarily the same as the actual values thereof. The dimensions and proportions may be illustrated differently among drawings, even for identical portions.

In the specification of this application and the drawings, components similar to those described in regard to a drawing thereinabove are marked with the same reference numerals, and a detailed description is omitted as appropriate.

First Embodiment

FIG. 1A to FIG. 1F are schematic views illustrating a strain sensing element according to a first embodiment.

Figure 1B:
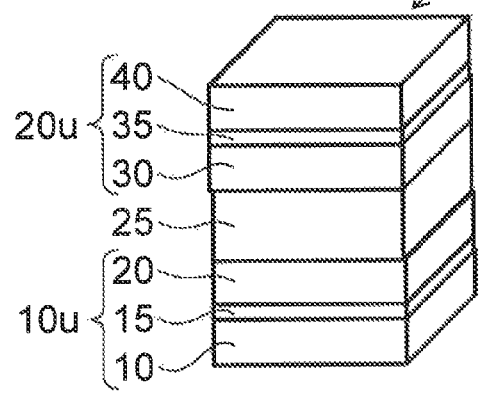

FIG. 1A is a schematic perspective view illustrating a strain sensing element according to the embodiment. FIG. 1B is a schematic perspective view illustrating part of the strain sensing element. FIG. 1C to FIG. 1F are schematic cross-sectional views illustrating part of the strain sensing element.

As shown in FIG. 1A, a strain sensing element 80 according to the embodiment includes a film unit 70d and a sensing unit 50. The strain sensing element 80 is used for a pressure sensor 310, for example. The pressure sensor 310 includes the strain sensing element 80 and a support 70s. The support 70s holds the film unit 70d.

A substrate is used as the support 70s, for example. The film unit 70d is supported by the support 70s. The film unit 70d has flexibility. The film unit 70d is a diaphragm, for example. The film unit 70d may be integrated with or separated from the support 70s. For the film unit 70d, the same material as the support 70s may be used, or a different material from the support 70s may be used. Part of a substrate that forms the support 70s may be removed, and a portion of the substrate with a smaller thickness may form the film unit 70d.

The thickness of the film unit 70d is smaller than the thickness of the support 70s. In the case where the same material is used for the film unit 70d and the support 70s and they are integrated together, a portion with a smaller thickness forms the film unit 70d, and a portion with a larger thickness forms the support 70s.

The support 70s may have a through hole (for example, a hollow portion 70h) penetrating through the support 70s in the thickness direction, and the film unit 70d may be provided so as to cover the through hole. At this time, the film of the material that forms the film unit 70d may extend also on a portion other than the through hole of the support 70s, for example. At this time, of the film of the material that forms the film unit 70d, a portion overlapping with the through hole forms the film unit 70d.

The film unit 70d has an outer edge 70r. In the case where the same material is used for the film unit 70d and the support 70s and they are integrated together, the outer edge 70r of the portion with a smaller thickness is the outer edge 70r of the film unit 70d. In the case where the support 70s has a through hole penetrating through the support 70s in the thickness direction and the film unit 70d is provided so as to cover the through hole, the outer edge 70r of the portion overlapping with the through hole of the film of the material that forms the film unit 70d is the outer edge 70r of the film unit 70d.

The support 70s may continuously support the outer edge 70r of the film unit 70d, and may support part of the outer edge 70r of the film unit 70d.

The sensing unit 50 is provided on the film unit 70d.

In the specification of this application, the state of being "provided on" includes not only the state of being provided in direct contact but also the state of being provided via another component.

The direction from the film unit 70d toward the sensing unit 50 is defined as the Z-axis direction. One direction perpendicular to the Z-axis direction is defined as the X-axis direction. The direction perpendicular to the Z-axis direction and the X-axis direction is defined as the Y-axis direction.

The upper surface (major surface) of the film unit 70d is substantially perpendicular to the Z-axis direction, for example. The upper surface of the film unit 70d spreads in the X-Y plane.

In this example, a plurality of sensing units 50 are provided on the film unit 70d. The number of sensing units 50 provided on the film unit 70d may be one.

A first interconnection 61 and a second interconnection 62 are provided in the pressure sensor 310. The first interconnection 61 is connected to the sensing unit 50. The second interconnection 62 is connected to the sensing unit 50. An interlayer insulating film is provided between the first interconnection 61 and the second interconnection 62, for example, and the first interconnection 61 and the second interconnection 62 are electrically insulated. A voltage is applied between the first interconnection 61 and the second interconnection 62. The voltage is applied to the sensing unit 50 via the first interconnection 61 and the second interconnection 62. When a pressure is applied to the pressure sensor 310, the film unit 70d is deformed. In the sensing unit 50, the electric resistance changes in accordance with the deformation of the film unit 70d. The pressure can be sensed by sensing the change in electric resistance change via the first interconnection 61 and the second interconnection 62.

As the support 70s, a plate-like substrate may be used, for example. The hollow portion 70h is provided in the substrate, for example.

For the support 70s, a semiconductor material such as silicon, a conductive material such as a metal, or an insulating material may be used, for example. The support 70s may include silicon oxide, silicon nitride, or the like, for example. The interior of the hollow portion 70h is in a reduced pressure state (vacuum state), for example. The interior of the hollow portion 70h may be filled with a gas such as air or a liquid. The interior of the hollow portion 70h is designed so that the film unit 70d can bend. The interior of the hollow portion 70h may be connected to the outside air.

The film unit 70d is provided on the hollow portion 70h. As the film unit 70d, a portion thinned by processing of a substrate that forms the support 70s is used, for example. The thickness (the length in the Z-axis direction) of the film unit 70d is smaller than the thickness (the length in the Z-axis direction) of the substrate.

When a pressure is applied to the film unit 70d, the film unit 70d bends. The pressure corresponds to the pressure that is to be sensed by the pressure sensor 310. The applied pressure includes pressure caused by sound waves, ultrasonic waves, or the like. In the case of sensing pressure caused by sound waves, ultrasonic waves, or the like, the pressure sensor 310 functions as a microphone.

For the film unit 70d, an insulating material is used, for example. The film unit 70d includes one of silicon oxide, silicon nitride, and silicon oxynitride, for example. A semiconductor material such as silicon may be used for the film unit 70d, for example. A metal material may be used for the film unit 70d, for example.

The thickness of the film unit 70d is not less than 0.1 micrometers ($\mu$m) and not more than 3 $\mu$m, for example. The thickness is preferably not less than 0.2 $\mu$m and not more than 1.5 $\mu$m. A stacked body of a silicon oxide film with a thickness of 0.2 $\mu$m and a silicon film with a thickness of 0.4 $\mu$m may be used as the film unit 70d, for example.

As illustrated in FIG. 1B, the sensing unit according to the embodiment includes a first sensing element 10u, an interposition layer 25, and a second sensing element 20u. The interposition layer 25 is disposed between the first sensing element 10u and the second sensing element 20u. The interposition layer 25 is provided as necessary and may be omitted.

The first sensing element 10u includes a first magnetic layer 10, a spacer layer 15, and a second magnetic layer 20. The second sensing element 20u includes a third magnetic layer 30, a spacer layer 35, and a fourth magnetic layer 40.

The pressure sensor 310 includes the film unit 70d and the sensing unit 50. The film unit 70d can be deformed. The film unit 70d has a film surface 70fs.

The sensing unit 50 includes the second sensing element 20u. The second sensing element 20u is apart from the film unit 70d in a first direction crossing the film surface 70fs.

The sensing unit 50 includes the first sensing element 10u. The first sensing element 10u is provided between the second sensing element 20u and the film unit 70d.

The first sensing element 10u includes the first magnetic layer 10 in which the magnetization changes in accordance with the deformation of the film unit 70d, the second magnetic layer 20 provided apart from the first magnetic layer 10 in the first direction, and the spacer layer 15 provided between the second magnetic layer 20 and the first magnetic layer 10.

The second sensing element 20u includes the third magnetic layer 30 in which the magnetization changes in accordance with the deformation of the film unit 70d, the forth magnetic layer 40 provided apart from the third magnetic layer 30 in the first direction, and the spacer layer 35 provided between the fourth magnetic layer 40 and the third magnetic layer 30.

Figures 1C, 1D:
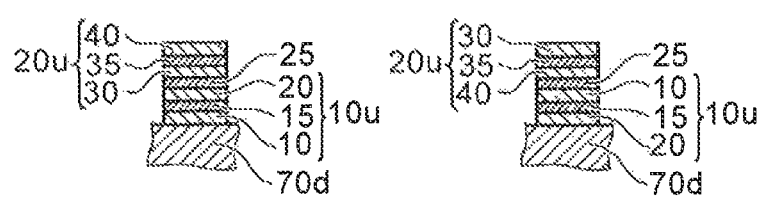

In the example shown in FIG. 1C the third magnetic layer 30 is disposed between the fourth magnetic layer 40 and the film unit 70d. The first magnetic layer 10 is disposed between the second magnetic layer 20 and the film unit 70d.

In the example shown in FIG. 1D, the fourth magnetic layer 40 is disposed between the third magnetic layer 30 and the film unit 70d. The second magnetic layer 20 is disposed between the first magnetic layer 10 and the film unit 70d.

Figures 1E, 1F:
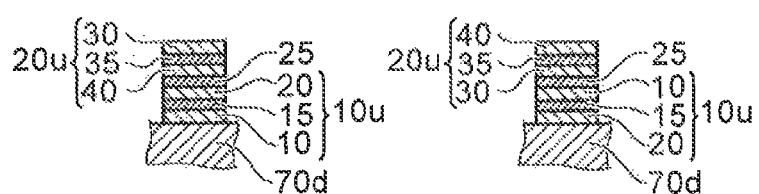

In the example shown in FIG. 1E, the fourth magnetic layer 40 is disposed between the third magnetic layer 30 and the film unit 70d. The first magnetic layer 10 is disposed between the second magnetic layer 20 and the film unit 70d.

In the example shown in FIG. 1F, the third magnetic layer 30 is disposed between the fourth magnetic layer 40 and the film unit 70d. The second magnetic layer 20 is disposed between the first magnetic layer 10 and the film unit 70d.

In the following, the configuration illustrated in FIG. 1B and FIG. 1C is described. The following description can be applied to the examples shown in FIG. 1D to FIG. 1F.

The positions in the plane (the X-Y plane) of the first sensing element 10u and the second sensing element 20u overlap. The first sensing element 10u and the second sensing element 20u are disposed in different positions in the perpendicular-to-plane direction (the Z-axis direction).

As described later, the current flowing between the fourth magnetic layer 40 and the third magnetic layer 30 flows between the second magnetic layer 20 and the first magnetic layer 10, for example.

A ferromagnetic layer is used as the first magnetic layer 10 and the second magnetic layer 20, for example. The second magnetic layer 20 is a reference layer, for example. The first magnetic layer 10 is a magnetization free layer, for example. A magnetization fixed layer or a magnetization free layer is used as the reference layer. The change in magnetization of the first magnetic layer 10 may be easier than the change in magnetization of the second magnetic layer 20, for example. Thereby, a change can be made to the relative angle between the magnetization of the first magnetic layer 10 and the magnetization of the second magnetic layer 20 when a force is applied to the substrate and the substrate is bent, as described later.

A ferromagnetic layer is used as the third magnetic layer 30 and the fourth magnetic layer 40, for example. The fourth magnetic layer 40 is a reference layer, for example. The third magnetic layer 30 is a magnetization free layer, for example. A magnetization fixed layer or a magnetization free layer is used as the reference layer. The change in magnetization of the third magnetic layer 30 may be easier than the change in magnetization of the fourth magnetic layer 40, for example. In the embodiment, a change can be made to the relative angle between the magnetization of the third magnetic layer 30 and the magnetization of the fourth magnetic layer 40 when a force is applied to the substrate and the substrate is deformed, as described later.

In the example shown in FIG. 1B, the sensing unit 50 includes two sensing elements of the first sensing element 10u and the second sensing element 20u. In the embodiment, the number of sensing elements may be three or more.

As shown in FIG. 1B, in the sensing unit 50, the plurality of stacked sensing elements are connected in series to one another. When the number of sensing elements connected in series is denoted by N, the electric signal obtained is N times of that when the number of sensing elements is one. On the other hand, the thermal noise and the Schottky noise are $N^{1/2}$ times. That is, the S/N ratio (signal-noise ratio; SNR) is $N^{1/2}$ times. By increasing the number N of sensing elements connected in series, the S/N ratio can be improved without increasing the size of the film unit.

FIG. 2A to FIG. 2I are schematic perspective views illustrating operations of the strain sensing element according to the embodiment.

In the drawings, for easier viewing of the drawings, the first magnetic layer 10 and the second magnetic layer 20 in the first sensing element 10u are depicted. The drawings illustrate the case where a magnetization fixed layer is used as the second magnetic layer 20 and a magnetization free layer is used as the first magnetic layer 10. Similar operations to the first sensing element 10u are obtained when a magnetization fixed layer is used as the fourth magnetic layer 40 and a magnetization free layer is used as the third magnetic layer 30 in the second sensing element 20u.

In the embodiment, a strain is generated in the sensing element when the substrate is bent due to a force from the outside. The sensing element has the function of converting the change in strain to a change in electric resistance.

The operation in which the sensing element functions as a strain sensor is based on application of "inverse magnetostriction effect" and "magnetoresistance effect," The "inverse magnetostriction effect" is obtained in the ferromagnetic layer used as the magnetization free layer (in this example, the first magnetic layer 10). The "magnetoresistance effect" is exhibited in the stacked film including the magnetization free layer (the first magnetic layer 10), the spacer layer 15, and the magnetization fixed layer (the second magnetic layer 20).

The "inverse magnetostriction effect" is a phenomenon in which the magnetization of a ferromagnetic material is changed by a strain applied to the ferromagnetic material. That is, when an external strain is applied to the stacked film of the sensing element, the magnetization direction of the magnetization free layer is changed. Consequently, the relative angle between the magnetization of the magnetization free layer and the magnetization of the magnetization fixed layer is changed. At this time, a change in electric resistance is caused by the "magnetoresistance effect (MR effect)." The MR effect includes GMR (giant magnetoresistance) effect, TMR (tunneling magnetoresistance) effect, or the like, for example. The MR effect is exhibited by passing a current through the stacked film to read the change in relative angle between the directions of the magnetizations as an electric resistance change. A strain is applied to the sensing element due to a strain applied to the stacked film, for example. The direction of the magnetization of the magnetization free layer is changed by the strain, and the relative angle between the direction of the magnetization of the magnetization free layer and the direction of the magnetization of the magnetization fixed layer is changed. That is, the MR effect appears due to the inverse magnetostriction effect.

When the ferromagnetic material used for the magnetization free layer has a positive magnetostriction constant, the direction of the magnetization changes so that the angle between the direction of the magnetization and the direction of a tensile strain becomes smaller and the angle between the direction of the magnetization and the direction of a compressive strain becomes larger. When the ferromagnetic material used for the magnetization free layer has a negative magnetostriction constant, the direction of the magnetization changes so that the angle between the direction of the magnetization and the direction of a tensile strain becomes larger and the angle between the direction of the magnetization and the direction of a compressive strain becomes smaller.

When the combination of the materials of the stacked film of the magnetization free layer, the spacer layer 15, and the magnetization fixed layer has a positive magnetoresistance effect, the electric resistance decreases as the relative angle between the magnetization free layer and the magnetization fixed layer decreases. When the combination of the materials of the stacked film of the magnetization free layer, the spacer layer 15, and the magnetization fixed layer has a negative magnetoresistance effect, the electric resistance increases as the relative angle between the magnetization free layer and the magnetization fixed layer decreases.

Examples of the change in magnetization will now be described for an example in which the ferromagnetic materials used for the magnetization free layer has a positive magnetostriction constant, the stacked film of the magnetization free layer, the spacer layer 15, and the magnetization fixed layer has a positive magnetoresistance effect, and both of the magnetizations of the magnetization free layer and the magnetization fixed layer are directed to the in-plane direction.

Figure 2A:
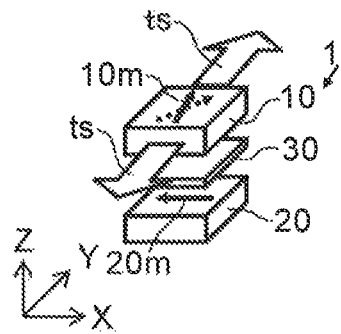
FIG. 2A to FIG. 2I are schematic perspective views showing operations of the strain sensing element according to the embodiment.
Figure 2B:
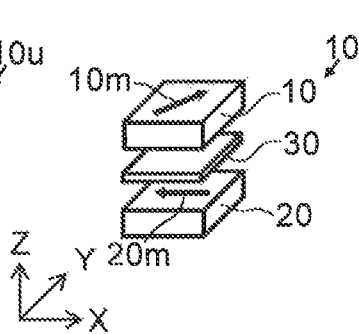
Figure 2C:
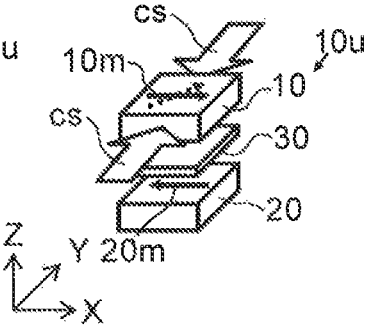

FIG. 2A to FIG. 2I illustrate operations in one of the sensing elements included in the sensing unit 50. FIG. 2A to FIG. 2C illustrate states where a "stain in the perpendicular direction" is applied to the sensing element. The "strain in the perpendicular direction" is an anisotropic strain in the direction perpendicular to the stacking direction (for example, the direction from the second magnetic layer 20 toward the first magnetic layer 10) and perpendicular to the direction of the magnetization of the magnetization fixed layer (the second magnetic layer 20).

Figure 2D:
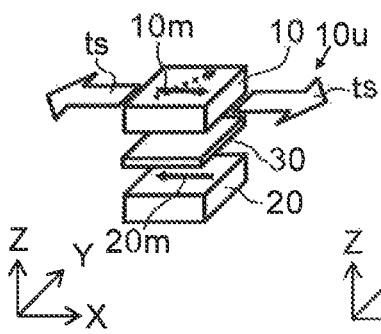
Figure 2E:
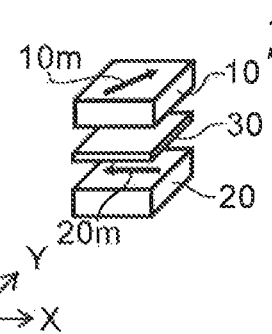
Figure 2F:
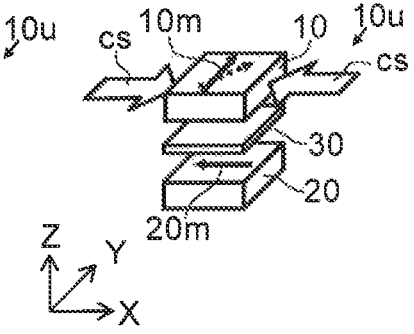

FIG. 2D to FIG. 2F illustrate states where a "strain in the parallel direction" is applied to the sensing element. The "strain in the parallel direction" is an anisotropic strain that is anisotropic in the direction perpendicular to the stacking direction and parallel to the direction of the magnetization of the magnetization fixed layer.

Figure 2G:
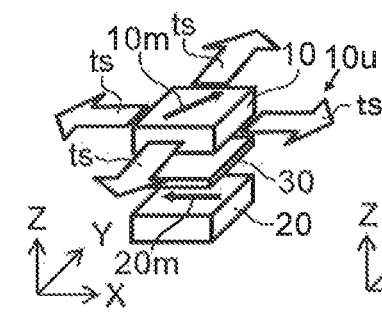
Figure 2H:
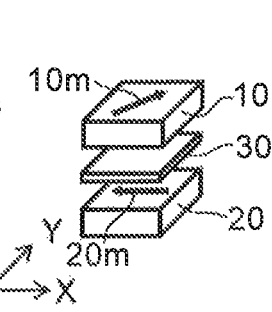
Figure 2I:
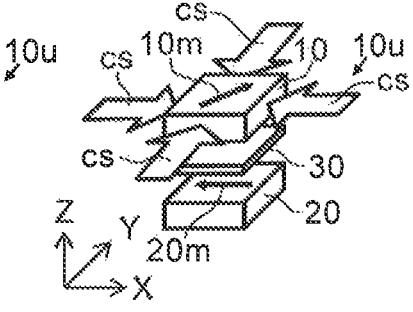

FIG. 2G to FIG. 2I illustrate states where an "isotropic strain" is applied to the sensing element. The "isotropic strain" is a strain that is isotropic in the plane perpendicular to the stacking direction.

FIG. 2B, FIG. 2E, and FIG. 2H correspond to the state where no strain is applied, FIG. 2A, FIG. 2D, and FIG. 2G correspond to the state where a tensile strain ts is applied. FIG. 2C, FIG. 2F, and FIG. 2I correspond to the state where a compressive strain cs is applied.

As illustrated in FIG. 2A, when a tensile strain ts that is a "strain in the perpendicular direction" is applied, the angle between the direction of the magnetization 10m of the magnetization free layer (the first magnetic layer 10) and the direction of the magnetization 20m of the magnetization fixed layer (the second magnetic layer 20) (the relative angle of magnetization) becomes smaller than that in the state where no strain is applied (the state of FIG. 2B). Consequently, the electric resistance in the sensing element is decreased.

As illustrated in FIG. 2C, when a compressive strain cs that is a "strain in the perpendicular direction" is applied, the relative angle of magnetization becomes larger than that in the state where no strain is applied (the state of FIG. 2B). Consequently, the electric resistance is increased.

As illustrated in FIG. 2D, when a tensile strain ts that is a "strain in the parallel direction" is applied, the relative angle of magnetization becomes larger than that in the state where no strain is applied (the state of FIG. 2E). Consequently, the electric resistance in the sensing element is increased.

As illustrated in FIG. 2F, when a compressive strain cs that is a "strain in the parallel direction" is applied, the relative angle of magnetization becomes smaller than that in the state where no strain is applied (the state of FIG. 2E). Consequently, the electric resistance in the sensing element is decreased.

The relationship of the increase and decrease in relative angle of magnetization to the strain in the "strain in the parallel direction" is opposite to the relationship in the "strain in the perpendicular direction." The change in electric resistance with respect to the polarity of strain is opposite in polarity between the "strain in the parallel direction" and the "strain in the perpendicular direction."

As illustrated in FIG. 2G to FIG. 2I, when an "isotropic strain" is applied, the direction of the magnetization 10m of the magnetization free layer (the first magnetic layer 10) does not change. Hence, the electric resistance is not changed by either the strain with the polarity of tensile strain ts or that of compressive strain cs.

Thus, in the sensing element, the resulting change in electric resistance varies with the direction of the applied strain.

In the sensing element 50 in which a plurality of sensing elements are stacked as illustrated in FIG. 1A and FIG. 1B, the plurality of sensing elements operate similarly when the same materials are used for the respective layers of the plurality of sensing elements, for example. The polarities of the electric signals generated in the plurality of sensing elements etc, are the same, for example.

Figure 3A:
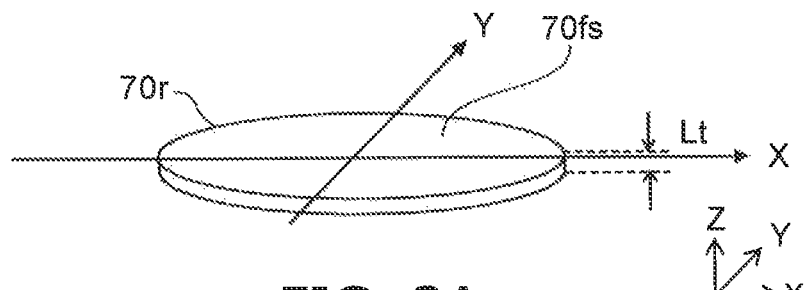
FIG. 3A to FIG. 3C are schematic diagrams showing characteristics of the strain sensing element according to the embodiment.
Figure 3B:
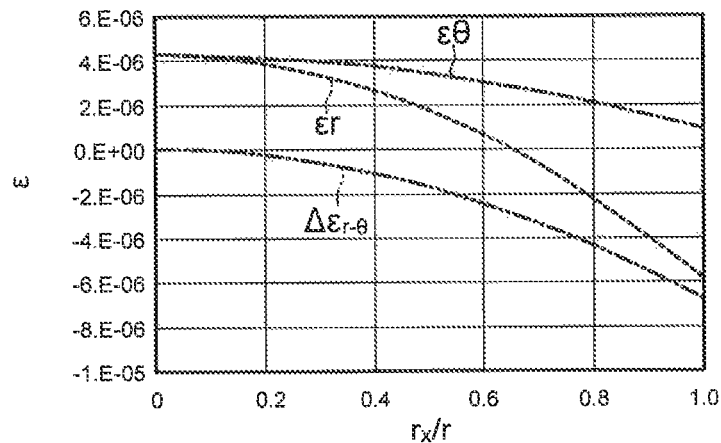
Figure 3C:
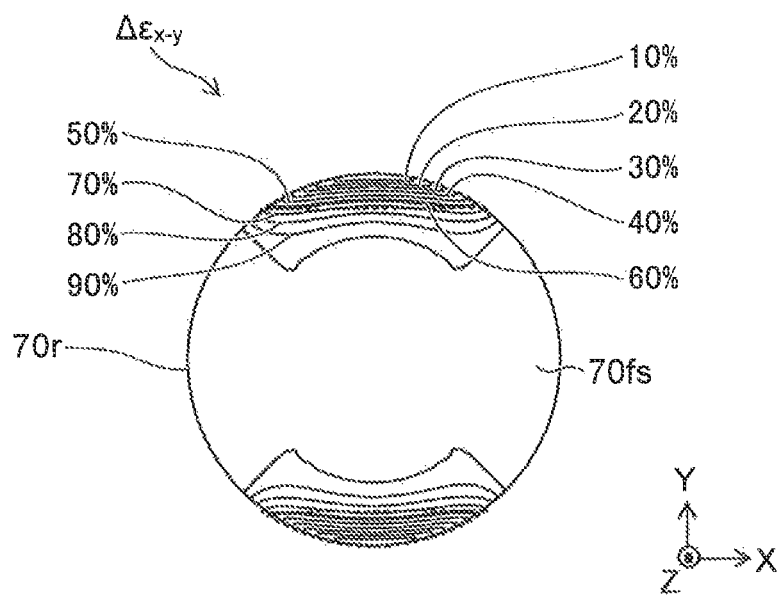

FIG. 3A to FIG. 3C are schematic diagrams illustrating characteristics of the strain sensing element according to the embodiment.

FIG. 3A is a schematic perspective view of the film unit 70d. FIG. 3B is a graph illustrating characteristics of the pressure sensor. FIG. 3C is a schematic diagram illustrating characteristics of the pressure sensor.

FIG. 3B and FIG. 3C illustrate strain generated on the surface of the film unit 70d when a pressure is applied to the film unit 70d.

FIG. 3B and FIG. 3C illustrate the simulation results of characteristics of the pressure sensor 310. FIG. 3B illustrates the strain $\epsilon$ generated on the film unit 70d to which a pressure is applied. The vertical axis in FIG. 3B is the strain $\epsilon$ (no unit). The horizontal axis of FIG. 3B is the value of the distance from the center normalized by the radius ($r_X/r$). In these drawings, the strain $\epsilon$ is positive for tensile strains, and the strain $\epsilon$ is negative for compressive strains. In these drawings, a first strain $\epsilon r$ that is a strain in the radius direction, a second strain $\epsilon \theta$ that is a strain in the circumference direction, and the difference between them (the anisotropic strain $\Delta\epsilon_{r-\theta}$) are shown. The anisotropic strain $\Delta\epsilon_{r-\theta}$ is the difference between the first strain $\epsilon r$ and the second strain $\epsilon \theta$. The anisotropic strain $\Delta\epsilon$ contributes to the change in direction of the magnetization of the magnetization free layer of the sensing element.

FIG. 3C illustrates the distribution in the X-Y plane of the anisotropic strain $\Delta\epsilon_{X-Y}$ generated on the film unit 70d.

As shown in FIG. 3A, in this example, the planar shape of the film unit 70d is a circle. In this example, the diameter of the film unit 70d is 500 μm. The thickness Lt of the film unit 70d is 2 μm.

In this example, the outer edge 70r of the film unit 70d is made a fixed end completely restrained. In this example, the strain $\epsilon$ generated on the surface of the film unit 70d (the film surface 70fs) is analyzed by finite element analysis. The analysis is made by using Hooke's law for each element divided by the finite element method.

In this simulation, the material of the film unit 70d is assumed to be silicon. The Young's modulus of the film unit 70d is 165 GPa, and the Poisson's ratio is 0.22. In the simulation, the strain $\epsilon$ of the surface of the film unit 70d when a uniform pressure of 13.33 kPa is applied from the back surface of the film unit 70d is found. In the finite element method, the planar mesh size in the X-Y plane is set to 5 μm, and the mesh size in the thickness direction is 2 μm.

As shown in FIG. 3B, in the vicinity of the center of the film unit 70d, the first strain Er and the second strain εθ are a tensile strain. In the vicinity of the center, the film unit 70d is bent in a convex manner. In the vicinity of the outer edge 70r of the film unit 70d, the first strain Er and the second strain εθ are a compressive strain. In the vicinity of the outer edge 70r, the film unit 70d is bent in a concave manner. In the vicinity of the center, the anisotropic strain $\Delta\epsilon_{r\text{-}\theta}$ is zero, and there is an isotropic strain. In the vicinity of the outer edge 70r, the anisotropic strain $\Delta\epsilon_{r\text{-}\theta}$ shows a value of compression, and the largest anisotropic strain is obtained in the immediate vicinity of the outer edge 70r. In the circular film unit 70d, the anisotropic strain $\Delta\epsilon_{r\text{-}\theta}$ is similarly obtained in the radial directions passing through the center. In the embodiment, the sensing element is preferably disposed in the vicinity of the outer edge 70r of the film unit 70d where an anisotropic strain is obtained.

In FIG. 3B, the anisotropic strain $\Delta\epsilon_{r\text{-}\theta}$ is expressed using a polar coordinate system. In FIG. 3C, the anisotropic strain $\Delta\epsilon_{r\text{-}\theta}$ in the polar coordinate system is transformed to the anisotropic strain $\Delta\epsilon_{X\text{-}Y}$ in a Cartesian coordinate system. FIG. 3C illustrates the result of analysis of the entire surface of the film unit 70d.

The value (absolute value) of the anisotropic strain $\Delta\epsilon_{X\text{-}Y}$ is largest in the immediate vicinity of the outer edge 70r.

In the contour figure shown in FIG. 3C, the line indicated by the letters of "10%" represents the position where a value of anisotropic strain $\Delta\epsilon_{X\text{-}Y}$ decreased by 10% from the value of the largest anisotropic strain $\Delta\epsilon_{X\text{-}Y}$ in the immediate vicinity of the outer edge 70r is obtained, for example. That is, the line indicated by the letters of "10%" represents the position where a value of anisotropic strain $\Delta\epsilon_{X\text{-}Y}$ of 90% of the value of the largest anisotropic strain $\Delta\epsilon_{X\text{-}Y}$ in the immediate vicinity of the outer edge 70r is obtained. In the figure shown in FIG. 3C, the line indicated by the letters of "90%" represents the position where a value of anisotropic strain $\Delta\epsilon_{X\text{-}Y}$ decreased by 90% from the value of the largest anisotropic strain $\Delta\epsilon_{X\text{-}Y}$ in the immediate vicinity of the outer edge 70r is obtained. That is, the line indicated by the letters of "90%" represents the position where a value of anisotropic strain $\Delta\epsilon_{X\text{-}Y}$ of 10% of the value of the largest anisotropic strain $\Delta\epsilon_{X\text{-}Y}$ in the immediate vicinity of the outer edge 70r is obtained. The lines indicated by the letters of "20%" to "80%" are similar to the above.

As can be seen from FIG. 3C, similar anisotropic strains $\Delta\epsilon_{X\text{-}Y}$ are obtained in a limited region.

Sensing elements are arranged on the outer edge 70r of the film unit 70d, for example. The magnetization directions of the pinned layers are uniformly directed to the direction of magnetic field annealing as described later, and are thus directed to the same direction. When it is attempted to obtain similar electric resistance changes (for example, polarities etc.) with respect to the pressure by arranging sensing elements on the outer edge 70r, they are arranged in a region where similar anisotropic strains $\Delta\epsilon_{X\text{-}Y}$ are obtained as shown in FIG. 3C. The number of sensing elements by which similar electric resistance changes with respect to the pressure are obtained is constrained by the area of the planar region like that shown in FIG. 3C where similar anisotropic strains are obtained.

When the area of the film unit 70d is increased, the area of the planar region where similar anisotropic strains are obtained is increased in proportion to that area, for example. However, the number of pressure sensor elements obtained on the same wafer is reduced. Problems arise such as one from the viewpoint of manufacturing throughput and a degradation in frequency characteristics due to the increase in area of the film unit 70d in applications to microphones. Hence, it is not preferable to increase the area of the film unit 70d excessively.

On the other hand, when the dimensions of the sensing element are reduced, a larger number of sensing elements can be arranged in the planar region where similar anisotropic strains are obtained. However, an excessive reduction in dimensions of the sensing element presents a problem with processing accuracy. Furthermore, when the dimensions of the sensing element are reduced, the influence of demagnetization fields of magnetic layers may become greater, and this may adversely influence the operation of magnetization rotation with respect to strain.

Thus, in the case where sensing elements are arranged on the film unit 70d, there is a restriction on the number of sensing elements from the viewpoint of the restriction of dimensions on the plane, such as the area of the film unit 70d, the dimensions of the sensing element, and the area of the anisotropic strain generation region produced on the film unit 70d.

In the sensing unit 50 according to the embodiment, a plurality of sensing elements are arranged in different positions in the perpendicular-to-plane direction. Thereby, the restriction on the number of sensing elements arranged on the plane is relaxed. Thereby, the number of sensing elements arranged in a limited region on the film unit 70d where similar anisotropic strains are generated can be sufficiently increased.

In a sensing element including a pinned layer (for example, the second magnetic layer 20) like that shown in FIG. 2A to FIG. 2I, the advantage of using the sensing unit 50 in which a plurality of sensing elements are stacked in the stacking direction is particularly great. As shown in FIG. 2A to FIG. 2I, in the sensing element using a pinned layer, the resulting output varies depending on the direction of the strain applied to the pinned layer. Hence, in the case where a plurality of sensing elements by which similar electric resistance changes (for example, polarities etc.) with respect to the strain are obtained are arranged, sensing units 50 are arranged in a region on the film unit 70d where similar anisotropic strains are generated. At this time, the restriction on the element arrangeable position in the plane will be great. For the sensing element including a pinned layer, the advantage of using the configuration in which a plurality of sensing elements are stacked in the perpendicular-to-plane direction is great because a larger number of sensing elements are arranged in the element arrangeable region in the plane, like sensing units 50 according to the embodiment.

Even in the case of a sensing element including no pinned layer like that described later, the advantage of using the sensing unit 50 in which a plurality of sensing elements are stacked in the stacking direction can be enjoyed.

As shown in FIG. 1B, in the sensing unit 50, the plurality of stacked sensing elements are connected in series. When the number of sensing elements connected in series is denoted by N, the electric signal obtained is N times of that when the number of sensing elements is one. On the other hand, the thermal noise and the Schottky noise are $N^{1/2}$ times. That is, the S/N ratio (signal-noise ratio; SNR) is $N^{1/2}$ times. By increasing the number N of sensing elements connected in series, the S/N ratio can be improved without increasing the size of the film unit. By arranging a plurality of sensing elements in the stacking direction, the restriction on the number of sensing elements arranged in the anisotropic strain region produced in a limited region on the film unit 70d shown in FIG. 3C can be relaxed, and the number of sensing elements can be increased. Consequently, the S/N ratio can be improved. That is, a high-sensitivity strain sensing element and a high-sensitivity pressure sensor can be provided.

Figure 4A:
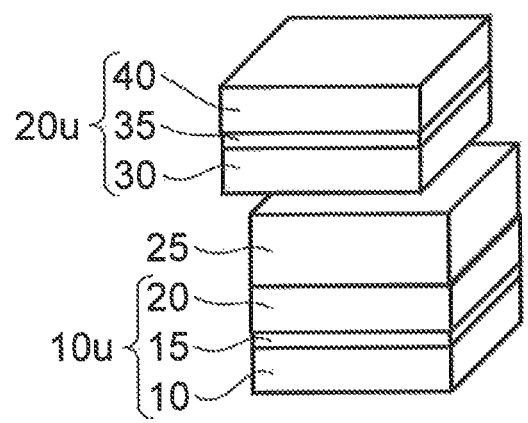
FIG. 4A and FIG. 4B are schematic views showing another strain sensing element according to the first embodiment.
Figure 4B:
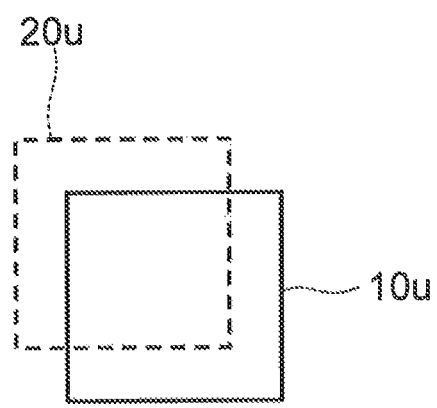

FIG. 4A and FIG. 4B are schematic views illustrating another strain sensing element according to the first embodiment.

FIG. 4A is a schematic perspective view illustrating part of a pressure sensor. FIG. 4A is a perspective view of the sensing unit 50. FIG. 4B is a planar view illustrating part of the pressure sensor. FIG. 4B is a plan view of the sensing unit 50.

As shown in FIG. 4A, the first sensing element 10u and the second sensing element 20u are disposed to be stacked in different positions in the perpendicular-to-plane direction. In FIG. 4A, the first sensing element 10u and the second sensing element 20u are electrically connected in series via the interposition layer 25.

There may be a misalignment between the planar position of the first sensing element 10u and the planar position of the second sensing element 20u as long as there is an overlapping portion as shown in FIG. 4A and FIG. 4B.

Examples of the sensing unit 50 used for a strain sensing element and a pressure sensor according to the embodiment will now be described.

In the following, the description of "material A/material B" refers to the state where a layer of material B is provided on a layer of material A.

Figure 5:
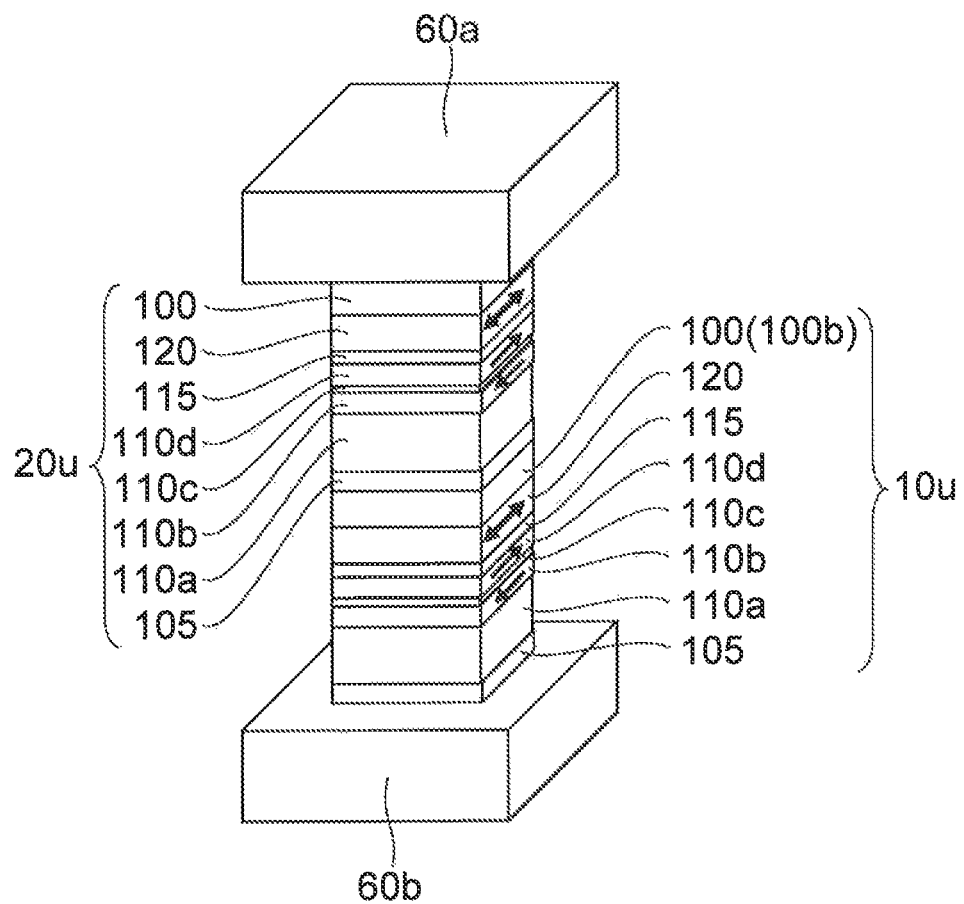
FIG. 5 is a schematic perspective view showing part of a strain sensing element according to the embodiment.

FIG. 5 is a schematic perspective view illustrating part of a strain sensing element according to the embodiment.

FIG. 5 illustrates the sensing unit 50. As shown in FIG. 5, the sensing unit used in the embodiment includes a lower electrode 60b, the first sensing element 10u, the second sensing element 20u, and an upper electrode 60a that are sequentially aligned. The first sensing element 10u includes an underlayer 105, a pinning layer 110a, a second pinned layer 110b, a magnetic coupling layer 110c, a first pinned layer 110d, a spacer layer 115, a free layer 120 (a magnetization free layer), and a cap layer 100 (or an interposition layer 100b). The second sensing element 20u includes the underlayer 105, the pinning layer 110a, the second pinned layer 110b, the magnetic coupling layer 110c, the first pinned layer 110d, the spacer layer 115, the free layer 120, and the cap layer 100. In FIG. 5, each of the first sensing element 10u and the second sensing element 20u includes a bottom spin valve structure having a synthetic pin layer. The material used for each layer is similar between the first sensing element 10u and the second sensing element 20u. The material of each layer may be different between the first sensing element 10u and the second sensing element 20u.

One of the upper electrode 60a and the lower electrode 60b is a first electrode, for example. The other of the upper electrode 60a and the lower electrode 60b is a second electrode. By applying a voltage between the upper electrode 60a and the lower electrode 60b, a current in the perpendicular-to-plane direction is passed through the first sensing element 10u and the second sensing element 20u.

In the example shown in FIG. 5, in the first sensing element 10u, the first pinned layer 110d, the spacer layer 115, and the magnetization free layer 120 are provided. The first pinned layer 110d, the spacer layer 115, and the magnetization free layer 120 in the first sensing element 10u correspond to the second magnetic layer 20, the first spacer layer 15, and the first magnetic layer 10 of the example shown in FIG. 1D, respectively. In the second sensing element 20u, the first pinned layer 110d, the spacer layer 115, and the magnetization free layer 120 are provided. The first pinned layer 110d, the spacer layer 115, and the magnetization free layer 120 in the second sensing element 20u correspond to the fourth magnetic layer 40, the second spacer layer 35, and the third magnetic layer 30 of the example shown in FIG. 1D, respectively.

As the underlayer 105 of the first sensing element 10u, Ta/Ru is used, for example. The thickness (the length in the Z-axis direction) of the Ta layer is 3 nm, for example. The thickness of the Ru layer is 2 nm, for example. As the pinning layer 110a, an IrMn layer with a thickness of 7 nm is used, for example. As a second magnetization fixed layer (the second pinned layer 110b), a $Co_{75}Fe_{25}$ layer with a thickness of 2.5 nm is used, for example. As the magnetic coupling layer 110c, a Ru layer with a thickness of 0.9 nm is used, for example. As a first magnetization fixed layer (the first pinned layer 110d), a $Co_{40}Fe_{40}B_{20}$ layer with a thickness of 3 nm is used, for example. As the spacer layer 115, an MgO layer with a thickness of 2.0 nm is used, for example. As the magnetization free layer, $Co_{40}Fe_{40}B_{20}$ with a thickness of 4 nm is used, for example. As the interposition layer 100b, Ta/Ru is used, for example. The thickness of the Ta layer is 1 nm, for example. The thickness of the Ru layer is 5 nm, for example.

As the underlayer 105 of the second sensing element 20u, Ta/Ru is used, for example. The thickness (the length in the Z-axis direction) of the Ta layer is 3 nm, for example. The thickness of the Ru layer is 2 nm, for example. As the pinning layer 110a, an IrMn layer with a thickness of 7 nm is used, for example. As the second magnetization fixed layer 110b, a $Co_{75}Fe_{25}$ layer with a thickness of 2.5 nm is used, for example. As the magnetic coupling layer 110c, a Ru layer with a thickness of 0.9 nm is used, for example. As the first magnetization fixed layer, a $Co_{40}Fe_{40}B_{20}$ layer with a thickness of 3 nm is used, for example. As the spacer layer 115, an MgO layer with a thickness of 2.0 nm is used, for example. As the magnetization free layer, $Co_{40}Fe_{40}B_{20}$ with a thickness of 4 nm is used, for example. As the cap layer 100, Ta/Ru is used, for example. The thickness of the Ta layer is 1 nm, for example. The thickness of the Ru layer is 15 nm, for example.

For the lower electrode 60b and the upper electrode 60a, at least one of aluminum (Al), aluminum-copper alloy (Al—Cu), copper (Cu), silver (Ag), and gold (Au) is used, for example. By using such a material with a relatively small electric resistance as the lower electrode 60b and the upper electrode 60a, a current can be passed through the sensing element efficiently. A nonmagnetic material may be used for the lower electrode 60b.

In the lower electrode 60b, a layer of at least one of Al, Al—Cu, Cu, Ag, and Au provided between an underlayer for the lower electrode (not shown) and a cap layer (not shown) may be provided. As the lower electrode 60b, tantalum (Ta)/copper (Cu)/tantalum (Ta) or the like is used, for example. By using Ta as the underlayer for the lower electrode, the adhesion between the film unit 70d and the lower electrode is improved, for example. Also titanium (Ti), titanium nitride (TiN), or the like may be used as the underlayer for the lower electrode.

By using Ta as the cap layer of the lower electrode 60b, the oxidation of copper (Cu) or the like under the cap layer can be prevented. Also titanium (Ti), titanium nitride (TiN), or the like may be used as the cap layer for the lower electrode.

As the underlayer 105 of the first sensing element 10u, a stacked structure of a buffer layer (not shown) and a seed layer (not shown) may be used. The buffer layer eases the roughness of the surface of the lower electrode 60b or the film unit 70d, and improves the crystallinity of a layer stacked on the buffer layer, for example. As the buffer layer, at least one of tantalum (Ta), titanium (Ti), vanadium (V), tungsten (W), zirconium (Zr), hafnium (Hf), and chromium (Cr) is used, for example. An alloy including at least one of these materials may be used as the buffer layer.

The thickness of the buffer layer is preferably not less than 1 nm and not more than 10 nm. The thickness of the buffer layer is more preferably not less than 1 nm and not more than 5 nm. If the thickness of the buffer layer is too small, the buffer effect will be lost. If the thickness of the buffer layer is too large, the thickness of the sensing element will be too large. The seed layer is formed on the buffer layer, and has buffer effect. The buffer layer may be omitted. A Ta layer with a thickness of 3 nm is used as the buffer layer, for example.

The not-shown seed layer controls the crystal orientation of a layer stacked on the seed layer. The seed layer controls the crystal grain size of a layer stacked on the seed layer. A metal of the fcc structure (face-centered cubic structure), the hcp structure (hexagonal close-packed structure), or the bcc structure (body-centered cubic structure) or the like is used as the seed layer.

As the seed layer, ruthenium (Ru) of the hcp structure, NiFe of the fcc structure, or Cu of the fcc structure may be used, for example. Thereby, the crystal orientation of a spin valve film on the seed layer can be made the fcc(111) orientation. A Cu layer with a thickness of 2 nm or a Ru layer with a thickness of 2 nm is used as the seed layer, for example. When it is attempted to enhance the crystal orientation properties of a layer formed on the seed layer, the thickness of the seed layer is preferably not less than 1 nm and not more than 5 nm. The thickness of the seed layer is more preferably not less than 1 nm and not more than 3 nm. Thereby, the function as a seed layer of improving the crystal orientation is exhibited sufficiently. On the other hand, the seed layer may be omitted, for example.

The pinning layer 110a of the first sensing element 10u provides unidirectional anisotropy to the ferromagnetic layer of the second pinned layer 110b formed on the pinning layer, and fixes the magnetization of the ferromagnetic layer, for example. An antiferromagnetic layer is used as the pinning layer 110a, for example. At least one of IrMn, PtMn, PdPtMn, and RuRhMn is used for the pinning layer 110a, for example. The thickness of the pinning layer 110a is appropriately set to provide unidirectional anisotropy of a sufficient strength.

When PtMn or PdPtMn is used as the pinning layer 110a, the thickness of the pinning layer 110a is preferably not less than 8 nm and not more than 20 nm. The thickness of the pinning layer 110a is more preferably not less than 10 nm and not more than 15 nm. When IrMn is used as the pinning layer 110a, unidirectional anisotropy can be provided by a thinner pinning layer than when PtMn is used. In this case, the thickness of the pinning layer 110a is preferably not less than 4 nm and not more than 18 nm. The thickness of the pinning layer 110a is more preferably not less than 5 nm and not more than 15 nm. An $Ir_{22}Mn_{78}$ layer with a thickness of 7 nm is used as the pinning layer 110a, for example.

A hard magnetic layer may be used as the pinning layer 110a. As the hard magnetic layer, CoPt (the ratio of Co being not less than 50 at. % (atomic percent) and not more than 85 at. %), $(Co_xPt_{100-x})_{100-y}Cr_y$ (x being not less than 50 at. % and not more than 85 at. %, y being not less than 0 at. % and not more than 40 at. %), FePt (the ratio of Pt being not less than 40 at. % and not more than 60 at. %), or the like may be used, for example.

As the second pinned layer 110b, $Co_xFe_{100-x}$ alloy (x being not less than 0 at. % and not more than 100 at. %), $Ni_xFe_{100-x}$ alloy (x being not less than 0 at. % and not more than 100 at. %), or a material in which a nonmagnetic element is added to these is used, for example. As the second pinned layer 110b, at least one of Co, Fe, and Ni is used, for example. As the second pinned layer 110b, an alloy including at least one of these materials may be used. As the second pinned layer 110b, also $(Co_xFe_{100-x})_{100-y}B_y$ alloy (x being not less than 0 at. % and not more than 100 at. %, y being not less than 0 at. % and not more than 30 at. %) may be used. By using an amorphous alloy of $(Co_xFe_{100-x})_{100-y}B_y$ as the second pinned layer 110b, the variation between sensing elements can be suppressed even when the size of the sensing element is small.

The thickness of the second pinned layer 110b is preferably not less than 1.5 nm and not more than 5 nm, for example. Thereby, the strength of the unidirectional anisotropic magnetic field caused by the pinning layer 110a can be increased, for example. The strength of the antiferromagnetic coupling magnetic field between the second pinned layer 110b and the first pinned layer 110d can be increased via the magnetic coupling layer 110c formed on the second magnetization fixed layer, for example. The magnetic thickness (the product of the saturation magnetization Bs and the thickness t (Bs·t)) of the second pinned layer 110b is preferably substantially equal to the magnetic thickness of the first pinned layer 110d.

The saturation magnetization of $Co_{40}Fe_{40}B_{20}$ in a thin film form is approximately 1.9 T (tesla). When a $Co_{40}Fe_{40}B_{20}$ layer with a thickness of 3 nm is used as the first pinned layer 110d, the magnetic thickness of the first pinned layer 110d is 1.9 T×3 nm, which is 5.7 T nm, for example. On the other hand, the saturation magnetization of $Co_{75}Fe_{25}$ is approximately 2.1 T. The thickness of the second pinned layer 110b by which a magnetic thickness equal to the above is obtained is 5.7 Tnm/2.1 T, which is 2.7 nm. In this case, a $Co_{75}Fe_{25}$ layer with a thickness of approximately 2.7 nm is preferably used as the second pinned layer 110b. A $Co_{75}Fe_{25}$ layer with a thickness of 2.5 nm is used as the second pinned layer 110b, for example.

In the first sensing element 10u and the second sensing element 20u, a synthetic pin structure of the second magnetization fixed layer, the magnetic coupling layer 110c, and the first magnetization fixed layer is used. A single pin structure formed of one magnetization fixed layer may be used in the first sensing element 10u and the second sensing element 20u. In the case where a single pin structure is used, a $Co_{40}Fe_{40}B_{20}$ layer with a thickness of 3 nm is used as the magnetization fixed layer, for example. The same material as the material of the first magnetization fixed layer described above may be used as the ferromagnetic layer used as the magnetization fixed layer of the single pin structure.

The magnetic coupling layer 110c produces an antiferromagnetic coupling between the second magnetization fixed layer and the first magnetization fixed layer. The magnetic coupling layer 110c forms a synthetic pin structure. Ru is used as the magnetic coupling layer 110c, for example. The thickness of the magnetic coupling layer 110c is preferably not less than 0.8 nm and not more than 1 nm, for example. Other materials than Ru may be used as the magnetic coupling layer to the extent that they produce a sufficient antiferromagnetic coupling between the second magnetization fixed layer and the first magnetization fixed layer. The thickness of the magnetic coupling layer 110c may be set to a thickness of not less than 0.8 nm and not more than 1 nm. This thickness corresponds to the second peak (2nd peak) of the RKKY (Ruderman-Kittel-Kasuya-Yosida) coupling. The thickness of the magnetic coupling layer 110c may be set to a thickness of not less than 0.3 nm and not more than 0.6 nm. This thickness corresponds to the first peak (1st peak) of the RKKY coupling. Ru with a thickness of 0.9 nm is used as the magnetic coupling layer 110c, for example. Thereby, a highly reliable coupling is obtained more stably.

The magnetic layer used as the first magnetization fixed layer directly contributes to the MR effect. Co—Fe—B alloy is used as the first magnetization fixed layer, for example. Specifically, $(Co_xFe_{100-x})_{100-y}B_y$ alloy (x being not less than 0 at. % and not more than 100 at. %, y being not less than 0 at. % and not more than 30 at. %) may be used as the first magnetization fixed layer. When an amorphous alloy of $(Co_xFe_{100-x})_{100-y}B_y$ is used as the first magnetization fixed layer, the variation between elements due to crystal grains can be suppressed even when the size of the sensing element is small, for example.

A layer (for example, a tunnel insulating layer (not shown)) formed on the first magnetization fixed layer may be planarized. By the planarization of the tunnel insulating layer, the defect density of the tunnel insulating layer can be reduced. Thereby, a larger MR ratio is obtained with a lower resistance area. When MgO is used as the material of the tunnel insulating layer, an amorphous alloy of $(Co_xFe_{100-x})_{100-y}B_y$ may be used; thereby, the (100) orientation properties of the MgO layer formed on the tunnel insulating layer can be enhanced, for example. By enhancing the (100) orientation properties of the MgO layer, a larger MR ratio is obtained. The $(Co_xFe_{100-x})_{100-y}B_y$ alloy is crystallized during annealing, with the (100) plane of the MgO layer as a template. Thus, good crystal matching between the MgO and the $(Co_xFe_{100-x})_{100-y}B_y$ alloy is obtained. By obtaining good crystal matching, a larger MR ratio is obtained.

As the first magnetization fixed layer, Fe—Co alloy may be used as well as Co—Fe—B alloy, for example.

When the first magnetization fixed layer is thicker, a larger MR ratio is obtained. To obtain a larger fixed magnetic field, the first magnetization fixed layer is preferably thinner. Between the MR ratio and the fixed magnetic field, there is a trade-off in the thickness of the first magnetization fixed layer. When Co—Fe—B alloy is used as the first magnetization fixed layer, the thickness of the first magnetization fixed layer is preferably not less than 1.5 nm and not more than 5 nm. The thickness of the first magnetization fixed layer is more preferably not less than 2.0 nm and not more than 4 nm.

For the first magnetization fixed layer, $Co_{90}Fe_{10}$ alloy of the fcc structure, Co of the hcp structure, or a Co alloy of the hcp structure is used as well as the material described above. As the first magnetization fixed layer, at least one of Co, Fe, and Ni is used. As the first magnetization fixed layer, an alloy including at least one of these materials is used. As the first magnetization fixed layer, an FeCo alloy material of the bcc structure, a Co alloy with a cobalt content of 50 at. % or more, or a material with a Ni content of 50 at. % or more may be used, for example; thereby, a larger MR ratio is obtained. As the first magnetization fixed layer, also a Heusler magnetic alloy layer of $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, and the like may be used. As the first magnetization fixed layer, a $Co_{40}Fe_{40}B_{20}$ layer with a thickness of 3 nm is used, for example.

In this example, a synthetic pin structure composed of the second pinned layer 110b, the magnetic coupling layer 110c, and the first pinned layer 110d is used. Also a single pin structure may be used. When a single pin structure is used, the same material as the first pinned layer 110d of a synthetic pin layer may be used as the material of the pinned layer of the single pin structure.

The spacer layer 115 cuts the magnetic coupling between a first magnetization free layer and a second magnetization free layer. A metal, an insulator, or a semiconductor is used for the spacer layer 115. Cu, Au, Ag, or the like is used as the metal, for example. In the case where a metal is used as the spacer layer 115, the thickness of the spacer layer 115 is approximately not less than 1 nm and not more than 7 nm, for example. As the insulator or the semiconductor, a magnesium oxide (MgO etc.), an aluminum oxide ($Al_2O_3$ etc.), a titanium oxide (TiO etc.), a zinc oxide (ZnO etc.), gallium oxide (GaO), or the like is used, for example. In the case where an insulator or a semiconductor is used as the spacer layer 115, the thickness of the spacer layer 115 is approximately not less than 0.6 nm and not more than 2.5 nm, for example. A CCP (current-confined-path) spacer layer may be used as the spacer layer 115, for example. In the case where a CCP spacer layer is used as the spacer layer, a structure is used in which a copper (Cu) metal path is formed in an insulating layer of aluminum oxide ($Al_2O_3$), for example. An MgO layer with a thickness of 1.5 nm is used as the spacer layer 115, for example.

For the magnetization free layer, a ferromagnetic material is be used. A ferromagnetic material including Fe, Co, or Ni may be used for the magnetization free layer, for example. FeCo alloy, NiFe alloy, or the like is used as the material of the magnetization free layer, for example. Furthermore, Co—Fe—B alloy, Fe—Co—Si—B alloy, Fe—Ga alloy, Fe—Co—Ga alloy, a Tb-M-Fe alloy, a Tb-M1-Fe-M2 alloy, an Fe-M3-M4-B alloy, Ni, Fe—Al, a ferrite, or the like is used for the magnetization free layer. In the Tb-M-Fe alloy mentioned above, M is at least one selected from the group consisting of Sm, Eu, Gd, Dy, Ho, and Er. In the Tb-M1-Fe-M2 alloy mentioned above, M1 is at least one selected from the group consisting of Sm, Eu, Gd, Dy, Ho, and Er. M2 is at least one selected from the group consisting of Ti, Cr, Mn, Co, Cu, Nb, Mo, W, and Ta. In the Fe-M3-M4-B alloy mentioned above, M3 is at least one selected from the group consisting of Ti, Cr, Mn, Co, Cu, Nb, Mo, W, and Ta, M4 is at least one selected from the group consisting of Ce, Pr, Nd, Sm, Tb, Dy, and Er. As the ferrite mentioned above, $Fe_3O_4$, $(FeCo)_3O_4$, or the like is given. In these materials, the λs (magnetostriction constant) is large. The thickness of the magnetization free layer is 2 nm or more, for example.

A high gauge factor can be achieved by using a ferromagnetic material of an amorphous structure including boron as the magnetization free layer. Co—Fe—B alloy, Fe—B alloy, Fe—Co—Si—B alloy, and the like may be used, for example. For the magnetization free layer, an alloy including at least one element selected from Fe, Co, and Ni and boron (B) may be used. $Co_{40}Fe_{40}B_{20}$ with a thickness of 4 nm may be used, for example.

The magnetization free layer may have a multiple-layer structure. The magnetization free layer may have a two-layer structure, for example. In the case where a tunnel insulating layer of MgO is used as the spacer layer 115, it is preferable that a layer of Co—Fe—B alloy be provided on the interface in contact with the spacer layer 115. Thereby, a high magnetoresistance effect is obtained. In this case, Co—Fe—B/Fe—Co—Si—B alloy may be used, in which a layer of Co—Fe—B alloy is provided on the side in contact with the spacer layer 115 and Fe—Co—Si—B alloy is used on the opposite side to that, for example. The thickness of the $Co_{40}Fe_{40}B_{20}$ is 2 nm, for example. The thickness of the Fe—Co—Si—B is 4 nm, for example.

The cap layer 100 protects a layer provided under the cap layer 100. A plurality of metal layers are used as the cap layer 100, for example. A two-layer structure of a Ta layer and a Ru layer (Ta/Ru) is used as the cap layer 100, for example. The thickness of the Ta layer is 1 nm, for example, and the thickness of the Ru layer is 5 nm, for example. Other metal layers may be provided in place of the Ta layer and the Ru layer as the cap layer 100. The configuration of the cap layer 100 is arbitrary. A nonmagnetic material may be used, for example. Other materials may be used as the cap layer 100 to the extent that they can protect a layer provided under the cap layer 100. In the case of the first sensing element 10u on which the second sensing element 20u is continuously formed, the cap layer 100 exists as the interposition layer 100b that adjusts the distance between the first sensing element 10u and the second sensing element 20u. The cap layer 100 (the interposition layer 100b) of the first sensing element 10u may be omitted.

The interposition layer 100b magnetically divides the first sensing element 10u and the second sensing element 20u, for example. In the case where the upper electrode 60a and the lower electrode 60b described above are used to pass a current through the first sensing element 10u and the second sensing element 20u in the perpendicular-to-plane direction, the interposition layer 100b electrically connects the first sensing element 10u and the second sensing element 20u. A plurality of metal layers may be used as the interposition layer 100b, for example. A two-layer structure of a Ta layer and a Ru layer (Ta/Ru) is used as the interposition layer 100b, for example. The thickness of the Ta layer is 1 nm, for example, and the thickness of the Ru layer is 5 nm, for example. Other metal layers may be provided in place of the Ta layer and the Ru layer as the interposition layer 100b. The configuration of the interposition layer 100b is arbitrary. A nonmagnetic material may be used as the interposition layer 100b, for example. In the case where a shield layer 92b described later is provided, the interposition layer 100b may be regarded as the shield layer 92b. The interposition layer 100b may be omitted.

In FIG. 5, a current in the perpendicular-to-plane direction is passed through the first sensing element 10u and the second sensing element 20u using the upper electrode 60a and the lower electrode 60b as the first electrode and the second electrode, respectively, for example. In the embodiment, the first electrode and the second electrode may be arranged in the in-plane direction of the sensing element so that a current in the in-plane direction is passed through the first sensing element 10u and the second sensing element 20u. For all of the sensing elements described later, it is possible to design such that a current in the in-plane direction is passed through them.

Figure 6:
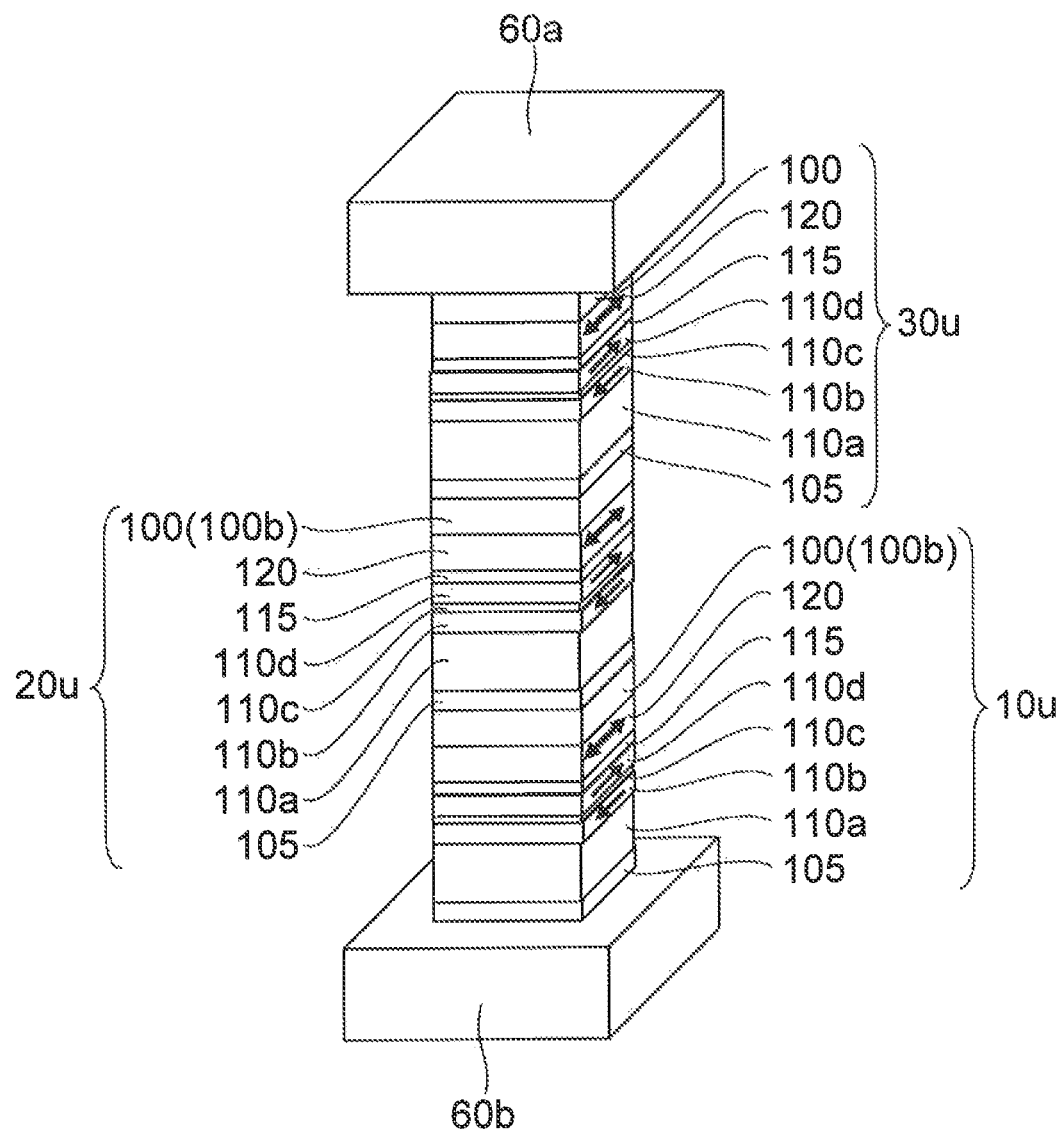
FIG. 6 is a schematic perspective view showing part of a strain sensing element according to the embodiment.

FIG. 6 is a schematic perspective view illustrating part of a strain sensing element according to the embodiment.

FIG. 6 illustrates the sensing unit 50. As shown in FIG. 6, the sensing element used in the embodiment includes the lower electrode 60b, the first sensing element 10u, the second sensing element 20u, a third sensing element 30u, and the upper electrode 60a that are sequentially aligned. In this example, the number of stacked sensing elements is three. Thus, in the embodiment, the number of stacked sensing elements may be three or more. The first sensing element 10u includes the underlayer 105, the pinning layer 110a, the second pinned layer 110b, the magnetic coupling layer 110c, the first pinned layer 110d, the spacer layer 115, the free layer 120, and the cap layer 100 (or the interposition layer 100b). The second sensing element 20u includes the underlayer 105, the pinning layer 110a, the second pinned layer 110b, the magnetic coupling layer 110c, the first pinned layer 110d, the spacer layer 115, the free layer 120, and the cap layer 100 (or the interposition layer 100b). The third sensing element 30u includes the underlayer 105, the pinning layer 110a, the second pinned layer 110b, the magnetic coupling layer 110c, the first pinned layer 110d, the spacer layer 115, the free layer 120, and the cap layer 100. In FIG. 5, each of the first sensing element 10u, the second sensing element 20u, and the third sensing element 30u includes a bottom spin valve structure having a synthetic pin layer. Similar materials to the sensing unit 50 of the example shown in FIG. 5 are used as the material of each layer included in the first sensing element 10u, the second sensing element 20u, and the third sensing element 30u. The material of each layer may be different between the first sensing element 10u, the second sensing element 20u, and the third sensing element 30u.

In the example shown in FIG. 6, in the first sensing element 10u, the first pinned layer 110d, the spacer layer 115, and the magnetization free layer 120 are provided. The first pinned layer 110d, the spacer layer 115, and the magnetization free layer 120 in the first sensing element 10u can be regarded as corresponding to the second magnetic layer 20, the first spacer layer 15, and the first magnetic layer 10 of the example shown in FIG. 1D, respectively. In the second sensing element 20u, the first pinned layer 110d, the spacer layer 115, and the magnetization free layer 120 are provided. The first pinned layer 110d, the spacer layer 115, and the magnetization free layer 120 in the second sensing element 20u can be regarded as corresponding to the fourth magnetic layer 40, the second spacer layer 35, and the third magnetic layer 30 of the example shown in FIG. 1D, respectively.

As the underlayer of the first sensing element 10u, Ta/Ru is used, for example. The thickness (the length in the Z-axis direction) of the Ta layer is 3 nm, for example. The thickness of the Ru layer is 2 nm, for example. As the pinning layer 110a, an IrMn layer with a thickness of 7 nm is used, for example. As the second magnetization fixed layer, a $Co_{75}Fe_{25}$ layer with a thickness of 2.5 nm is used, for example. As the magnetic coupling layer 110c, a Ru layer with a thickness of 0.9 nm is used, for example. As the first magnetization fixed layer, a $Co_{40}Fe_{40}B_{20}$ layer with a thickness of 3 nm is used, for example. As the spacer layer 115, an MgO layer with a thickness of 2.0 nm is used, for example. As the magnetization free layer, $Co_{40}Fe_{40}B_{20}$ with a thickness of 4 nm is used, for example. As the interposition layer 100b, Ta/Ru is used, for example. The thickness of the Ta layer is 2 nm, for example. The thickness of the Ru layer is 5 nm, for example.

As the underlayer 105 of the second sensing element 20u, Ta/Ru is used, for example. The thickness (the length in the Z-axis direction) of the Ta layer is 3 nm, for example. The thickness of the Ru layer is 2 nm, for example. As the pinning layer 110a, an IrMn layer with a thickness of 7 nm is used, for example. As the second magnetization fixed layer, a $Co_{75}Fe_{25}$ layer with a thickness of 2.5 nm is used, for example. As the magnetic coupling layer 110c, a Ru layer with a thickness of 0.9 nm is used, for example. As the first magnetization fixed layer, a $Co_{40}Fe_{40}B_{20}$ layer with a thickness of 3 nm is used, for example. As the spacer layer 115, an MgO layer with a thickness of 2.0 nm is used, for example. As the magnetization free layer, $Co_{40}Fe_{40}B_{20}$ with a thickness of 4 nm is used, for example. As the interposition layer 100b, Ta/Ru is used, for example. The thickness of the Ta layer is 2 nm, for example. The thickness of the Ru layer is 15 nm, for example.

As the underlayer 105 of the third sensing element 30u, Ta/Ru is used, for example. The thickness (the length in the Z-axis direction) of the Ta layer is 3 nm, for example. The thickness of the Ru layer is 2 nm, for example. As the pinning layer 110a, an IrMn layer with a thickness of 7 nm is used, for example. As the second magnetization fixed layer, a $Co_{75}Fe_{25}$ layer with a thickness of 2.5 nm is used, for example. As the magnetic coupling layer 110c, a Ru layer with a thickness of 0.9 nm is used, for example. As the first magnetization fixed layer, a $Co_{40}Fe_{40}B_{20}$ layer with a thickness of 3 nm is used, for example. As the spacer layer 115, an MgO layer with a thickness of 2.0 nm is used, for example. As the magnetization free layer, $Co_{40}Fe_{40}B_{20}$ with a thickness of 4 nm is used, for example. As the cap layer 100, Ta/Ru is used, for example.

The thickness of the Ta layer is 2 nm, for example. The thickness of the Ru layer is 5 nm, for example.

Figure 7:
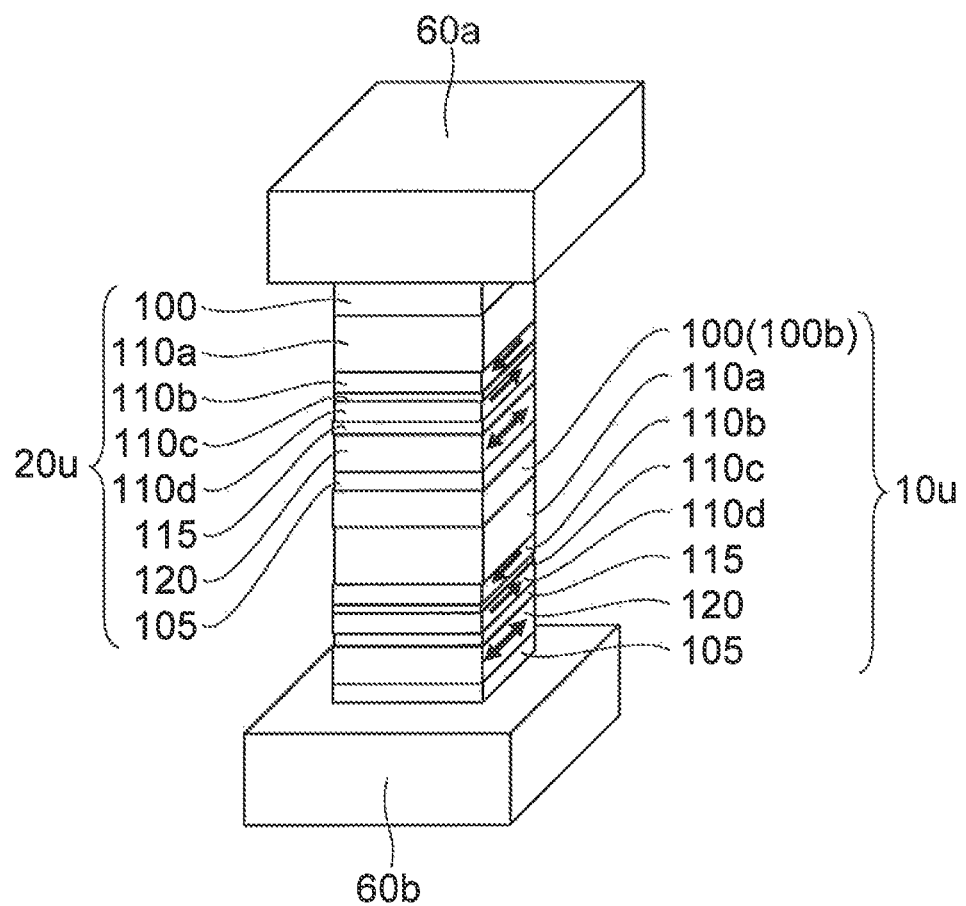
FIG. 7 is a schematic perspective view showing part of a strain sensing element according to the embodiment.

FIG. 7 is a schematic perspective view illustrating part of a strain sensing element according to the embodiment.

FIG. 7 illustrates the sensing unit 50. As shown in FIG. 7, the sensing element used in the embodiment includes the lower electrode 60b, the first sensing element 10u, the second sensing element 20u, and the upper electrode 60a that are sequentially aligned. The first sensing element 10u includes the underlayer 105, the free layer 120, the spacer layer 115, the first pinned layer 110d, the magnetic coupling layer 110c, the second pinned layer 110b, the pinning layer 110a, and the cap layer 100 (or the interposition layer 100b). The second sensing element 20u includes the underlayer 105, the free layer 120, the spacer layer 115, the first pinned layer 110d, the magnetic coupling layer 110c, the second pinned layer 110b, the pinning layer 110a, and the cap layer 100. In the example shown in FIG. 7, each of the first sensing element 10u and the second sensing element 20u includes a top spin valve structure including a synthetic pin layer. Similar materials to the sensing unit 50 of the embodiment shown in FIG. 5 are used as the material of each layer in the first sensing element 10u and the second sensing element 20u. The material of each layer may be different between the first sensing element 10u and the second sensing element 20u.

In the example shown in FIG. 7, in the first sensing element 10u, the free layer 120, the spacer layer 115, and the first pinned layer 110d are provided. The free layer 120, the spacer layer 115, and the first pinned layer 110d in the first sensing element 10u correspond to the first magnetic layer 10, the first spacer layer 15, and the second magnetic layer 20 of the example shown in FIG. 1C, respectively. In the second sensing element 20u, the free layer 120, the spacer layer 115, and the first pinned layer 110d are provided. The free layer 120, the spacer layer 115, and the first pinned layer 110d in the second sensing element 20u correspond to the third magnetic layer 30, the second spacer layer 35, and the fourth magnetic layer 40 of the example shown in FIG. 1C, respectively.

As the underlayer 105 of the first sensing element 10u, Ta/Cu is used, for example. The thickness (the length in the Z-axis direction) of the Ta layer is 3 nm, for example. The thickness of the Cu layer is 5 nm, for example. As the free layer 120, $Co_{40}Fe_{40}B_{20}$ with a thickness of 4 nm is used, for example. As the spacer layer 115, an MgO layer with a thickness of 2.0 nm is used, for example. As the first pinned layer 110d, $Co_{40}Fe_{40}B_{20}/Fe_{50}Co_{50}$ is used, for example. The thickness of the $Co_{40}Fe_{40}B_{20}$ layer is 2 nm, for example, and the thickness of the $Fe_{50}Co_{50}$ layer is 1 nm, for example. As the magnetic coupling layer 110c, a Ru layer with a thickness of 0.9 nm is used, for example. As the second pinned layer 110b, a $Co_{75}Fe_{25}$ layer with a thickness of 2.5 nm is used, for example. As the pinning layer 110a, an IrMn layer with a thickness of 7 nm is used, for example. As the interposition layer 100b, Ta/Ru is used, for example. The thickness of the Ta layer is 2 nm, for example. The thickness of the Ru layer is 5 nm, for example.

As the underlayer 105 of the second sensing element 20u, Ta/Cu is used, for example. The thickness (the length in the Z-axis direction) of the Ta layer is 3 nm, for example. The thickness of the Cu layer is 5 nm, for example. As the free layer 120, $Co_{40}Fe_{40}B_{20}$ with a thickness of 4 nm is used, for example. As the spacer layer 115, an MgO layer with a thickness of 2.0 nm is used, for example. As the first pinned layer 110d, $Co_{40}Fe_{40}B_{20}/Fe_{50}Co_{50}$ is used, for example. The thickness of the $Co_{40}Fe_{40}B_{20}$ layer is 2 nm, for example. The thickness of the $Fe_{50}Co_{50}$ layer is 1 nm, for example. As the magnetic coupling layer 110c, a Ru layer is used, for example. The thickness of the Ru layer is 0.9 nm, for example. As the second pinned layer 110b, a $Co_{75}Fe_{25}$ layer is used, for example. The thickness of the $Co_{75}Fe_{25}$ layer is 2.5 nm, for example. As the pinning layer 110a, an IrMn layer is used, for example. The thickness of the IrMn layer is 7 nm, for example. As the cap layer 100, Ta/Ru is used, for example. The thickness of the Ta layer is 2 nm, for example. The thickness of the Ru layer is 15 nm, for example.

Figure 8:
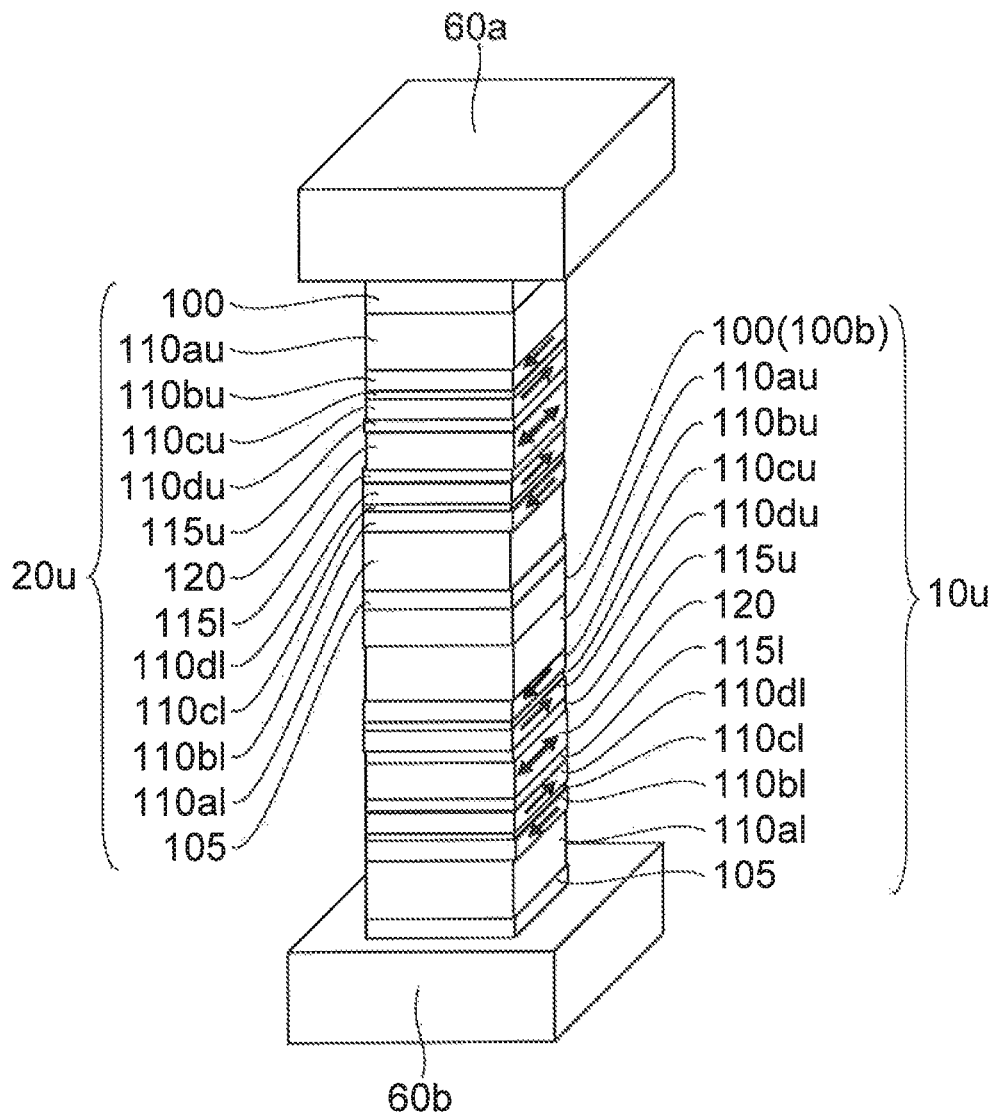
FIG. 8 is a schematic perspective view showing part of a strain sensing element according to the embodiment.

FIG. 8 is a schematic perspective view illustrating part of a strain sensing element according to the embodiment.

FIG. 8 illustrates the sensing unit 50. As shown in FIG. 8, the sensing element used in the embodiment includes the lower electrode 60b, the first sensing element 10u, the second sensing element 20u, and the upper electrode 60a that are sequentially aligned. The first sensing element 10u includes the underlayer 105, a lower pinning layer 110al, a lower second pinned layer 110bl, a lower magnetic coupling layer 110cl, a lower first pinned layer 110dl, a lower spacer layer 115l, the free layer 120, an upper spacer layer 115u, an upper first pinned layer 110du, an upper magnetic coupling layer 110cu, an upper second pinned layer 110bu, an upper pinning layer 110au, and the cap layer 100 (or the interposition layer 100b). The second sensing element 20u includes the underlayer 105, the lower pinning layer 110al, the lower second pinned layer 110bl, the lower magnetic coupling layer 110cl, the lower first pinned layer 110dl, the lower spacer layer 115l, the free layer 120, the upper spacer layer 115u, the upper first pinned layer 110du, the upper magnetic coupling layer 110cu, the upper second pinned layer 110bu, the upper pinning layer 110au, and the cap layer 100. In the example shown in FIG. 8, each of the first sensing element 10u and the second sensing element 20u includes a dual spin valve structure including a synthetic pin layer. Similar materials to the sensing unit 50 of the example shown in FIG. 5 are used as the material of each layer in the first sensing element 10u and the second sensing element 20u. The material of each layer may be different between the first sensing element 10u and the second sensing element 20u.

In the example shown in FIG. 8, in the first sensing element 10u, the lower first pinned layer 110dl, the spacer layer 115l, and the free layer 120 are provided. The lower first pinned layer 110dl, the spacer layer 115l, and the free layer 120 of the first sensing element 10u can be regarded as corresponding to the second magnetic layer 20, the first spacer layer 15, and the first magnetic layer 10 of the example shown in FIG. 1C, respectively. In the second sensing element 20u, the lower first pinned layer 110dl, the spacer layer 115l, and the free layer 120 are provided. The lower first pinned layer 110dl, the spacer layer 115l, and the free layer 120 of the second sensing element 20u can be regarded as corresponding to the fourth magnetic layer 40, the second spacer layer 35, and the third magnetic layer 30 of the example shown in FIG. 1C, respectively.

As the underlayer 105 of the first sensing element 10u, Ta/Ru is used, for example. The thickness (the length in the Z-axis direction) of the Ta layer is 3 nm, for example. The thickness of the Ru layer is 2 nm, for example. As the lower pinning layer 110al, an IrMn layer is used, for example. The thickness of the IrMn layer is 7 nm, for example. As the lower second pinned layer 110bl, a $Co_{75}Fe_{25}$ layer is used, for example. The thickness of the $Co_{75}Fe_{25}$ layer is 2.5 nm, for example. As the lower magnetic coupling layer 110cl, a Ru layer with a thickness of 0.9 nm is used, for example. As the lower first pinned layer 110dl, a $Co_{40}Fe_{40}B_{20}$ layer with a thickness of 3 nm is used, for example. As the lower spacer layer 115l, an MgO layer with a thickness of 2.0 nm is used, for example. As the free layer 120, $Co_{40}Fe_{40}B_{20}$ with a thickness of 4 nm is used, for example. As the upper spacer layer 115u, an MgO layer with a thickness of 2.0 nm is used, for example. As the upper first pinned layer 110du, $Co_{40}Fe_{40}B_{20}$/$Fe_{50}Co_{50}$ is used, for example. The thickness of the $Co_{40}Fe_{40}B_{20}$ layer is 2 nm, for example. The thickness of the $Fe_{50}Co_{50}$ layer is 1 nm, for example. As the upper magnetic coupling layer 110cu, a Ru layer with a thickness of 0.9 nm is used, for example. As the upper second pinned layer 110bu, a $Co_{75}Fe_{25}$ layer with a thickness of 2.5 nm is used, for example. As the upper pinning layer 110au, an IrMn layer with a thickness of 7 nm is used, for example. As the interposition layer 100b, Ta/Ru is used, for example. The thickness of the Ta layer is 2 nm, for example. The thickness of the Ru layer is 5 nm, for example.

As the underlayer 105 of the second sensing element 20u, Ta/Ru is used, for example. The thickness (the length in the Z-axis direction) of the Ta layer is 3 nm, for example. The thickness of the Ru layer is 2 nm, for example. As the lower pinning layer 110al, an IrMn layer with a thickness of 7 nm is used, for example. As the lower second pinned layer 110bl, a $Co_{75}Fe_{25}$ layer with a thickness of 2.5 nm is used, for example. As the lower magnetic coupling layer 110cl, a Ru layer with a thickness of 0.9 nm is used, for example. As the lower first pinned layer 110dl, a $Co_{40}Fe_{40}O_{20}$ layer with a thickness of 3 nm is used, for example. As the lower spacer layer 115l, an MgO layer with a thickness of 2.0 nm is used, for example. As the free layer 120, $Co_{40}Fe_{40}B_{20}$ with a thickness of 4 nm is used, for example. As the upper spacer layer 115u, an MgO layer with a thickness of 2.0 nm is used, for example. As the upper first pinned layer 110du, $Co_{40}Fe_{40}B_{20}$/$Fe_{50}Co_{50}$ is used, for example. The thickness of the $Co_{40}Fe_{40}B_{20}$ layer is 2 nm, for example. The thickness of the $Fe_{50}Co_{50}$ layer is 1 nm, for example. As the upper magnetic coupling layer 110cu, a Ru layer with a thickness of 0.9 nm is used, for example. As the upper second pinned layer 110bu, a $Co_{75}Fe_{25}$ layer with a thickness of 2.5 nm is used, for example. As the upper pinning layer 110au, an IrMn layer with a thickness of 7 nm is used, for example. As the cap layer 100, Ta/Ru is used, for example. The thickness of the Ta layer is 2 nm, for example. The thickness of the Ru layer is 5 nm, for example.

The sensing elements illustrated in FIG. 5 to FIG. 8 are sensing elements of a type including a pinned layer adjacent to a pinning layer. In the sensing element including such a pinned layer, the advantage of using the configuration of the sensing unit 50 in which a plurality of sensing elements are stacked in the stacking direction is particularly great. As shown in FIG. 2A to FIG. 2I, in the sensing element using the pinned layer (the second magnetic layer 20), the resulting output varies depending on the direction of the strain applied to the pinned layer (the second magnetic layer 20). In the case where a plurality of sensing elements by which similar electric resistance changes (for example, polarities etc.) with respect to the strain are obtained are arranged on the film unit 70d, the plurality of sensing elements are arranged in a region on the film unit 70d where similar anisotropic strains are generated. Therefore, the restriction on the arrangement position in the plane will be great. For the sensing element including such a pinned layer, a larger number of sensing elements can be arranged in the element arrangeable region in the plane by stacking a plurality of sensing elements. Thus, the advantage of using the configuration in which a plurality of sensing elements are stacked in the perpendicular-to-plane direction is great.

FIG. 9A to FIG. 9C are schematic perspective views illustrating parts of strain sensing elements according to the embodiment.

FIG. 9A illustrates the sensing unit 50. As shown in FIG. 9A, the sensing element used in the embodiment includes the lower electrode 60b, the first sensing element 10u, the second sensing element 20u, and the upper electrode 60a that are sequentially aligned. The first sensing element 10u includes the underlayer 105, a lower free layer 120l, the spacer layer 115, an upper free layer 120u, and the cap layer 100 (or the interposition layer 100b). The second sensing element 20u includes the underlayer 105, the lower free layer 120l, the spacer layer 115, the upper free layer 120u, and the cap layer 100.

In the example shown in FIG. 9, each of the first sensing element 10u and the second sensing element 20u includes a spin valve structure of a two free layer type. Similar materials to the sensing unit 50 of the example shown in FIG. 5 are used as the material of each layer in the first sensing element 10u and the second sensing element 20u. The material of each layer may be different between the first sensing element 10u and the second sensing element 20u.

In the example shown in FIG. 9A, in the first sensing element 10u, the lower free layer 120l, the spacer layer 115, and the upper free layer 120u are provided. The lower free layer 120l, the spacer layer 115, and the upper free layer 120u in the first sensing element 10u correspond to the first magnetic layer 10, the first spacer layer 15, and the second magnetic layer 20 of the example shown in FIG. 10, respectively. In the second sensing element 20u, the lower free layer 120l, the spacer layer 115, and the upper free layer 120u are provided. The lower free layer 120l, the spacer layer 115, and the upper free layer 120u in the second sensing element 20u correspond to the third magnetic layer 30, the second spacer layer 35, and the fourth magnetic layer 40 of the example shown in FIG. 1B, respectively.

As the underlayer 105 of the first sensing element 10u, Ta/Cu is used, for example. The thickness (the length in the Z-axis direction) of the Ta layer is 3 nm, for example. The thickness of the Cu layer is 5 nm, for example. As the lower free layer 120l, $Co_{40}Fe_{40}B_{20}$ with a thickness of 4 nm is used, for example. As the spacer layer 115, an MgO layer with a thickness of 2.0 nm is used, for example. As the upper free layer 120u, $Co_{40}Fe_{40}B_{20}$ with a thickness of 4 nm is used, for example. As the interposition layer 100b, Cu/Ta/Ru is used, for example. The thickness of the Cu layer is 5 nm, for example. The thickness of the Ta layer is 2 nm, for example. The thickness of the Ru layer is 5 nm, for example.

As the underlayer 105 of the second sensing element 20u, Ta/Cu is used, for example. The thickness (the length in the Z-axis direction) of the Ta layer is 3 nm, for example. The thickness of the Cu layer is 5 nm, for example. As the lower free layer 120l, $Co_{40}Fe_{40}B_{20}$ with a thickness of 4 nm is used, for example. As the spacer layer 115, an MgO layer with a thickness of 2.0 nm is used, for example. As the upper free layer 120u, $Co_{40}Fe_{40}B_{20}$ with a thickness of 4 nm is used, for example. As the cap layer 100, Cu/Ta/Ru is used, for example. The thickness of the Cu layer is 5 nm, for example. The thickness of the Ta layer is 2 nm, for example. The thickness of the Ru layer is 5 nm, for example.

FIG. 9B illustrates the sensing unit 50. As shown in FIG. 9B, the sensing element used in the embodiment includes the lower electrode 60b, the first sensing element 10u, the second sensing element 20u, and the upper electrode 60a that are sequentially aligned. The first sensing element 10u includes the underlayer 105, a first free layer 120a, a first spacer layer 115a, a second free layer 120b, and a third spacer layer 115c. The second sensing element 20u includes a third free layer 120c, a second spacer layer 115b, a fourth free layer 120d, and the cap layer 100.

In the example shown in FIG. 9B, the third spacer layer 115c is disposed between the second magnetization free layer (the second free layer 120b) of the first sensing element 10u and a third magnetization free layer (the third free layer 120c) of the second sensing element 20u. Similar materials to the sensing unit 50 of the example shown in FIG. 5 are used as the material of each layer in the first sensing element 10u and the second sensing element 20u. The material of each layer may be different between the first sensing element 10u and the second sensing element 20u.

In the example shown in FIG. 9B, in the first sensing element 10u, the first free layer 120a, the spacer layer 115a, and the second free layer 120b are provided. The first free layer 120a, the spacer layer 115a, and the second free layer 120b in the first sensing element 10u correspond to the first magnetic layer 10, the first spacer layer 15, and the second magnetic layer 20 of the example shown in FIG. 1B, respectively. In the second sensing element 20u, the third free layer 120c, the spacer layer 115b, and the fourth free layer 120d are provided. The third free layer 120c, the spacer layer 115b, and the fourth free layer 120d in the second sensing element 20u correspond to the third magnetic layer 30, the second spacer layer 35, and the fourth magnetic layer 40 of the example shown in FIG. 1B, respectively.

As the underlayer 105 of the first sensing element 10u, Ta/Cu is used, for example. The thickness (the length in the Z-axis direction) of the Ta layer is 3 nm, for example. The thickness of the Cu layer is 5 nm, for example. As the first free layer, $Co_{40}Fe_{40}B_{20}$ with a thickness of 4 nm is used, for example. As the spacer layer 115a, an MgO layer with a thickness of 2.0 nm is used, for example. As the second free layer 120b, $Co_{40}Fe_{40}B_{20}$ with a thickness of 4 nm is used, for example. As the third spacer layer 115c, an MgO layer with a thickness of 2.0 nm is used, for example.

As the third free layer 120c of the second sensing element 20u, $Co_{40}Fe_{40}B_{20}$ with a thickness of 4 nm is used, for example. As the spacer layer 115b, an MgO layer with a thickness of 2.0 nm is used, for example. As the fourth free layer 120d, $Co_{40}Fe_{40}B_{20}$ with a thickness of 4 nm is used, for example. As the cap layer 100, Cu/Ta/Ru is used, for example. The thickness of the Cu layer is 5 nm, for example. The thickness of the Ta layer is 2 nm, for example. The thickness of the Ru layer is 5 nm, for example.

FIG. 9C illustrates the sensing unit 50. As shown in FIG. 9C, the sensing element used in the embodiment includes the lower electrode 60b, the underlayer 105, the first free layer 120a, the first spacer layer 115a, the second free layer 120b, the third spacer layer 115c, the third free layer 120c, the cap layer 100, and the upper electrode 60b that are sequentially aligned.

Figure 10A:
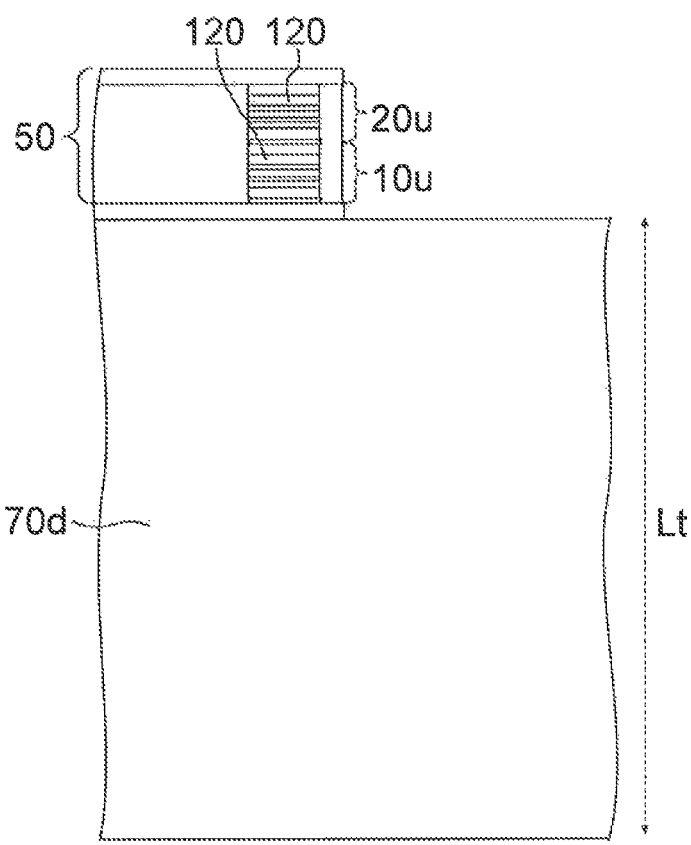
FIG. 10A and FIG. 10B are schematic cross-sectional views showing a strain sensing element according to the embodiment.

FIG. 10A and FIG. 103 are schematic cross-sectional views illustrating a strain sensing element according to the embodiment.

Figure 10B:
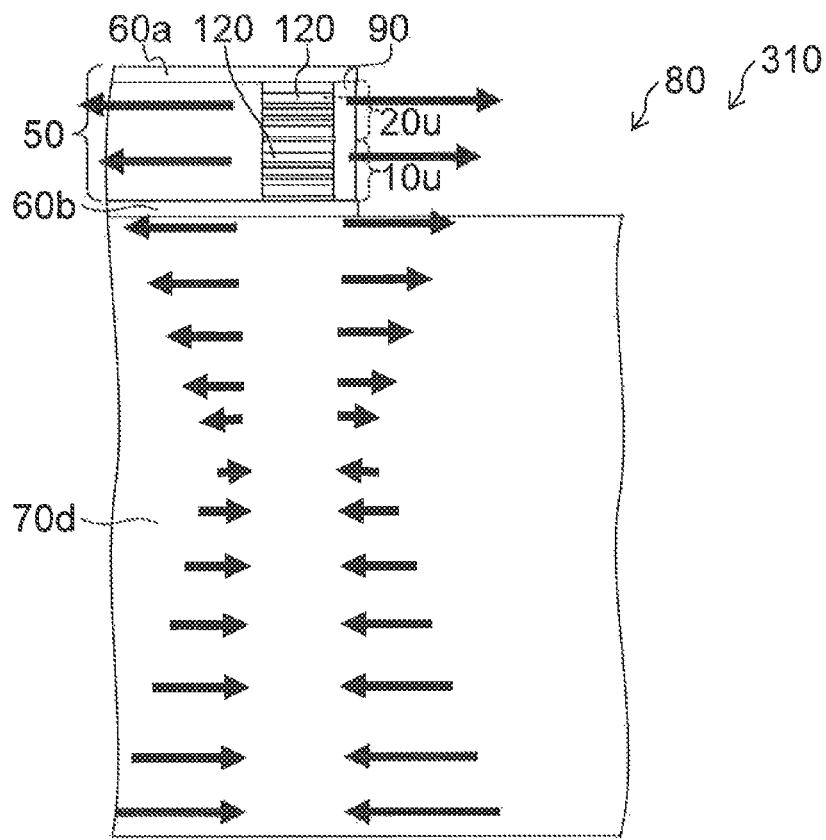

FIG. 10A is a schematic cross-sectional view of the film unit 70d and the sensing unit 50. FIG. 10B is a schematic cross-sectional view illustrating bending of the film unit 70d and the sensing unit 50d. In the embodiment, there is an appropriate relationship between the thickness of the film unit 70d and the thickness of the sensing unit 50. The film unit 70d and the sensing unit 50 bend due to an external pressure together with each other, and therefore bend due to an external pressure as an integrated structure body. When a plate-like structure body bends, one surface becomes a convex shape and a tensile strain occurs, and the other surface becomes a concave shape and a compressive strain occurs. The center and its vicinity in the thickness direction of the structure body have no strain. Therefore, the range in which similar anisotropic strains are obtained decreases from the surface toward the interior of the structure body in the thickness direction. If the distance in the thickness direction between sensing elements included in the sensing unit 50 is too large, the difference in the magnitude of the applied strain is increased between the lower sensing element and the upper sensing element, and this is not preferable. When the distance between the lower sensing element and the upper sensing element is small, the values of the strains applied to the sensing elements are close.

What senses the strain in the sensing element is the magnetization free layer, for example. Therefore, the position of the magnetization free layer in the sensing unit 50 influences the characteristics of the sensing element. It is preferable that the distance between the magnetization free layer of the first sensing element 10u (the first magnetic layer 10) and the magnetization free layer of the second sensing element 20u (the third magnetic layer 30) be smaller than ⅕ of the thickness in the Z-axis direction of the film unit 70d, for example. It is preferable that the distance between the fourth magnetic layer 40 and the second magnetic layer 20 be not more than ⅕ of the thickness of the film unit 70d along the Z-axis direction, for example.

Figure 11:
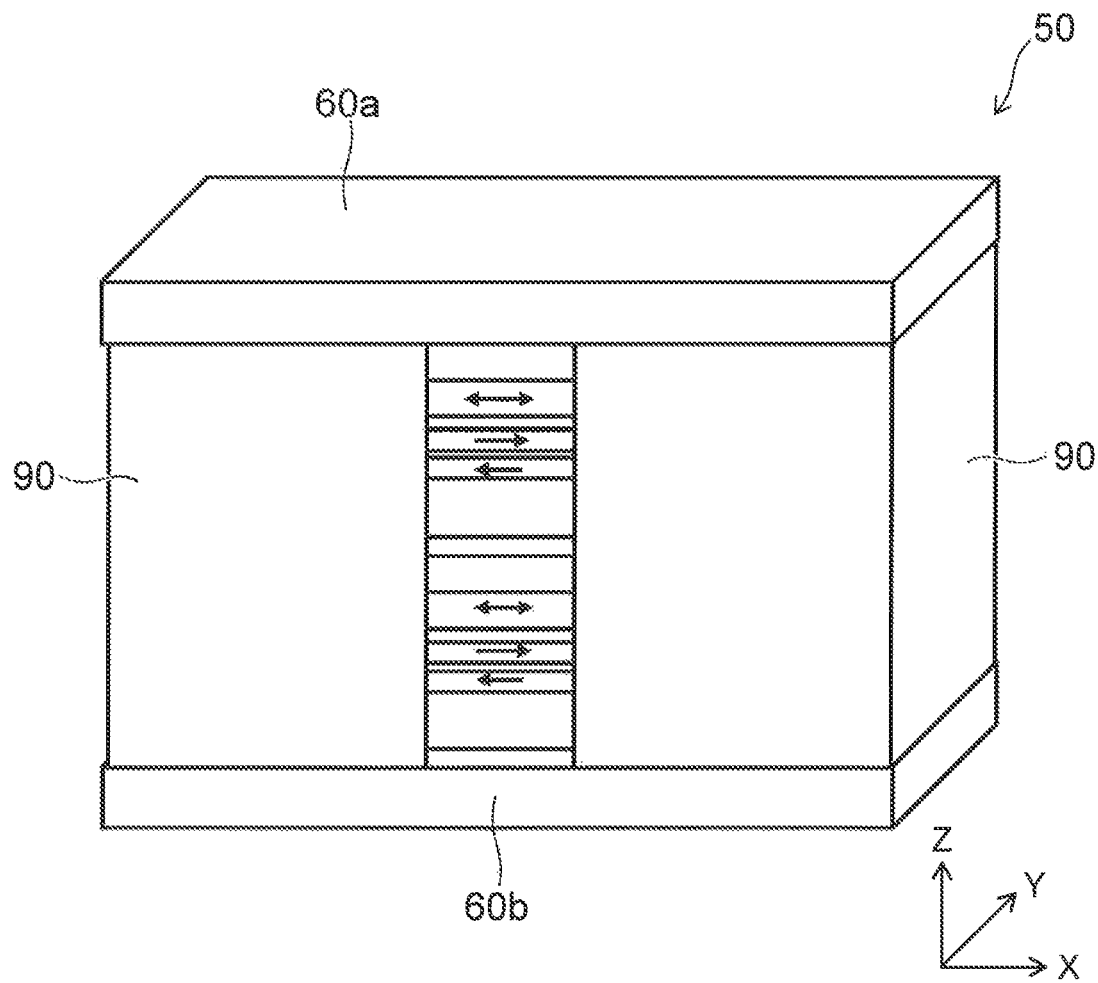
FIG. 11 is a schematic perspective view showing part of a strain sensing element according to the embodiment.

FIG. 11 is a schematic perspective view illustrating part of a strain sensing element according to the embodiment.

FIG. 11 illustrates another sensing unit 50. As illustrated in FIG. 11, an insulating layer 90 is provided in the sensing unit 50. Two insulating layers 90 (insulating portions) apart from each other are provided between the lower electrode 60b and the upper electrode 60a, for example. Sensing elements (the first sensing element 10u, the second sensing element 20u, etc.) are arranged between the two insulating layers 90. The sensing elements are arranged between the lower electrode 60b and the upper electrode 60a. The insulating layer 90 is provided to oppose the side wall of the sensing element.

For the insulating layer 90, an aluminum oxide (for example, $Al_2O_3$), a silicon oxide (for example, $SiO_2$), or the like may be used, for example. Leakage current around the stacked body can be suppressed by the insulating layer 90.

Figure 12A:
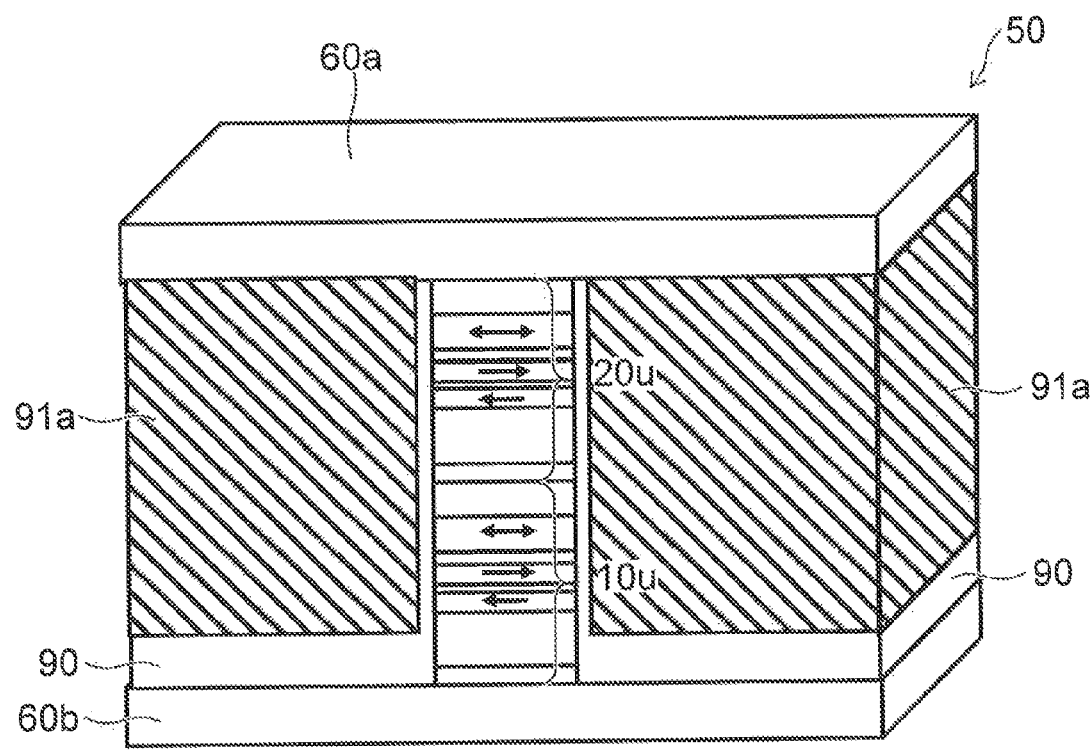
FIG. 12A and FIG. 12B are schematic perspective views showing parts of strain sensing elements according to the embodiment.
Figure 12B:
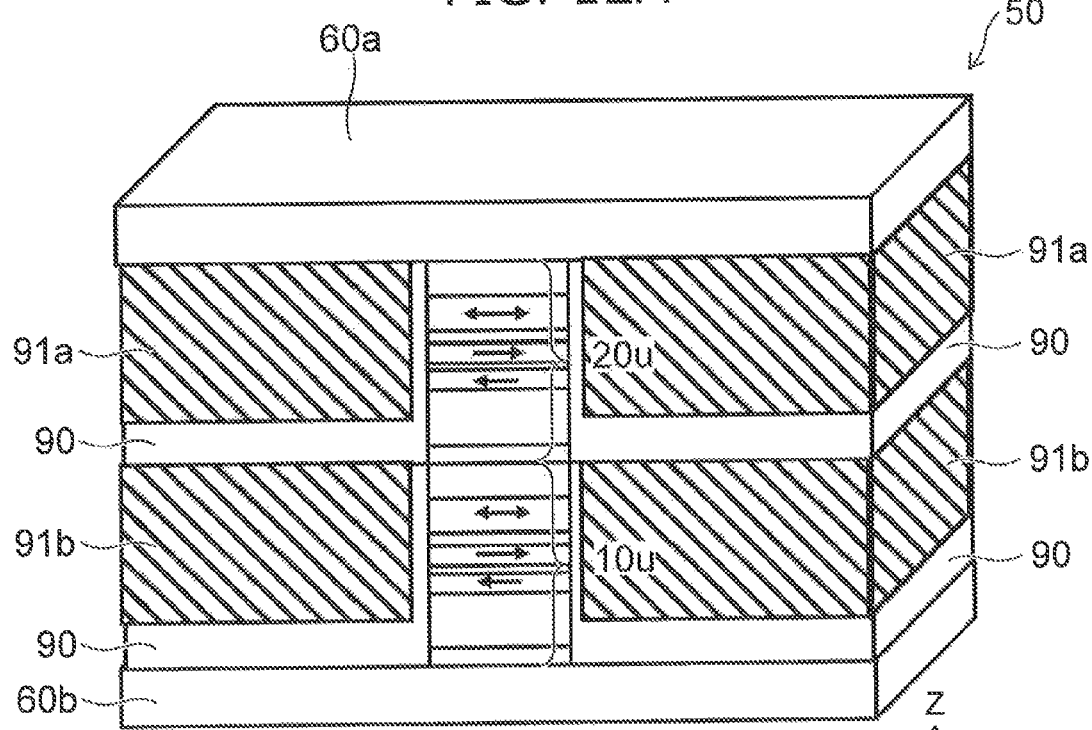

FIG. 12A and FIG. 12B are schematic perspective views illustrating parts of strain sensing elements according to the embodiment.

FIG. 12A illustrates another sensing element. As illustrated in FIG. 12A, a first hard bias layer 91a is further provided in the sensing unit 50 of this example. That is, the first hard bias layer 91a (a hard bias portion) is provided side by side with the sensing unit 50 between the lower electrode 60b and the upper electrode 60a. Two first hard bias layers 91a (hard bias portions) apart from each other are provided between the lower electrode 60b and the upper electrode 60a, for example. Sensing elements (the first sensing element 10u, the second sensing element 20u, etc.) are arranged between the two first hard bias layers 91a. The insulating layer 90 is disposed between the first hard bias layer 91a and the sensing element. In this example, the insulating layer 90 extends between the first hard bias layer 91a and the lower electrode 60b. Thus, the sensing unit 50 includes the first hard bias layer 91a. The first hard bias layer 91a is apart from the second sensing element 20u in a direction crossing the first direction crossing the film surface 70fs, for example.

In this example, the first hard bias layer 91a is also apart from the first sensing element 10u in a second direction.

The first hard bias layer 91a uses its magnetization to set at least one of the magnetization of the first magnetic layer 10 and the magnetization of the second magnetic layer 20 to a desired direction, for example. The first hard bias layer 91a uses its magnetization to set at least one of the magnetization of the third magnetic layer 30 and the magnetization of the fourth magnetic layer 40 to a desired direction.

For the first hard bias layer 91a, a hard ferromagnetic material with a relatively high magnetic anisotropy such as CoPt, CoCrPt, and FePt is used, for example. As the first hard bias layer 91a, a structure in which a layer of a soft magnetic material such as FeCo and Fe and an antiferromagnetic layer are stacked may be used. In this case, the magnetization runs along a prescribed direction due to an exchange coupling. The thickness (the length along the direction from the lower electrode 60b toward the upper electrode 60a) of the hard bias layer 91a is not less than 5 nm and not more than 50 nm, for example.

In FIG. 12B, a plurality of hard bias layers (the first hard bias layer 91a and a second hard bias layer 91b) are aligned in the stacking direction (the Z-axis direction). A bias strength to the sensing element by the hard bias layer can be produced also by adjusting the thickness of the hard bias layer.

By providing a hard bias layer opposite to the side wall of each sensing element, the thickness of the hard bias layer can be adjusted in accordance with an appropriate bias strength for each sensing element, for example.

Thus, the sensing unit 50 includes the first hard bias layer 91a aligned with the second sensing element 20u in the second direction crossing the first direction crossing the film surface 70fs. The first hard bias layer 91a is apart from the second sensing element 20u in the second direction, for example. The sensing unit 50 may further include the second hard bias layer 91b aligned with the first sensing element 10u in the second direction. The second hard bias layer 91b is apart from the first sensing element 10u in the second direction, for example.

Figure 13A:
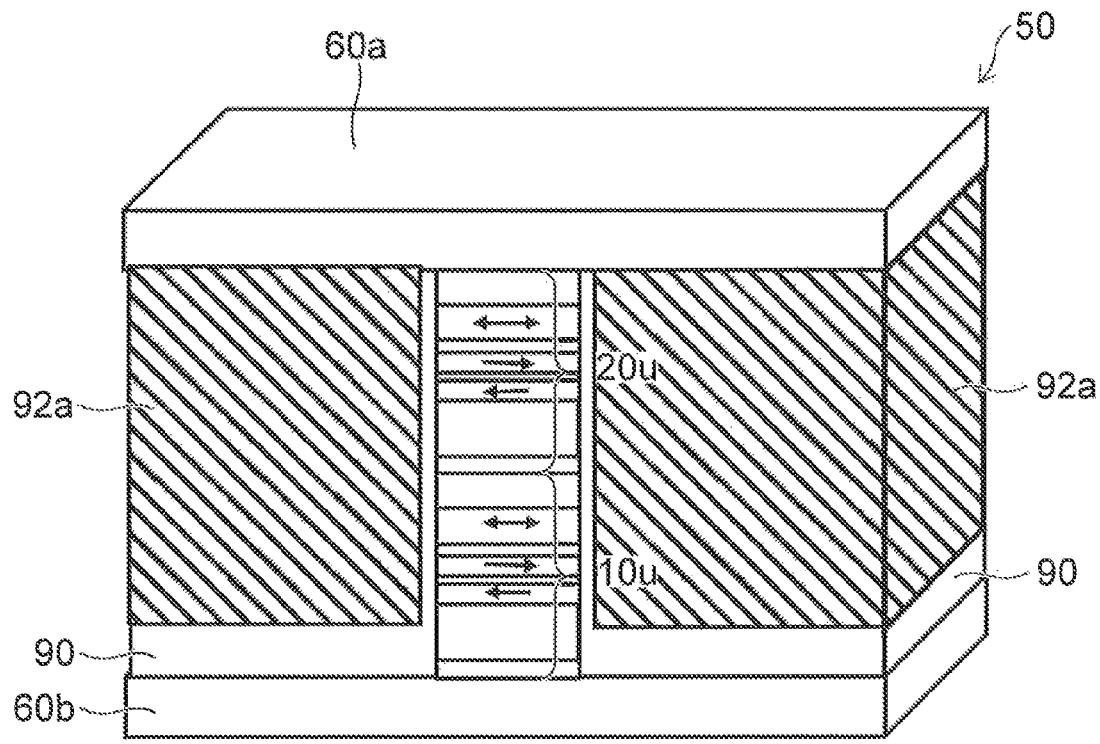
FIG. 13A and FIG. 13B are schematic views showing parts of strain sensing elements according to the embodiment.
Figure 13B:
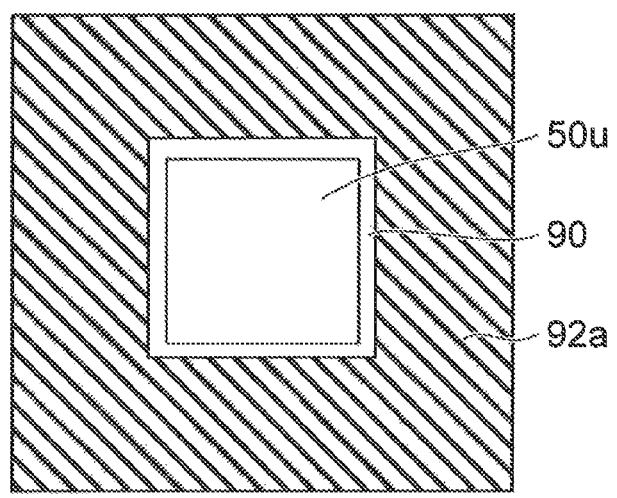

FIG. 13A and FIG. 13B are schematic views illustrating parts of strain sensing elements according to the embodiment.

FIG. 13A illustrates another sensing unit, FIG. 13B is a plan view. As illustrated in FIG. 13A, a shield layer 92a (a first shield layer) is further provided in the sensing element. The shield layer 92a is provided side by side with the sensing element between the lower electrode 60b and the upper electrode 60a, for example. Two shield layers 92a apart from each other are provided between the lower electrode 60b and the upper electrode 60a, and sensing elements are arranged between the two shield layers 92a, for example. The insulating layer 90 is disposed between the shield layer 92a and the sensing element. In this example, the insulating layer 90 extends between the shield layer 92a and the lower electrode 60b.

Thus, in the embodiment, the sensing unit 50 may include the shield layer 92a. The shield layer 92a is apart from the second sensing element 20u in the second direction crossing the first direction crossing the film surface 70fs, for example. The shield layer 92a may also be apart from the first sensing element 10u in the second direction mentioned above. The sensing unit 50 may further include the first shield layer (the shield layer 92a) apart from the first sensing element 10u in the second direction crossing the first direction.

The shield layer 92a directs the stray magnetic fields from the magnetic layers of the plurality of sensing elements to the shield layer 92a side, for example. The shield layer 92a suppresses the magnetic interference due to the stray magnetic field between sensing elements arranged in the stacking direction, for example.

For the shield layer 92a, a soft ferromagnetic material with a relatively high magnetic permeability such as NiFe is used, for example. The thickness (the length along the direction from the lower electrode 60b toward the upper electrode 60a) of the shield layer 92a is not less than 5 nm and not more than 50 nm, for example.

FIG. 13B is a plan view of a sensing element 50u as viewed from above, for example. As shown in FIG. 13B, the shield layer 92a is disposed so as to surround the sensing element 50u, for example. By disposing the shield layer 92a in this way, the stray magnetic field can be released to the shield layer 92a side even when the directions of the magnetic layers of the sensing element 50u are directed to any directions.

Figure 14:
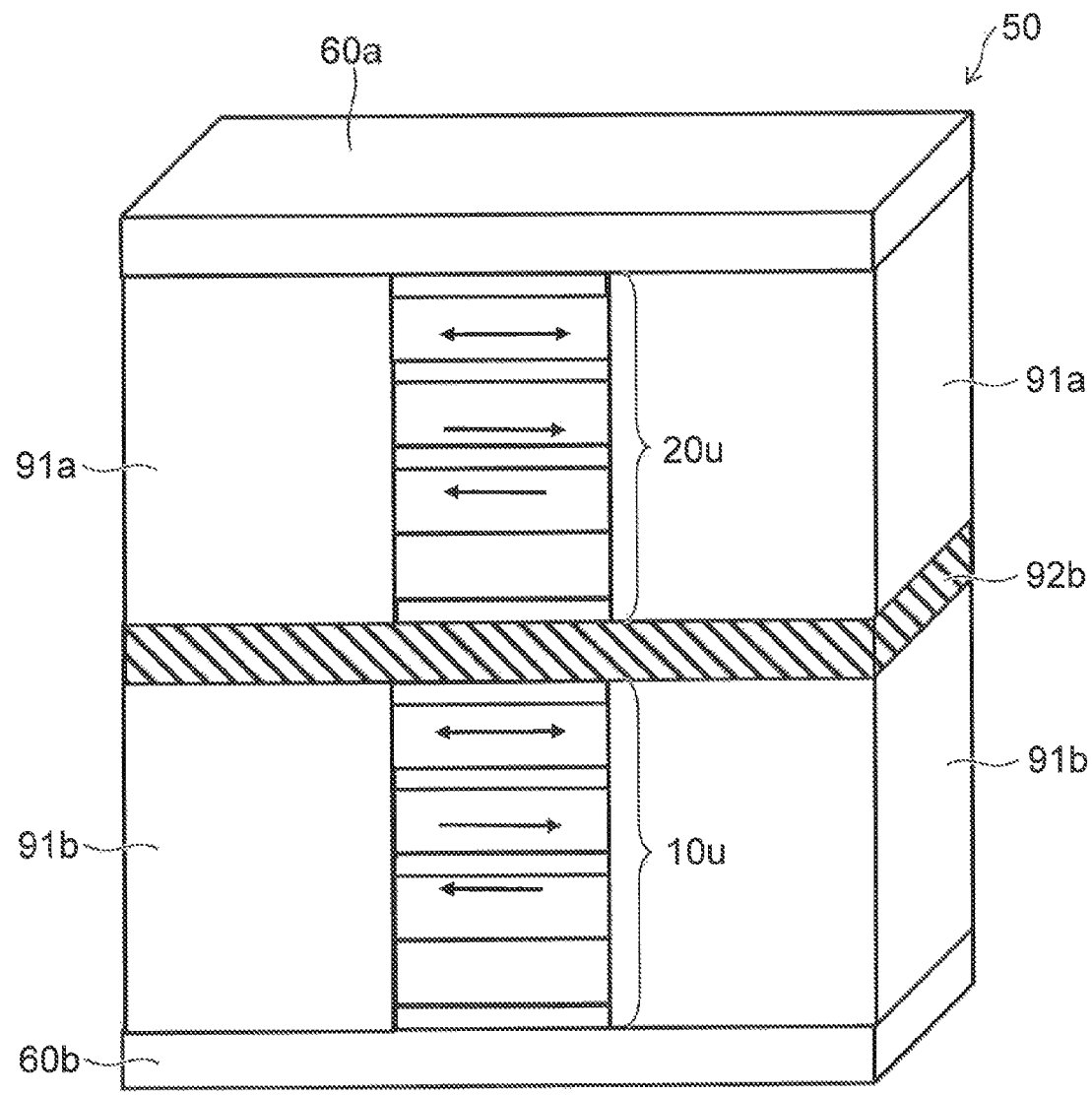
FIG. 14 is a schematic perspective view showing part of a strain sensing element according to the embodiment.

FIG. 14 is a schematic perspective view illustrating part of a strain sensing element according to the embodiment.

As shown in FIG. 14, the sensing unit 50 includes a shield layer 92b (a second shield layer) provided between the first sensing element 10u and the second sensing element 20u. That is, the sensing unit 50 includes the second shield layer provided between the second sensing element 20u and the first sensing element 10u. Also in the case where the shield layer 92b is provided between the first sensing element 10u and the second sensing element 20u, the stray magnetic fields generated from the magnetic layers of the plurality of sensing elements can be released to the shield layer, and the magnetic interference between sensing elements due to the stray magnetic field can be suppressed. For the shield layer 92b, a soft ferromagnetic material with a relatively high magnetic permeability such as NiFe is used, for example. The thickness of the shield layer 92b is not less than 5 nm and not more than 50 nm, for example.

At least one of the first hard bias layer 91a, the second hard bias layer 91b, the insulating layer 90, the shield layer 92a, and the shield layer 92b can be used for any of the strain sensing elements described below.

FIG. 15A to FIG. 15D are schematic perspective views illustrating parts of strain sensing elements according to the embodiment.

The drawings show examples of the connection of a plurality of sensing elements.

Figure 15A:
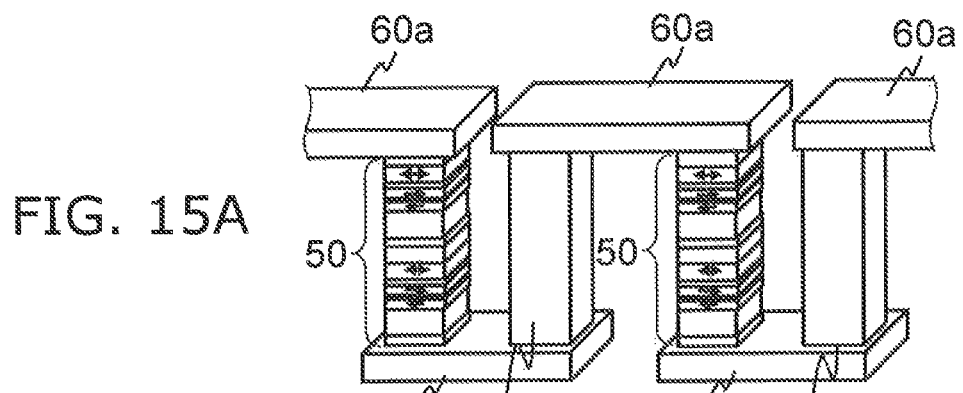
FIG. 15A to FIG. 15D are schematic perspective views showing parts of strain sensing elements according to the embodiment.

As shown in FIG. 15A, in the case where a plurality of sensing units 50 are electrically connected in series, the sensing unit 50 and a via contact 63 are provided between the lower electrode 60b (for example, the second interconnection 62) and the upper electrode 60a (for example, the first interconnection 61). Thereby, the currents passed through the sensing units 50 are in the same direction. The current passed through the plurality of sensing units 50 may be in the downward direction or the upward direction.

In the example shown in FIG. 15A, the plurality of sensing units 50 are connected in series. When the number of sensing elements stacked in the sensing unit 50 and connected in series is denoted by Nv and the number of sensing units 50 arranged in the plane and connected in series is denoted by Np, the total number of sensing elements connected in series is N=Nv×Np. The electric signal obtained at this time is N times of that when the number of sensing elements is one. On the other hand, the thermal noise and the Schottky noise are $N^{1/2}$ times. That is, the S/N ratio (signal-noise ratio; SNR) is $N^{1/2}$ times. By increasing the number N of sensing elements connected in series, the S/N ratio can be improved without increasing the size of the film unit.

In the embodiment, by using the sensing unit 50 in which a plurality of sensing elements are stacked, the restriction on the number of sensing elements that can be arranged in the region on the film unit 70d where an anisotropic strain is generated can be relaxed, and a sufficient number of sensing elements can be arranged. The change in electric resistance with respect to the pressure (for example, polarity) is similar between sensing elements arranged on the film unit 70*d*. Therefore, it is possible to sum up the signals of the plurality of sensing elements.

The bias voltage applied to one sensing element is not less than 50 millivolts (mV) and not more than 150 mV, for example. When N sensing elements are connected in series, the bias voltage is not less than 50 mV×N and not more than 150 mV×N. When the number N of sensing elements connected in series is 25, the bias voltage is not less than 1 V and not more than 3.75 V, for example.

When the value of the bias voltage is 1 V or more, the design of an electric circuit that processes the electric signal obtained from the sensing element is easy, and this is preferable in practical terms. In the embodiment, a plurality of sensing elements from which electric signals with the same polarity are obtained when pressure is applied can be arranged. Therefore, by connecting them in series, the S/N ratio can be improved as mentioned above.

Bias voltages (inter-terminal voltages) exceeding 10 V are not preferable in the electric circuit that processes the electric signal obtained from the sensing element. In the embodiment, the number N of sensing elements connected in series and the bias voltage are set so that an appropriate voltage range is obtained.

The voltage when the plurality of sensing elements are electrically connected in series is preferably not less than 1 V and not more than 10 V, for example. The voltage applied between the terminals of the plurality of sensing elements electrically connected in series (between the terminal of one end and the terminal of the other end) is not less than 1 V and not more than 10 V, for example.

To generate this voltage, when the bias voltage applied to one sensing element is 50 mV, the number N of sensing elements connected in series is preferably not less than 20 and not more than 200. When the bias voltage applied to one sensing element is 150 mV, the number N of sensing elements connected in series is preferably not less than 7 and not more than 66.

Figure 15B:
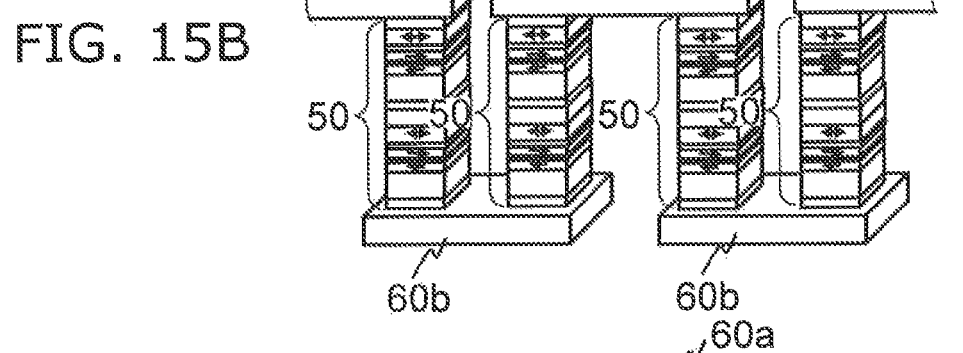

As shown in FIG. 15B, the sensing unit 50 is disposed between the lower electrode 60*b* and the upper electrode 60*a*, with no via contact provided. In this example, the directions of the currents passed through adjacent two sensing units 50 are opposite to each other. In this connection, the density of the arrangement of sensing units 50 is high.

Figure 15C:
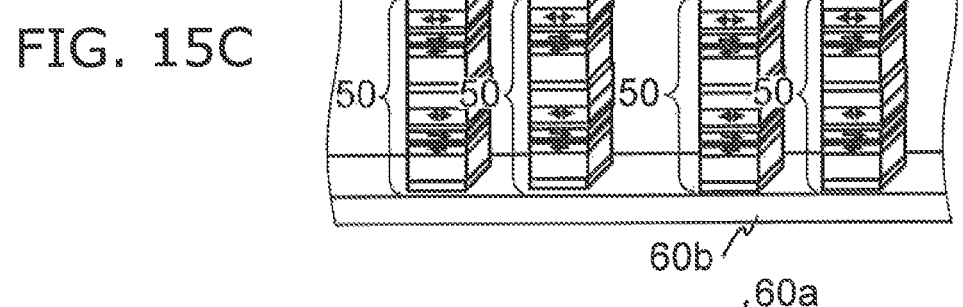

As shown in FIG. 15C, a plurality of sensing units 50 are provided between one lower electrode 60*b* and one upper electrode 60*a*. The plurality of sensing units 50 are connected in parallel.

Figure 15D:
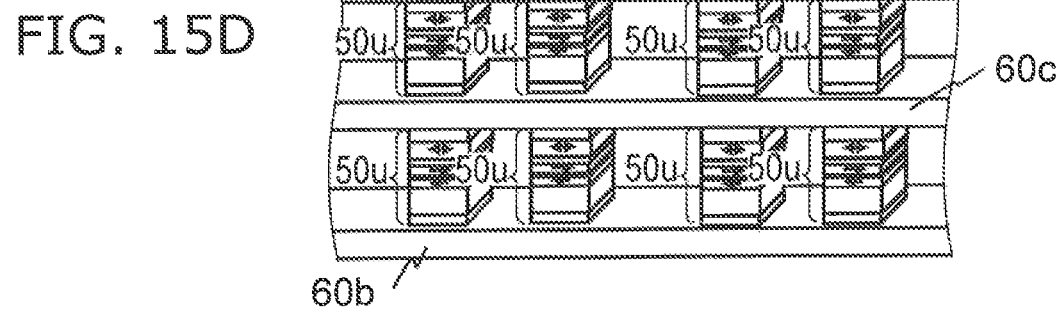

As shown in FIG. 15D, a plurality of sensing units 50 are provided between one lower electrode 60*b* and one upper electrode 60*a*. In the plurality of sensing units 50, an interlayer electrode 60*c* is provided between sensing elements 50*u* stacked. When the interlayer electrode 60*c* is formed of a soft magnetic material, it can be made to function as a shield.

Figure 16A:
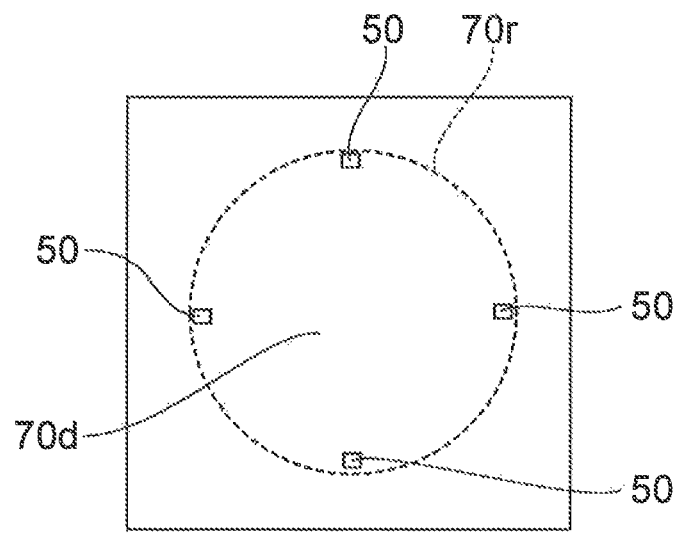
FIG. 16A to FIG. 16B are schematic diagrams showing a pressure sensor according to the embodiment.
Figure 16B:
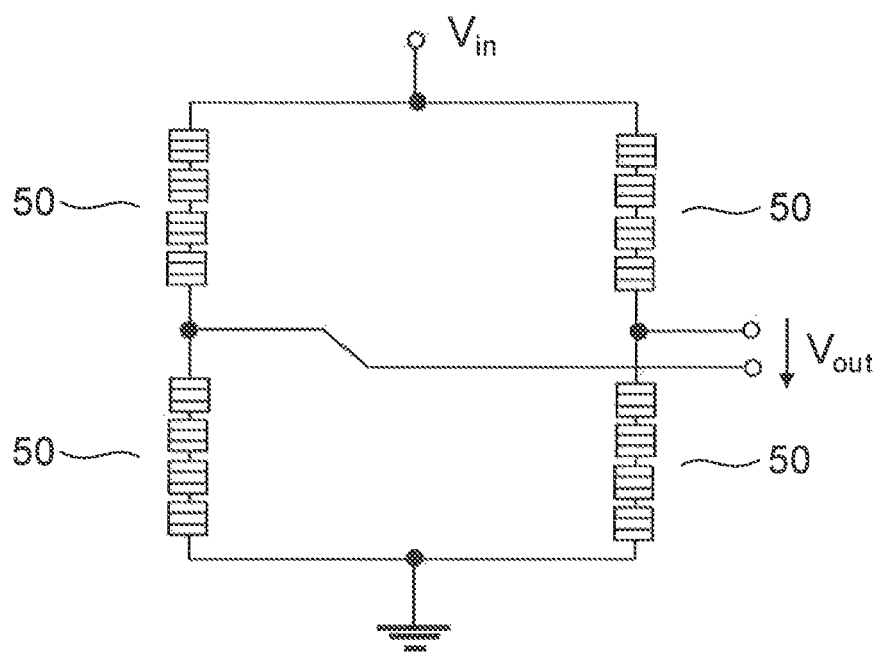

FIG. 16A to FIG. 16B are schematic diagrams illustrating a pressure sensor according to the embodiment. In this example, the pressure sensor includes a plurality of sensing units 50. FIG. 16A shows an example of the arrangement on the film unit 70*d* of sensing units 50. FIG. 16B shows an example of the connection state of sensing units.

As shown in FIG. 16A, a plurality of sensing units 50 are arranged on the film unit 70*d*. A substantially equal change in electric resistance with respect to the pressure can be obtained in the plurality of sensing units 50. The S/N ratio is increased by connecting a plurality of sensing units 50 in series or in parallel.

Although a plurality of sensing units 50 are arranged in FIG. 16A, the number of sensing units 50 may be one. FIG. 16A shows an example of the arrangement of sensing units 50 on the film unit 70*d* in a circular shape.

Thus, in the embodiment, the sensing unit 50 is provided in plural, for example. The plurality of sensing units 50 are provided on part of the film unit 70*d*. The plurality of sensing units 50 are apart from one another in a direction crossing the first direction mentioned above.

A very small size is sufficient as the size of the sensing unit. Therefore, the area of the sensing element can be made sufficiently smaller than the area of the film unit that bends due to pressure. The area of the sensing element can be made not more than ⅕ of the area of the film unit, for example.

When the diameter dimension of the film unit 70*d* is approximately 60 μm, the dimension of the sensing element may be 12 μm or less, for example. When the diameter dimension of the film unit 70*d* is approximately 600 μm, the dimension of the sensing element may be 120 μm or less, for example.

In this case, in view of the processing accuracy of the sensing element etc., there is no need to make each dimension of the sensing element excessively small. Thus, the dimension of the sensing element may be set not less than 0.05 μm and not more than 30 μm, for example.

In the example shown in FIG. 16A, the planar shape of the film unit 70*d* is a circle. The planar shape of the film unit 70*d* is not limited to a circle, and may be an ellipse or a polygon (including a square, a rectangle, a regular polygon, etc.), for example.

As shown in FIG. 16B, a plurality of sensing units 50 may be connected so as to form a Wheatstone bridge circuit. Thereby, the temperature compensation of detected characteristics can be made, for example.

A method for manufacturing a strain sensing element (a pressure sensor) according to the embodiment will now be described.

FIG. 17A to FIG. 17E are schematic cross-sectional views showing a method for manufacturing part of a strain sensing element according to the embodiment.

FIG. 17A to FIG. 17E show a method for manufacturing the sensing unit 50 shown in FIG. 5.

Figure 17A:
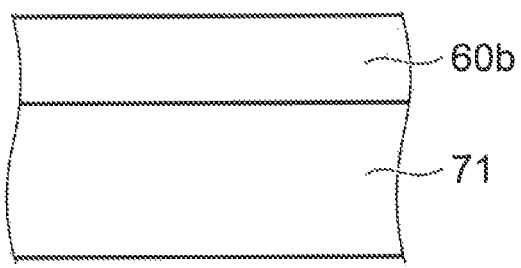
FIG. 17A to FIG. 17E are schematic cross-sectional views showing a method for manufacturing part of a strain sensing element according to the embodiment.

As shown in FIG. 17A, the lower electrode 60*b* is formed on a substrate 71 that forms the film unit 70*d* later.

Figure 17B:
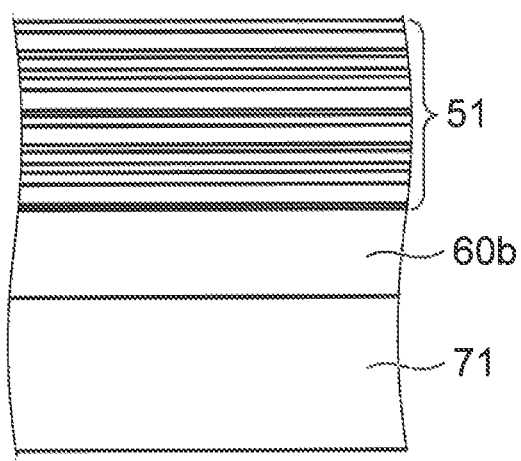

As shown in FIG. 17B, a stacked film 51 that forms the sensing unit 50 is formed on the lower electrode 60*b*. The material of each layer of the stacked film is as described in regard to FIG. 5, for example.

Figure 17C:
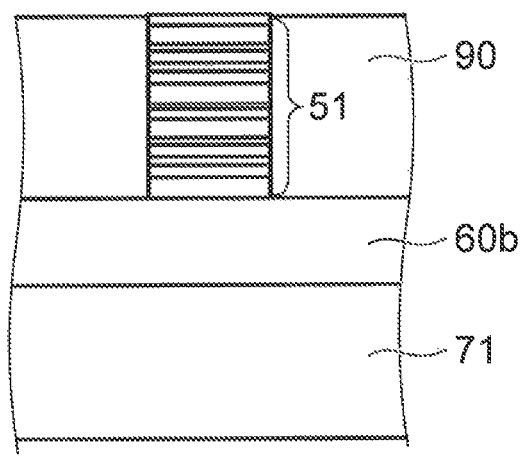

As shown in FIG. 17C, the planar configuration of the stacked film 51 of the sensing unit is processed. In this process, the planar configuration of a resist is patterned by photolithography, for example. After that, the not-shown resist pattern is used as a mask to use physical etching (milling) or chemical etching. After that, the insulating layer 90 is buried and made into a film around the stacked film 51. In this process, a lift-off process may be used, for example. That is, the insulating layer 90 is formed on the entire surface while the resist pattern formed by photolithography is left, and then the resist pattern is removed. As the insulating layer 90, $SiO_x$, $AlO_x$, $SiN_x$, $AlN_x$, and the like may be used.

When a tunneling magnetoresistance film using an insulating layer is used as the spacer layer of the sensing element of the stacked film 51, re-deposition on the side wall in the processing using physical etching (milling) or the like is suppressed. When an insulating layer is used as the spacer layer, substances will be re-deposited to the side wall of the insulating layer; and the adverse effect of "shunting" will be caused, in which a current flows through the re-deposited substances during vertical current passage and this leads to insufficient current passage through the insulating layer that is the spacer layer, and the magnetoresistance effect is degraded. The milling of planar configuration processing of the sensing unit 50 is performed under optimum conditions in order to prevent shunting.

In the sensing unit 50 of the embodiment, since a plurality of sensing elements are stacked, the amount of re-deposited substances is larger than in the case of using one sensing element. This is due to the fact that the amount of re-deposited substances increases depending on the total thickness of the sensing unit 50 etched.

In the case where the processing of the planar configuration of the sensing unit 50 is performed by physical etching (milling), for the purposes of ensuring a sufficient etching rate and controlling the shape of the side wall of the element, low-angle and middle-angle milling is performed in which an Ar ion beam or the like is caused to be incident at a low to middle angle of 0 degrees to 50 degrees, with the perpendicular-to-plane direction as 0 degrees. At this time, substances will be re-deposited to the side wall of the sensing unit 50. After the milling for the thickness of the sensing unit 50 is performed, high-angle milling is performed in which milling is performed from a direction at a high angle with respect to the direction perpendicular to the substrate to perform milling only toward the side wall of the sensing unit 50. Thereby, the re-deposited substances on the side wall of the sensing unit 50 are removed. When the planar processing of the sensing unit 50 of this example is performed, it is preferable that the high-angle milling be performed for a longer time than the time for performing it on one sensing element. When the processing of the planar configuration of the sensing unit 50 of this example is performed, low-angle and angle milling and high-angle milling may be performed repeatedly.

When a sensing unit 50 including three sensing elements is processed, the portion of the thickness of the sensing element of the first from the surface is removed by low-angle and middle angle milling, and then high-angle milling is performed to remove the re-deposited substances on the side wall of the sensing element of the first from the surface, for example. Next, the portion of the thickness of the sensing element of the second is removed by low-angle and middle-angle milling, and then high-angle milling is performed. Subsequently, the portion of the thickness of the sensing element of the third is removed by low-angle and middle-angle milling, and then high-angle milling is performed. By performing low-angle and middle-angle milling and high-angle milling repeatedly in this way, the re-deposited substances on the side wall of the sensing unit 50 can be removed sufficiently, and milling damage to the side wall can be reduced.

Figure 17D:
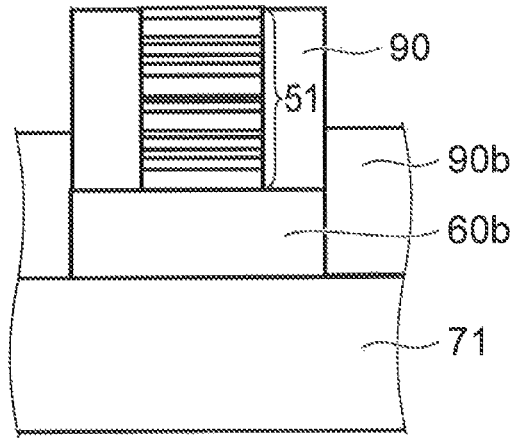

As shown in FIG. 17D, the planar configuration of the lower electrode 60b is processed. In this process, a resist is patterned by photolithography, and then the not-shown resist pattern is used as a mask to perform physical etching (milling) or chemical etching for processing, for example. After that, an insulating layer 90b is buried and made into a film around the sensing unit 50. In this process, a lift-off process is performed, for example. In the lift-off process, the insulating layer 90b is formed on the entire surface while the resist pattern formed by photolithography is left, and then the resist pattern is removed, for example. As the insulating layer 90b, $SiO_x$, $AlO_x$, $SiN_x$, $AlN_x$, and the like may be used.

In this example, the processing of the lower electrode 60b is performed after the planar configuration of the sensing unit 50 is processed. In the embodiment, the processing of the lower electrode 60b may be performed in the beginning. The film formation of the stacked film 51 that forms the sensing unit 50 shown in FIG. 17B may be performed on the lower electrode 60b of which the planar configuration has been processed.

Figure 17E:
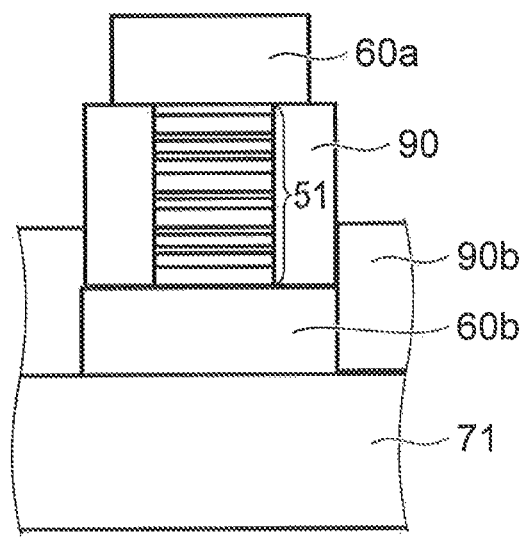
Figure 18A:
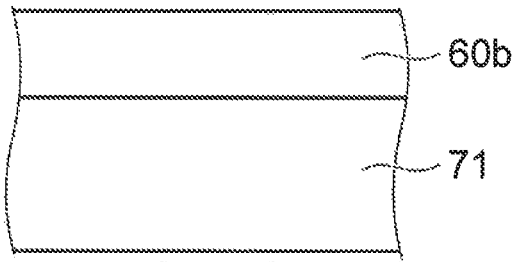
FIG. 18A to FIG. 18G are schematic cross-sectional views showing a method for manufacturing part of a strain sensing element according to the embodiment.
Figure 18B:
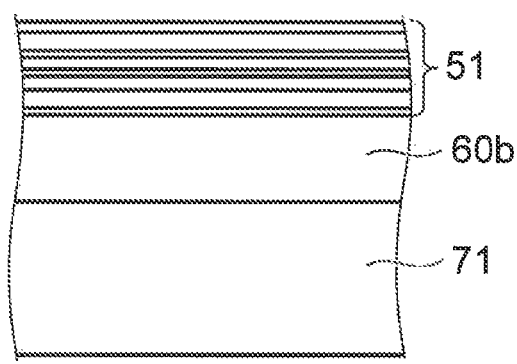
Figure 18C:
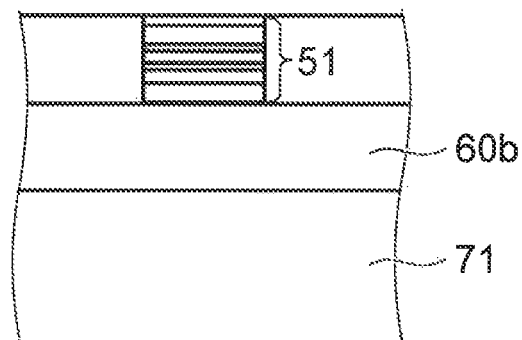
Figure 18D:
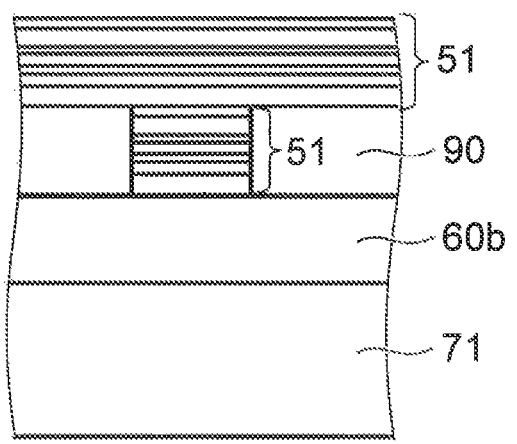
Figure 18E:
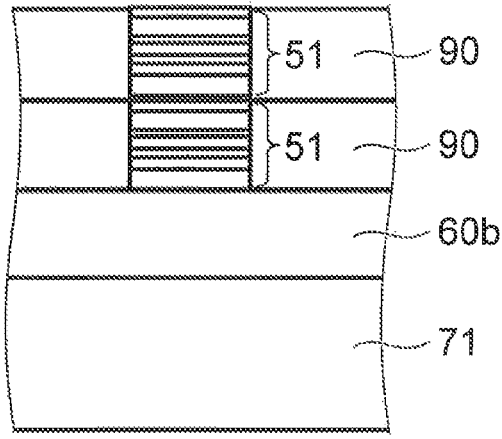
Figure 18F:
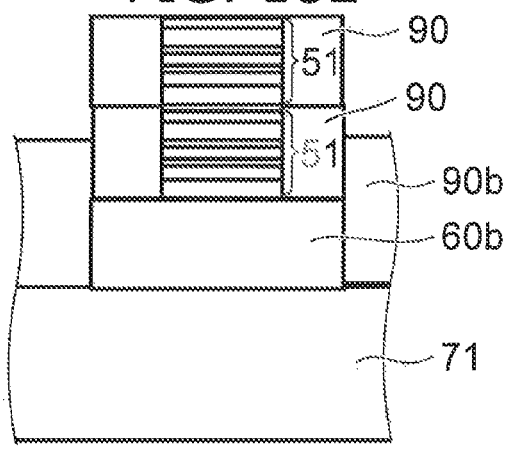
Figure 18G:
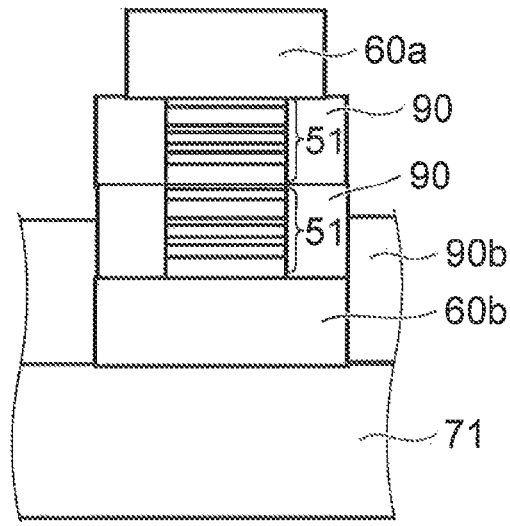

As shown in FIG. 17E, the upper electrode 60a is formed into a film, and the planar configuration thereof is processed. In this process, a resist is patterned by photolithography, and then the not-shown resist pattern is used as a mask to perform physical etching (miffing) or chemical etching for processing.

FIG. 18A to FIG. 18G are schematic cross-sectional views showing a method for manufacturing part of a strain sensing element according to the embodiment.

FIG. 18A to FIG. 18G show another method for manufacturing the sensing element shown in FIG. 5.

In the example of FIG. 18A to FIG. 18G, when a sensing unit 50 including two stacked sensing elements is fabricated, film formation and processing are performed for each of the two sensing elements.

When a sensing unit 50 including six sensing elements is fabricated, film formation and processing may be performed for every three sensing elements separately, for example. In the case of sensing 50 including six sensing elements like this, if the total thickness of the sensing unit 50 is too large, the manufacturing method shown in FIG. 17A to FIG. 17E in which the film formation and processing of the sensing unit 50 are performed by one round may lead to insufficient removal of the re-deposited substances on the side wall of the sensing element included. Otherwise, there is a case where, although the re-deposited substances can be removed, the time for high-angle milling is long and additional damage occurs to the side wall of the sensing unit 50, for example. When the thickness of the sensing unit 50 is too large, the thickness of one round of film formation of the embedded insulating layer 90b that is formed around the sensing unit 50 will be thick. At this time, the removal of the resist will be difficult in the lift-off process.

When the total number of sensing elements included in the sensing unit 50 or the total thickness thereof is large, the film formation and processing of the stacked film 51 is preferably performed multiple times separately as shown in FIG. 18A to FIG. 18G, for example.

A method for manufacturing a strain sensing element (a pressure sensor) according to the embodiment will now be described.

FIG. 19A to FIG. 19E are schematic perspective views illustrating a method for manufacturing a strain sensing element according to the embodiment.

Figure 19A:
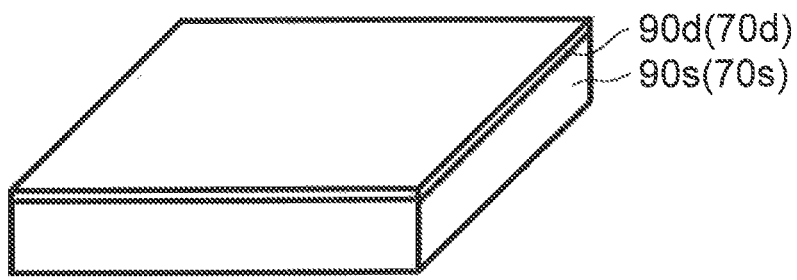
FIG. 19A to FIG. 19E are schematic perspective views showing a method for manufacturing a strain sensing element according to the embodiment.

As shown in FIG. 19A, a thin film 90d is formed on a substrate 90s (for example, a Si substrate). The substrate 90s forms the support 70s. The thin film 90d forms the film unit 70d.

A thin film 90d of $SiO_x$/Si is formed by sputtering on a Si substrate, for example. A $SiO_x$ single layer, a SiN single layer, or a metal layer of Al or the like may be used as the thin film 90d. A flexible plastic material such as a polyimide and a paraxylene-based polymer may be used as the thin film 90d. An SOI (silicon on insulator) substrate may be used as the substrate 90s and the thin film 90d. In the SOT, a stacked film of $SiO_2$/Si is formed on a Si substrate by attaching the substrates, for example.

Figure 19B:
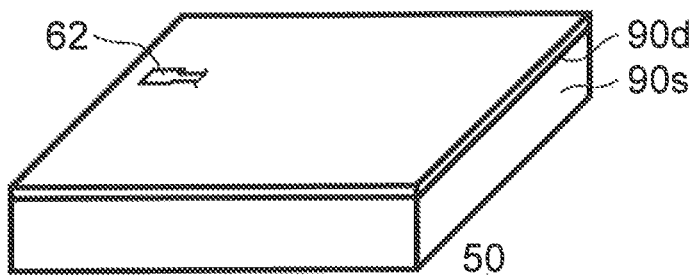

As shown in FIG. 19B, the second interconnection 62 is formed. In this process, a conductive film that forms the second interconnection 62 is formed, and the conductive film is processed by photolithography and etching. In the case where the surroundings of the second interconnection 62 are filled with an insulating film, lift-off process may be used. In the lift-off process, after the etching of the pattern of the second interconnection 62 and before the peeling of the resist, an insulating film is formed into a film over the entire surface and then the resist is removed, for example.

Figure 19C:
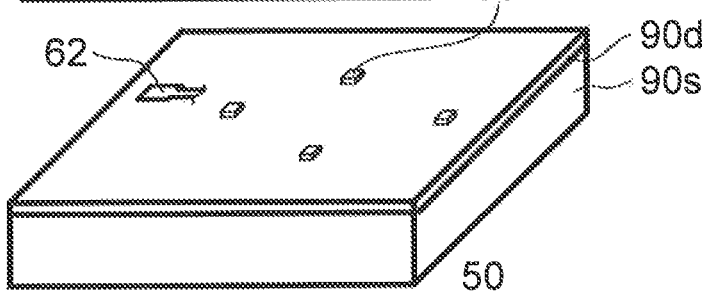

As shown in FIG. 19C, sensing units 50 are formed. In this process, a stacked film that forms the sensing unit 50 is formed, and the stacked film is processed by photolithography and etching. In the case where the space on the side wall of the stacked body of the sensing element is filled with an insulating layer, lift-off process may be used. In the lift-off process, after the processing of the stacked body and before the peeling of the resist, an insulating layer is formed into a film over the entire surface and then the resist is removed, for example.

Figure 19D:
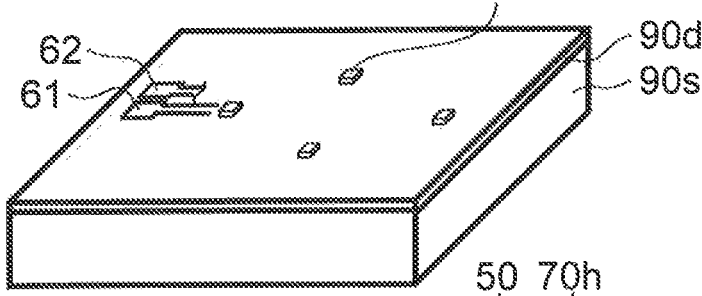

As shown in FIG. 19D, the first interconnection 61 is formed. In this process, a conductive film that forms the first interconnection 61 is formed, and the conductive film is processed by photolithography and etching. In the case where the surroundings of the first interconnection 61 are filled with an insulating film, lift-off process may be used. In the lift-off process, after the processing of the first interconnection 61 and before the peeling of the resist, an insulating film is formed into a film over the entire surface and then the resist is removed.

Figure 19E:
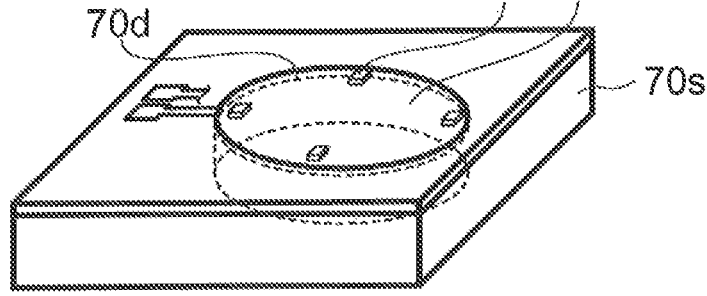

As shown in FIG. 19E, etching is performed from the back surface of the substrate 90s to form the hollow portion 70h. Thereby, the film unit 70d and the support 70s are formed. In the case where a stacked film of $SiO_x$/Si is used as the thin film 90d that forms the film unit 70d, deep digging processing of the substrate 90s is performed from the back surface (the lower surface) toward the front surface (the upper surface) of the thin film 90d, for example. Thereby, the hollow portion 70h is formed. In the formation of the hollow portion 70h, a both-surface aligner exposure apparatus may be used, for example. Thereby, the hole pattern of the resist can be formed on the back surface in accordance with the position of the sensing unit 50 on the front surface.

In the etching of the Si substrate, the Bosch process using RIE may be used, for example. In the Bosch process, an etching process using $SF_6$ gas and a deposition process using $C_4F_8$ gas are repeated, for example. Thereby, etching is performed selectively in the depth direction of the substrate 90s (the Z-axis direction) while the etching of the side wall of the substrate 90s is suppressed. A $SiO_x$ layer is used as the end point of the etching, for example. That is, the etching is finished using a $SiO_x$ layer, which is different in etching selectivity from Si. The $SiO_x$ layer functioning as an etching stopper layer may be used as part of the film unit 70d. The $SiO_x$ layer may be removed after the etching by treatment with anhydrous hydrogen fluoride and an alcohol, or the like, etc., for example.

Thus, the pressure sensor 310 according to the embodiment is formed. Other pressure sensors according to the embodiment can be manufactured by similar methods.

Second Embodiment

Figure 20A:
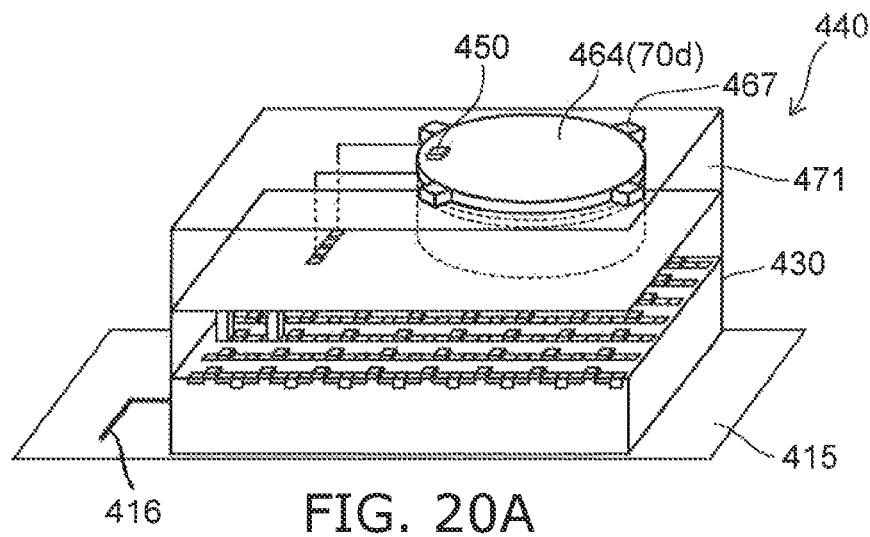
FIG. 20A to FIG. 20C are schematic diagrams showing a pressure sensor according to a second embodiment.
Figure 20B:
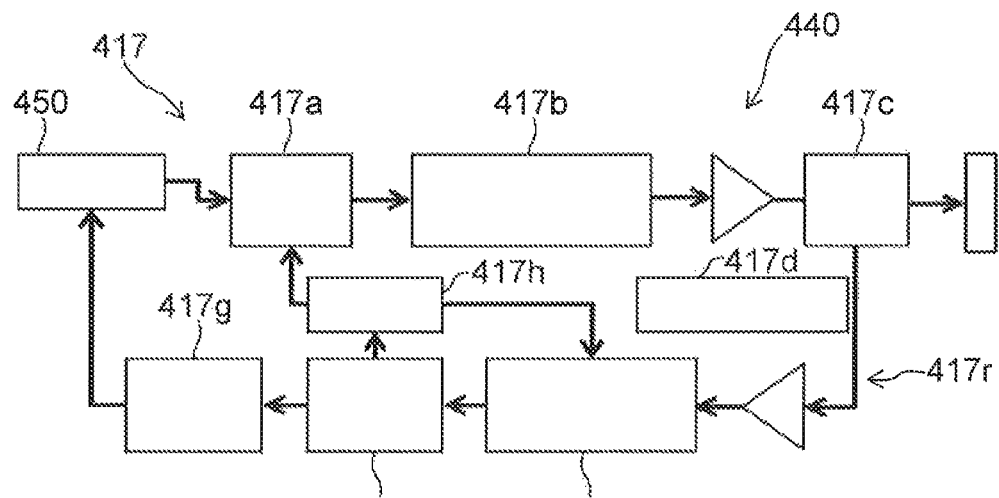
Figure 20C:
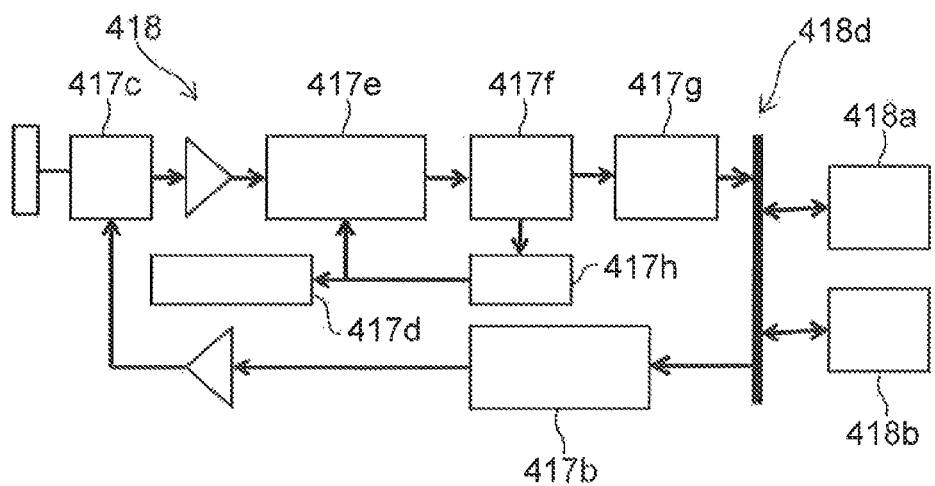

FIG. 20A to FIG. 20C are schematic diagrams illustrating a pressure sensor according to a second embodiment.

FIG. 20A is a schematic perspective view, and FIG. 20B and FIG. 20C are block diagrams illustrating a pressure sensor 440.

As shown in FIG. 20A and FIG. 20B, in the pressure sensor 440, a base 471, a sensing unit 450, a semiconductor circuit unit 430, an antenna 415, an electric interconnection 416, a transmitting circuit 417, and a receiving circuit 417r are provided.

The antenna 415 is electrically connected to the semiconductor circuit unit 430 via the electric interconnection 416.

The transmitting circuit 417 transmits data based on an electric signal traveling through the sensing unit 450 wirelessly. At least part of the transmitting circuit 417 may be provided in the semiconductor circuit unit 430.

The receiving circuit 417r receives a control signal from an electronic device 418d. At least part of the receiving circuit 417r may be provided in the semiconductor circuit unit 430. By providing the receiving circuit 417r, the operation of the pressure sensor 440 can be controlled by operating the electronic device 418d, for example.

As shown in FIG. 20B, in the transmitting circuit 417, an A/D converter 417a connected to the sensing unit 450 and a Manchester encoding unit 417b may be provided, for example. A switching unit 417c may be provided to switch between transmission and reception. In this case, a timing controller 417d may be provided, and switching in the switching unit 417c can be controlled by the timing controller 417d. A data correction unit 417e, a synchronization unit 417f, a determination unit 417g, and a voltage-controlled oscillator 417h (VCO) may be further provided.

As shown in FIG. 20C, a receiving unit 418 is provided in the electronic device 418d used in combination with the pressure sensor 440. As the electronic device 418d, an electronic device such as a mobile terminal may be given, for example.

In this case, the pressure sensor 440 including the transmitting circuit 417 and the electronic device 418d including the receiving unit 418 may be used in combination.

In the electronic device 418d, a Manchester encoding unit 417b, a switching unit 417c, a timing controller 417d, a data correction unit 417e, a synchronization unit 417f, a determination unit 417g, a voltage-controlled oscillator 417h, a memory unit 418a, and a central processing unit 418b (CPU) may be provided.

In this example, the pressure sensor 440 further includes a fixing unit 467. The fixing unit 467 fixes a film unit 464 (70d) to the base 471. The fixing unit 467 may have a larger thickness dimension than the film unit 464 so as to bend less easily even when an external pressure is applied.

Fixing units 467 may be provided at equal intervals at the edge of the film unit 464, for example.

The fixing unit 467 may be provided so as to continuously surround the entire periphery of the film unit 464 (70d).

The fixing unit 467 may be formed of the same material as the material of the base 471, for example. In this case, the fixing unit 467 may be formed of silicon or the like, for example.

The fixing unit 467 may be formed of the same material as the material of the film unit 464 (70d), for example.

Third Embodiment

A method for manufacturing a pressure sensor according to an embodiment will now be described.

FIG. 21A, FIG. 21B, FIG. 22A, FIG. 22B, FIG. 23A, FIG. 23B, FIG. 24A, FIG. 24B, FIG. 25A, FIG. 25B, FIG. 26A, FIG. 26B, FIG. 27A, FIG. 27B, FIG. 28A, FIG. 28B, FIG. 29A, FIG. 29B, FIG. 30A, FIG. 30B, FIG. 31A, FIG. 31B, FIG. 32A, and FIG. 32B are schematic views illustrating a method for manufacturing a pressure sensor according to a third embodiment.

FIG. 21A to FIG. 32A are schematic plan views, and FIG. 21B to FIG. 32B are schematic cross-sectional views.

Figure 21A:
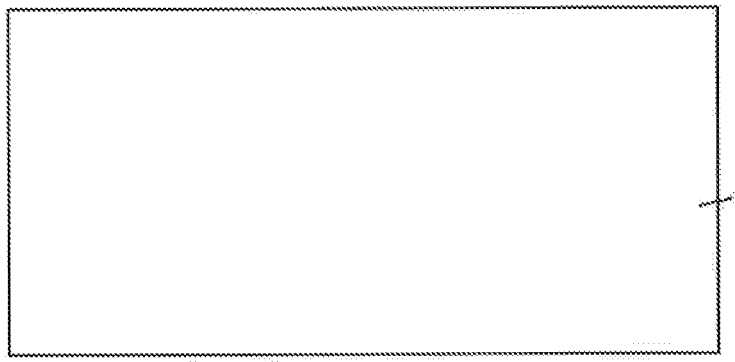
FIG. 21A and FIG. 21B, are schematic views showing a method for manufacturing a pressure sensor according to a third embodiment.
Figure 21B:
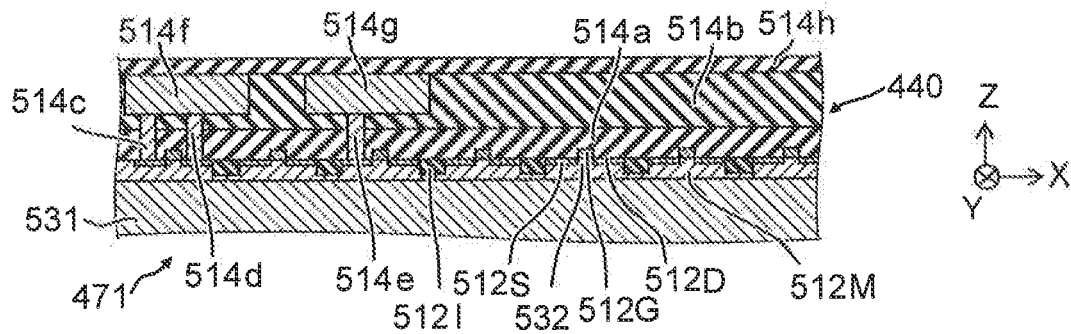

As shown in FIG. 21A and FIG. 21B, a semiconductor layer 512M is formed on a surface portion of a semiconductor substrate 531. Subsequently, an element isolation insulating layer 512I is formed on the upper surface of the semiconductor layer 512M. Subsequently, a gate 512G is formed on the semiconductor layer 512M via a not-shown insulating layer. Subsequently, a source 512S and a drain 512D are formed on both sides of the gate 512G to form a transistor 532. Subsequently, an interlayer insulating film 514a is formed thereon, and an interlayer insulating film 514b is formed.

Subsequently, in the region that forms a non-hollow portion, trenches and holes are formed in parts of the interlayer insulating films 514a and 514b. Subsequently, a conductive material is buried in the holes to form connection pillars 514c to 514e. In this case, the connection pillar 514c is electrically connected to the source 512S of a transistor 532, and the connection pillar 514d is electrically connected to the drain 512D, for example. The connection pillar 514e is electrically connected to the source 512S of another transistor 532, for example. Subsequently, a conductive material is buried in the trenches to form interconnection units 514f and 514g. The interconnection unit 514f is electrically connected to the connection pillar 514c and the connection pillar 514d. The interconnection unit 514g is electrically connected to the connection pillar 514e. Subsequently, an interlayer insulating film 514h is formed on the interlayer insulating film 514b.

Figure 22A:
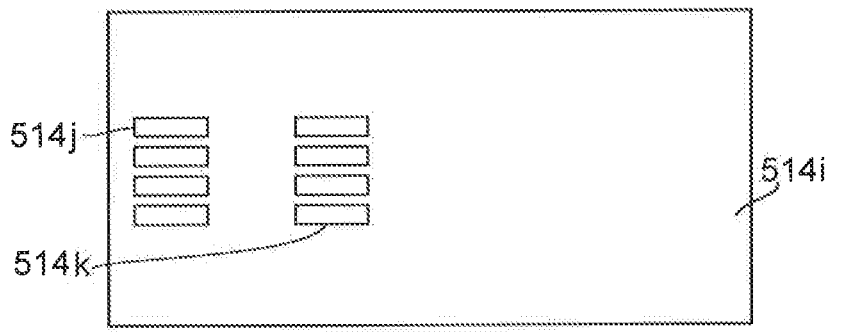
FIG. 22A and FIG. 22B, are schematic views showing a method for manufacturing a pressure sensor according to a third embodiment.
Figure 22B:
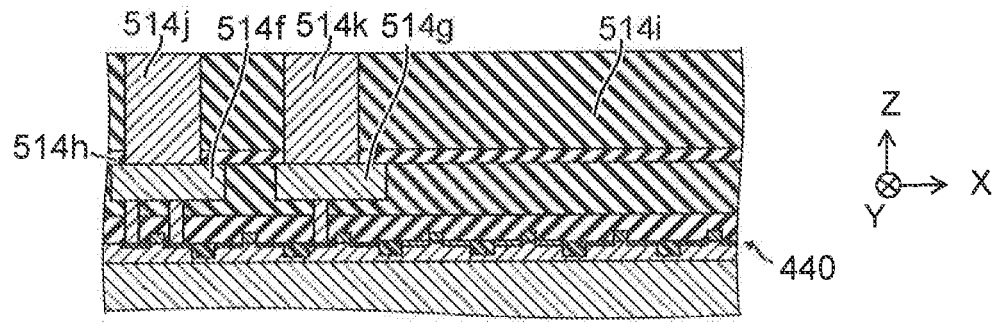

As shown in FIG. 22A and FIG. 22B, an interlayer insulating film 514i made of silicon oxide (SiO$_2$) is formed on the interlayer insulating film 514h using the CVD (chemical vapor deposition) method, for example. Subsequently, holes are formed in prescribed positions of the interlayer insulating film 514i, a conductive material (for example, a metal material) is buried, and the upper surface is planarized using the CMP (chemical mechanical polishing) method. Thereby, a connection pillar 514j connected to the interconnection unit 514f and a connection pillar 514k connected to the interconnection unit 514g are formed.

Figure 23A:
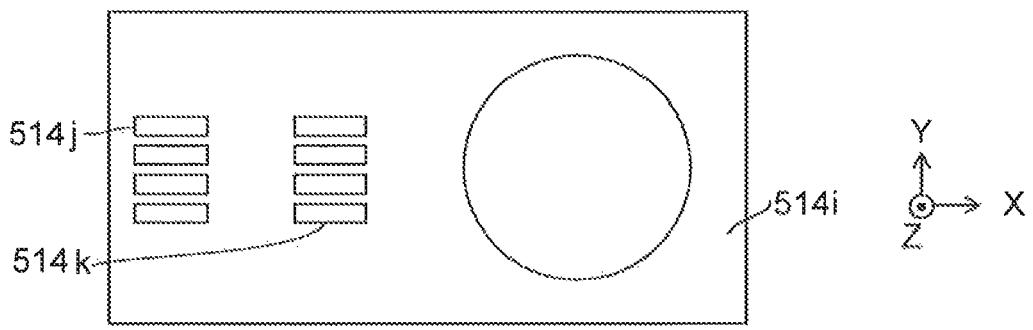
FIG. 23A and FIG. 23B, are schematic views showing a method for manufacturing a pressure sensor according to a third embodiment.
Figure 23B:
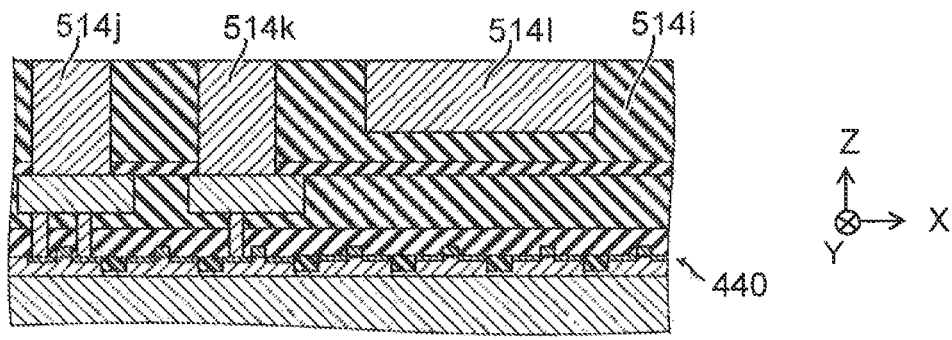

As shown in FIG. 23A and FIG. 23B, a recess is formed in a region of the interlayer insulating film 514i that forms a hollow portion 570, and a sacrifice layer 514l is buried in the recess. The sacrifice layer 514l may be formed using a material that can be formed into a film at low temperature, for example. The material that can be made into a film at low temperature is silicon germanium (SiGe) or the like, for example.

Figure 24A:
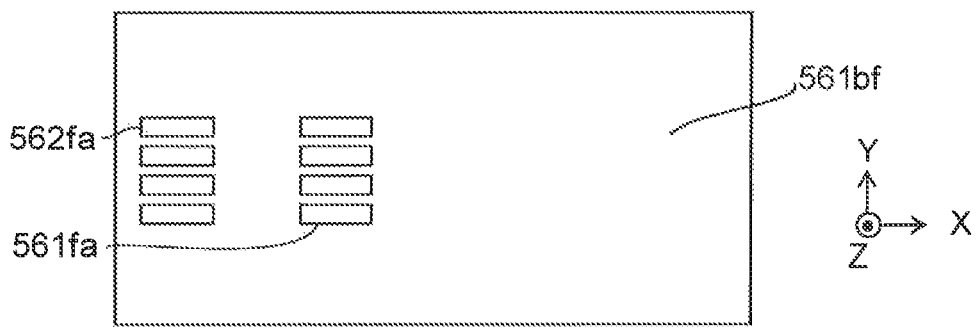
FIG. 24A and FIG. 24B, are schematic views showing a method for manufacturing a pressure sensor according to a third embodiment.
Figure 24B:
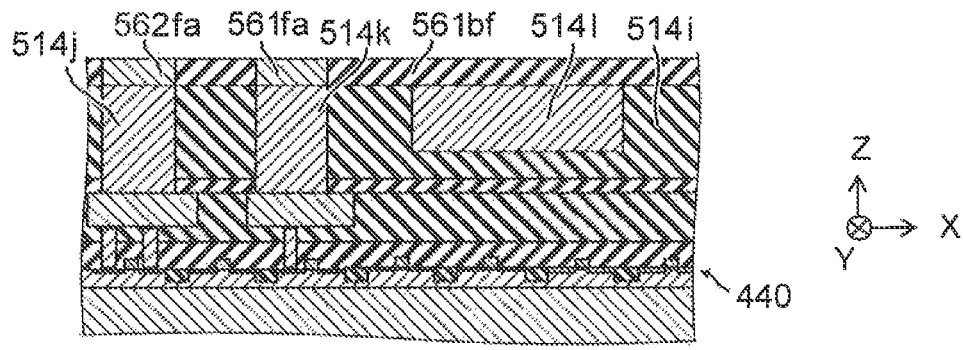

As shown in FIG. 24A and FIG. 24B, an insulating film 561bf that forms a film unit 564 (70d) is formed on the interlayer insulating film 514i and the sacrifice layer 514l. The insulating film 561bf may be formed using silicon oxide (SiO$_2$) or the like, for example. A plurality of holes are provided in the insulating film 561bf, and a conductive material (for example, a metal material) is buried in the plurality of holes to form a connection pillar 561fa and a connection pillar 562fa. The connection pillar 561fa is electrically connected to the connection pillar 514k, and the connection pillar 562fa is electrically connected to the connection pillar 514j.

Figure 25A:
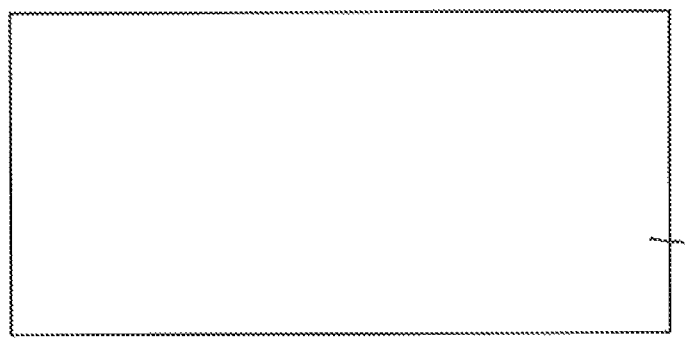
FIG. 25A and FIG. 25B, are schematic views showing a method for manufacturing a pressure sensor according to a third embodiment.
Figure 25B:
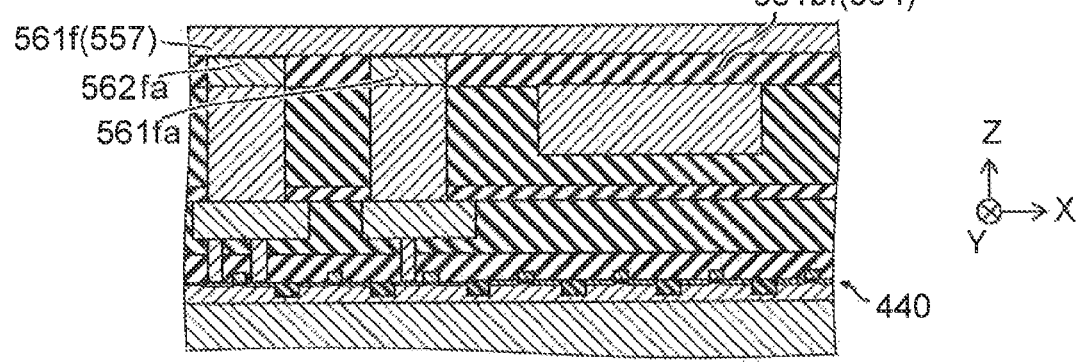

As shown in FIG. 25A and FIG. 25B, a conductive layer 561f that forms an interconnection 557 is formed on the insulating film 561bf, the connection pillar 561fa, and the connection pillar 562fa.

Figure 26A:
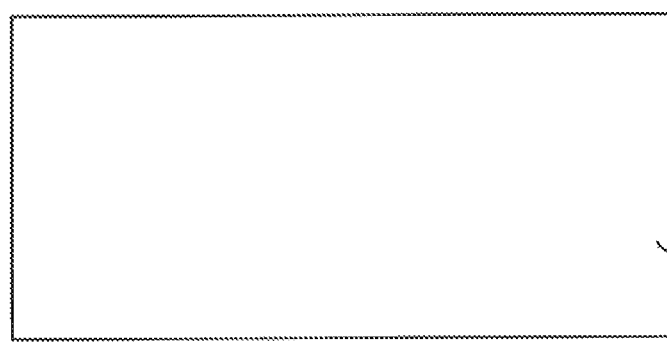
FIG. 26A and FIG. 26B, are schematic views showing a method for manufacturing a pressure sensor according to a third embodiment.
Figure 26B:
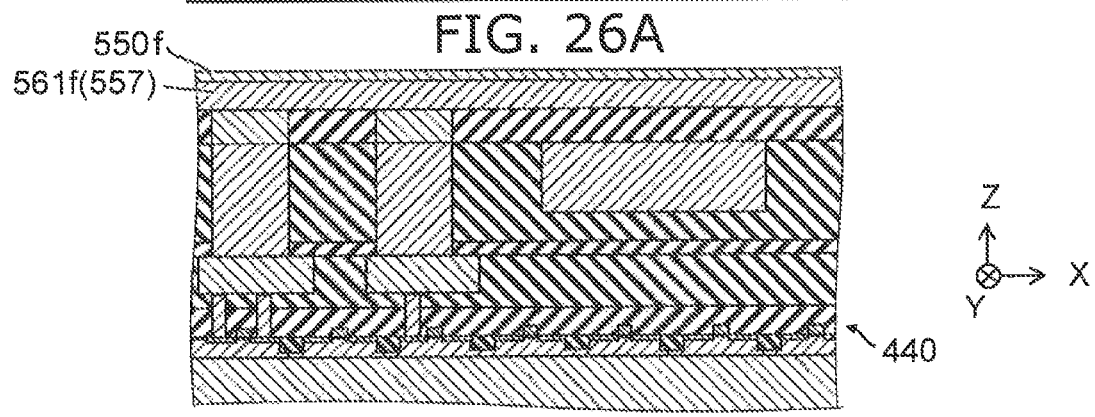

As shown in FIG. 26A and FIG. 26B, a stacked film 550f is formed on the conductive layer 561f.

Figure 27A:
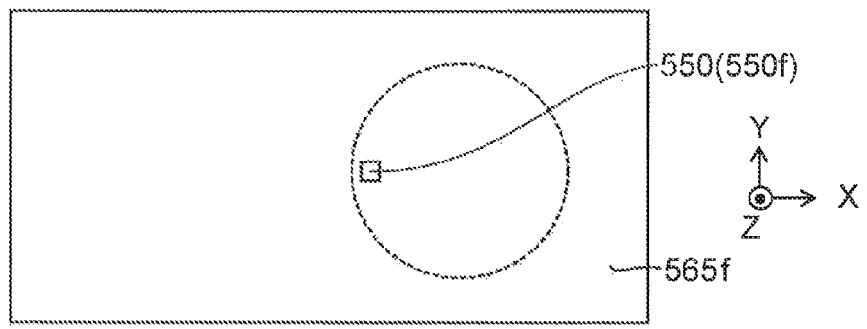
FIG. 27A and FIG. 27B, are schematic views showing a method for manufacturing a pressure sensor according to a third embodiment.
Figure 27B:
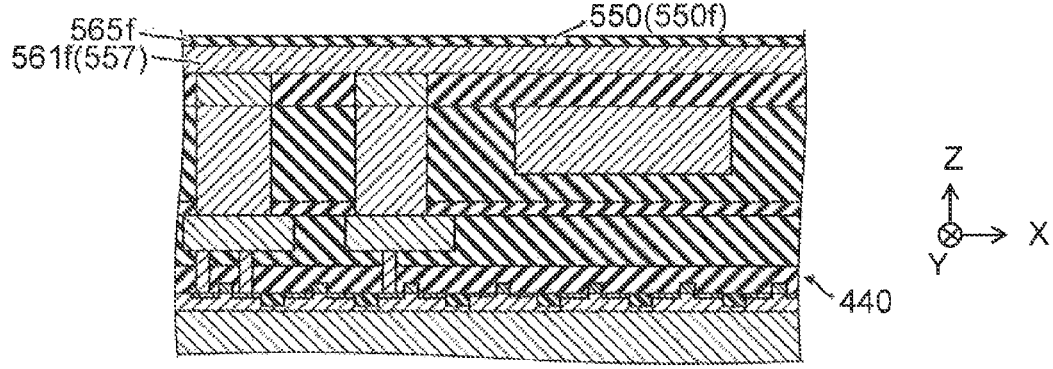

As shown in FIG. 27A and FIG. 27B, the stacked film 550f is processed into a prescribed shape, and an insulating film 565f that forms an insulating layer 565 is formed thereon. The insulating film 565f may be formed using silicon oxide (SiO$_2$) or the like, for example.

Figure 28A:
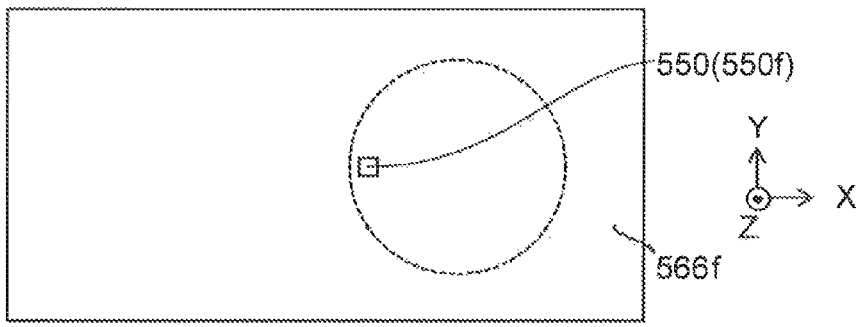
FIG. 28A and FIG. 28B, are schematic views showing a method for manufacturing a pressure sensor according to a third embodiment.
Figure 28B:
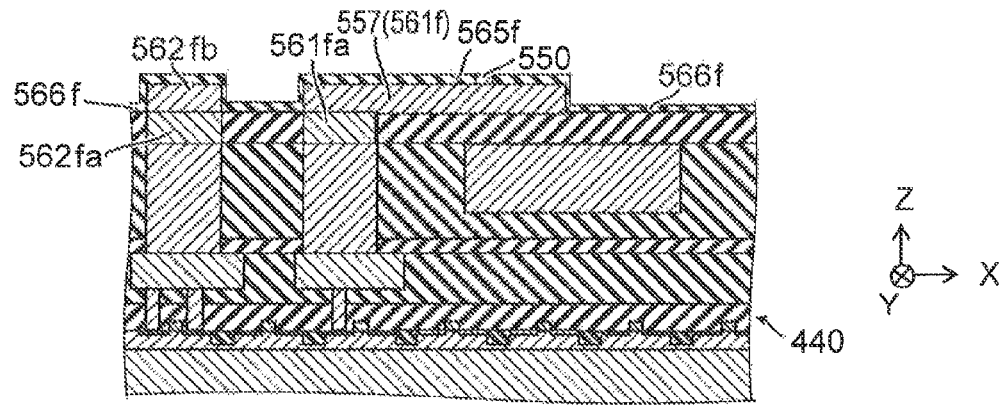

As shown in FIG. 28A and FIG. 28B, part of the insulating film 565f is removed, and the conductive layer 561f is processed into a prescribed shape. Thereby, an interconnection 557 is formed. At this time, part of the conductive layer 561f forms a connection pillar 562fb electrically connected to the connection pillar 562fa. Then, an insulating film 566f that forms an insulating layer 566 is formed thereon.

Figure 29A:
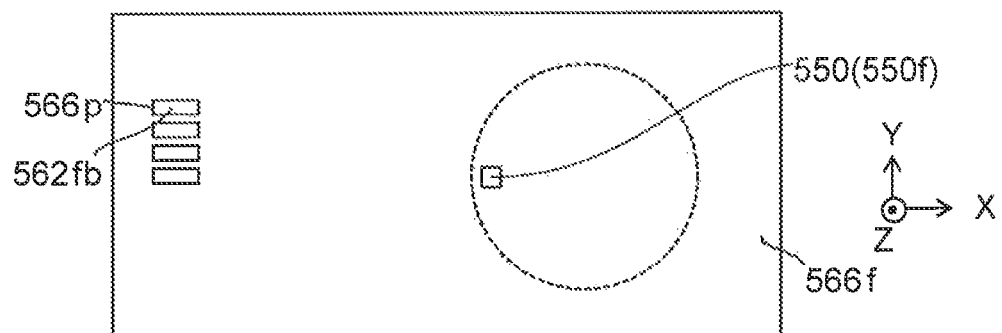
FIG. 29A and FIG. 29B, are schematic views showing a method for manufacturing a pressure sensor according to a third embodiment.
Figure 29B:
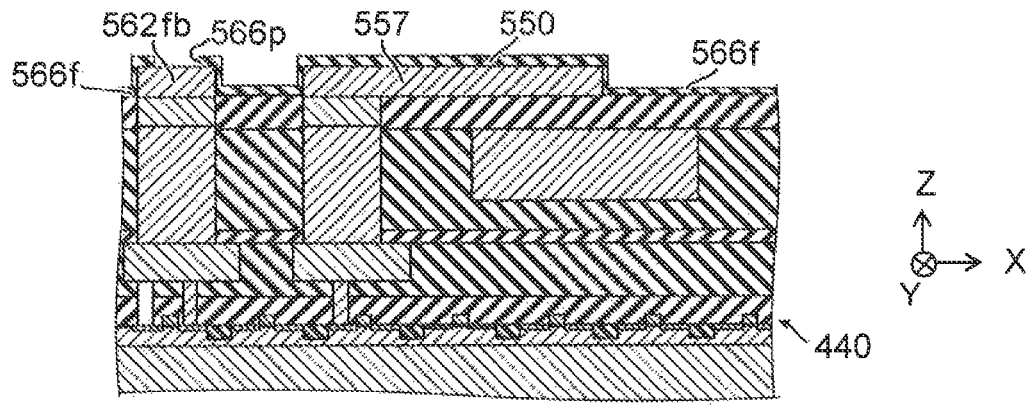

As shown in FIG. 29A and FIG. 29B, an opening 566p is formed in the insulating film 566f. Thereby, the connection pillar 562fb is exposed.

Figure 30A:
FIG. 30A and FIG. 30B, are schematic views showing a method for manufacturing a pressure sensor according to a third embodiment.
Figure 30B:
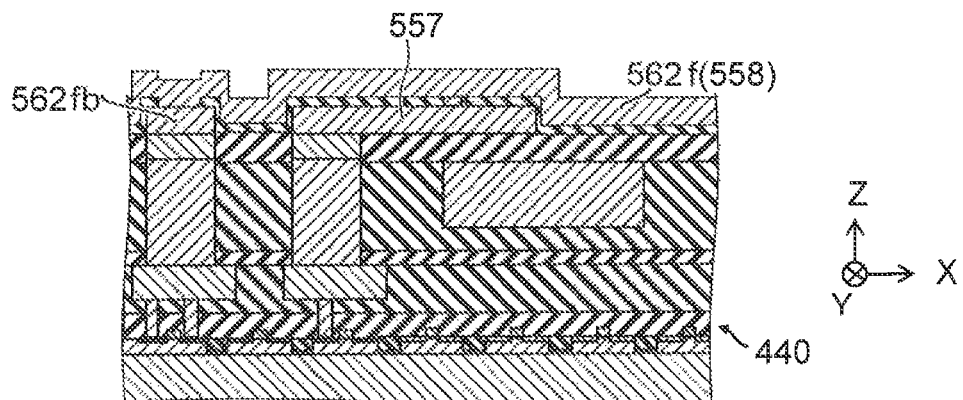

As shown in FIG. 30A and FIG. 30B, a conductive layer 562f that forms an interconnection 558 is formed on the upper surface. Part of the conductive layer 562f is electrically connected to the connection pillar 562fb.

Figure 31A:
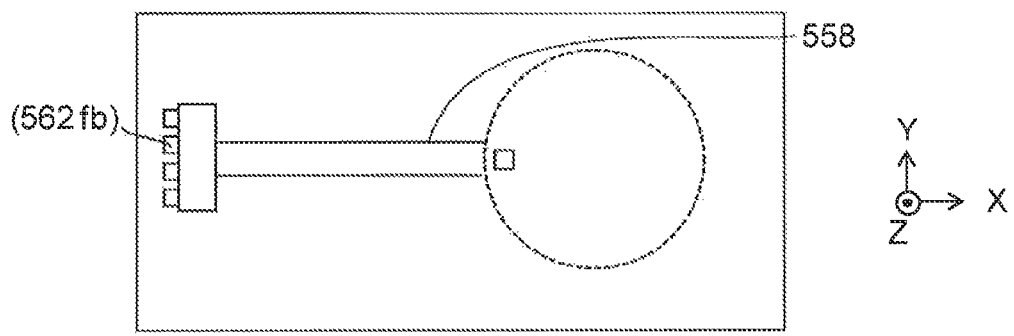
FIG. 31A and FIG. 31B, are schematic views showing a method for manufacturing a pressure sensor according to a third embodiment.
Figure 31B:
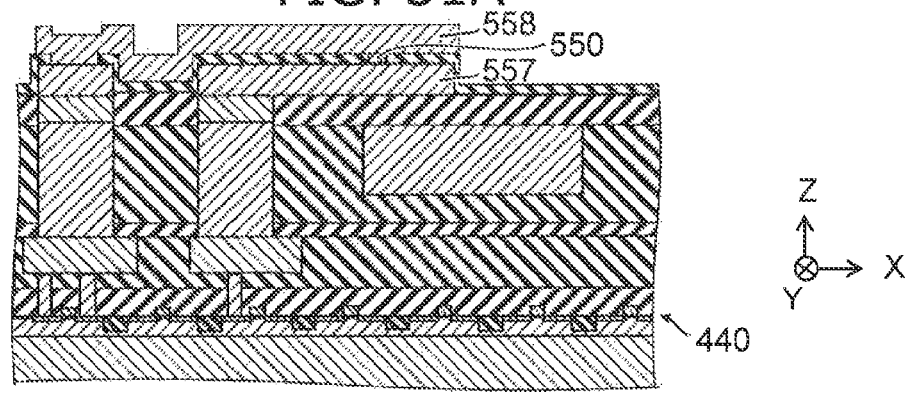

As shown in FIG. 31A and FIG. 31B, the conductive layer 562f is processed into a prescribed shape. Thereby, an interconnection 558 is formed. The interconnection 558 is electrically connected to the connection pillar 562fb.

Figure 32A:
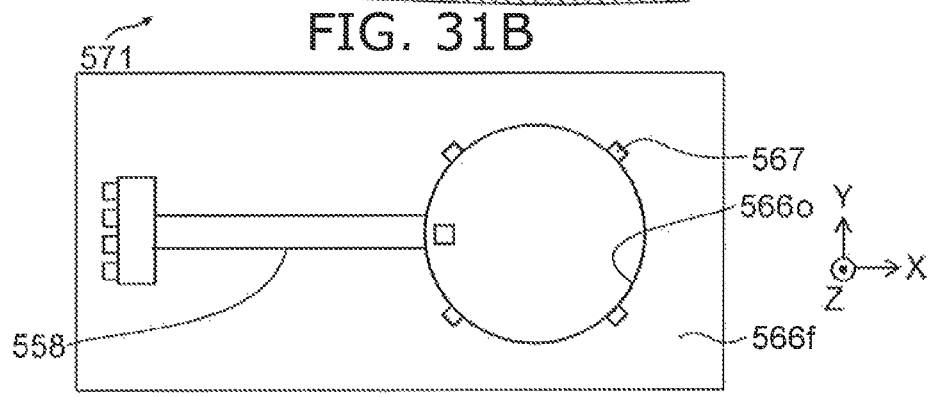
FIG. 32A and FIG. 32B, are schematic views showing a method for manufacturing a pressure sensor according to a third embodiment.
Figure 32B:
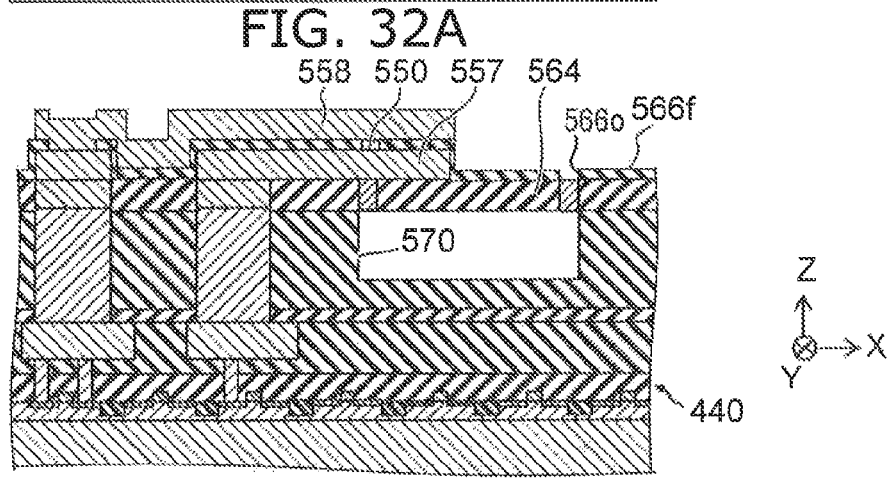

As shown in FIG. 32A and FIG. 32B, an opening 566o with a prescribed shape is formed in the insulating film 566f. The insulating film 561bf is processed via the opening 566o, and the sacrifice layer 514l is removed via the opening 566o. Thereby, a hollow portion 570 is formed. The removal of the sacrifice layer 514l can be performed using the wet etching method, for example.

When a fixing unit 567 is shaped like a ring, the space between the edge of the non-hollow portion above the hollow portion 570 and the film unit 564 is filled with an insulating film, for example.

Thus, a pressure sensor is formed.

Figure 33:
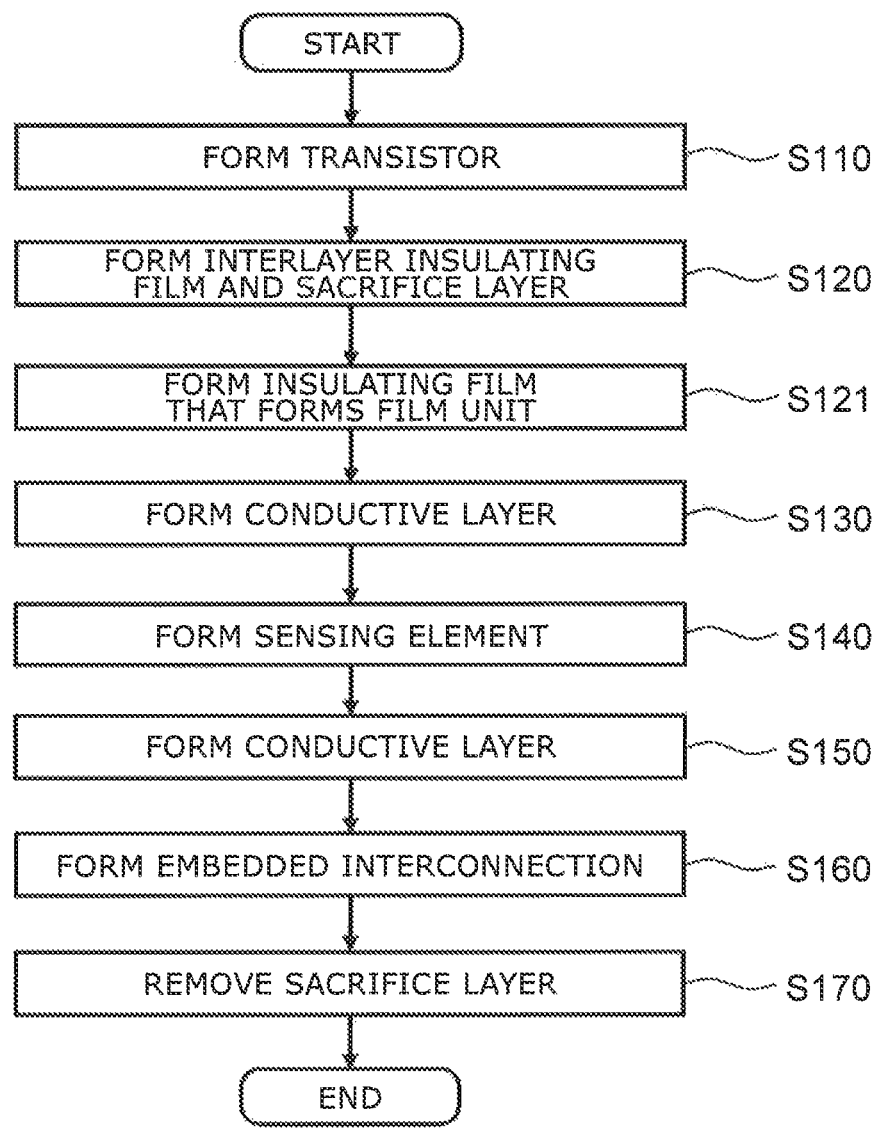
FIG. 33 is a flow chart showing a method for manufacturing a pressure sensor according to the third embodiment.

FIG. 33 is a flow chart illustrating a method for manufacturing a pressure sensor according to the third embodiment.

FIG. 33 relates to the method for manufacturing a pressure sensor described in regard to FIG. 21A to FIG. 32B, for example.

As shown in FIG. 33, the transistor 532 is formed on the semiconductor substrate 531, for example (step S110).

The transistor 532 is formed in the manner described in regard to FIG. 21A and FIG. 21B, for example.

Next, an interlayer insulating layer is formed on the semiconductor substrate 531, and the sacrifice layer 514l is formed on the transistor 532 (step S120).

The interlayer insulating layer, the sacrifice layer 514l, etc. are formed in the manner described in regard to FIG. 22A to FIG. 23B, for example. The interlayer insulating film 514i is included in the interlayer insulating layer, for example.

The insulating film 561bf that forms the film unit 564 is formed on the interlayer insulating layer (for example, the interlayer insulating film 514i) and the sacrifice layer 514l (step S121).

The conductive layer 561f below may serve also as the film unit 564 (70d). In this case, step S121 is omitted.

The conductive layer 561f that forms the interconnection 557 is formed (step S130).

The conductive layer 561f is formed in the manner described in regard to FIG. 25A and FIG. 25B, for example.

Next, a sensing unit 550 including magnetic layers is formed on the conductive layer 561f above the sacrifice layer 514l (step S140).

The sensing unit 550 is formed in the manner described in regard to FIG. 26A to FIG. 27B, for example.

Next, the conductive layer 562f that forms the interconnection 558 is formed on the sensing unit 550 (step S150).

The conductive layer 562f is formed in the manner described in regard to FIG. 30A to FIG. 31B, for example.

Next, an embedded interconnection is formed (step S160).

An interconnection that electrically connects the conductive layer 561f and the semiconductor substrate 531 and an interconnection that electrically connects the conductive layer 562f and the semiconductor substrate 531 are formed in the interlayer insulating layer, for example.

The embedded interconnection is formed in the manner described in regard to FIG. 21A, FIG. 21B, FIG. 22A, FIG. 22B, FIG. 24A, FIG. 24B, FIG. 27A, and FIG. 27B, for example.

Step S160 may be performed once or multiple times in a step at least one of between step S110 and step S150 and after step S150, for example.

Next, the sacrifice layer 514l is removed (step S170).

The sacrifice layer 514l is removed in the manner described in regard to FIG. 32A and FIG. 32B, for example.

Thus, a pressure sensor is completed.

Fourth Embodiment

The embodiment relates to a microphone using the pressure sensor of the embodiments described above.

Figure 34:
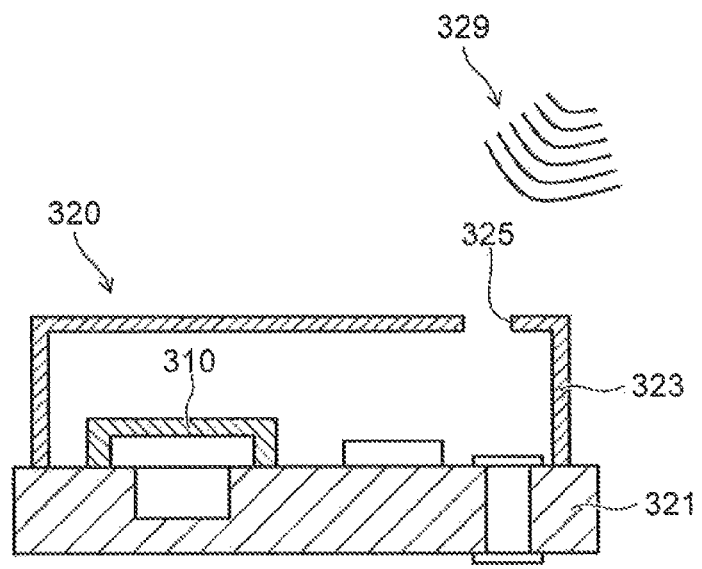
FIG. 34 is a schematic cross-sectional view showing a microphone according to a fourth embodiment.

FIG. 34 is a schematic cross-sectional view illustrating a microphone according to a fourth embodiment.

A microphone 320 according to the embodiment includes a printed circuit board 321, a cover 323, and a pressure sensor 310. The printed circuit board 321 includes a circuit of an amplifier etc., for example. An acoustic hole 325 is provided in the cover 323. Sound 329 passes through the acoustic hole 325 to enter the inside of the cover 323.

As the pressure sensor 310, any one of the pressure sensors described in regard to the embodiments described above and modifications thereof are used.

The microphone 320 reacts to sound pressure. By using a high-sensitivity pressure sensor 310, a high-sensitivity microphone 320 is obtained. The pressure sensor 310 is mounted on the printed circuit board 321, and an electric signal line is provided, for example. The cover 323 is provided on the printed circuit board 321 so as to cover the pressure sensor 310.

The embodiment can provide a high-sensitivity microphone.

Fifth Embodiment

The embodiment relates to a blood pressure sensor using the pressure sensor of the embodiments described above.

Figure 35A:
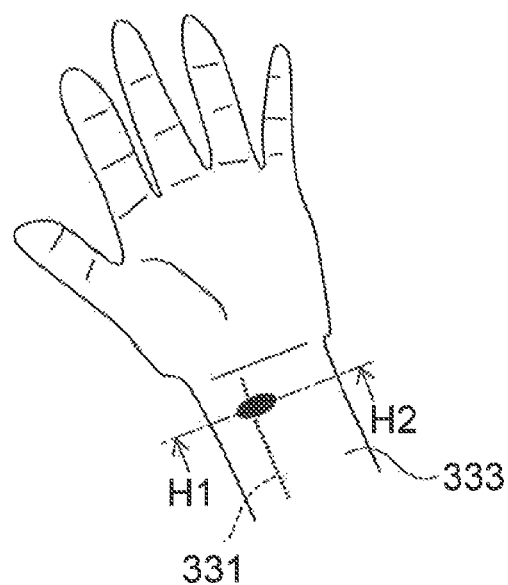
FIG. 35A and FIG. 35B are schematic views showing a blood pressure sensor according to an eighth embodiment.
Figure 35B:
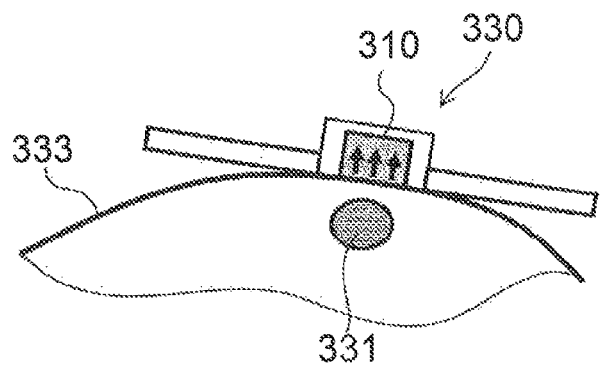

FIG. 35A and FIG. 35B are schematic views illustrating a blood pressure sensor according to an eighth embodiment.

FIG. 35A is a schematic plan view illustrating the skin on an artery of a person. FIG. 35B is a cross-sectional view taken along line H1-H2 of FIG. 35A.

In the embodiment, the pressure sensor 310 is used as a blood pressure sensor 330. Any one of the pressure sensors described in regard to the embodiments described above and modifications thereof are used as the pressure sensor 310.

Thus, high-sensitivity pressure sensing can be made by a small-sized pressure sensor. By pressing the pressure sensor 310 against the skin 333 on an artery 331, the blood pressure sensor 330 can make blood pressure measurement continuously.

The embodiment can provide a high-sensitivity blood pressure sensor.

Sixth Embodiment

The embodiment relates to a touch panel using the pressure sensor of the embodiments described above.

Figure 36:
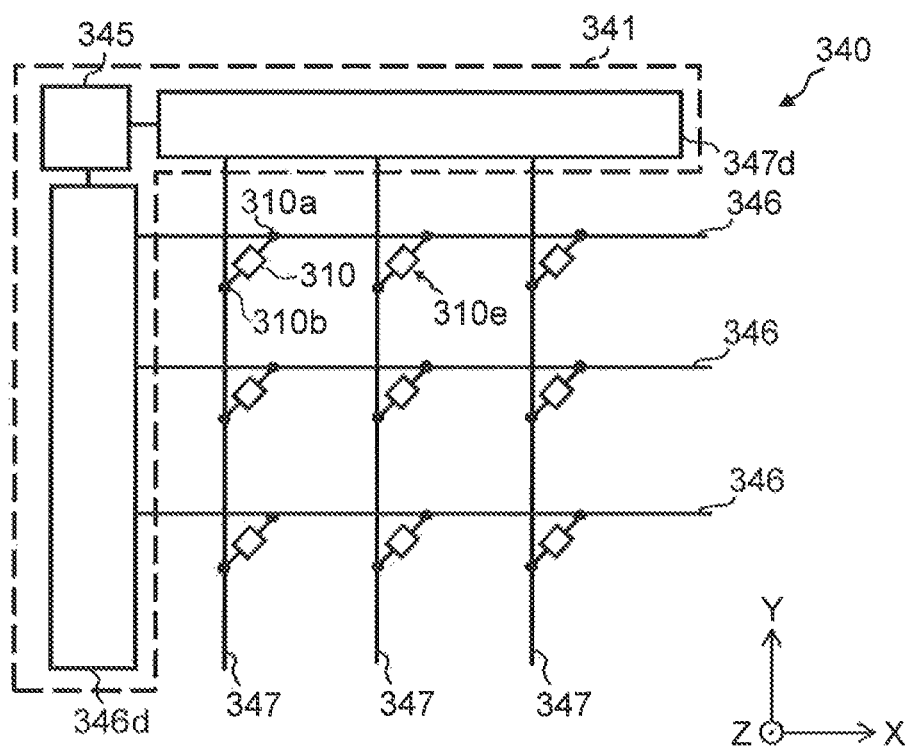
FIG. 36 is a schematic diagram showing a touch panel according to a sixth embodiment.

FIG. 36 is a schematic diagram illustrating a touch panel according to a sixth embodiment.

In the embodiment, the pressure sensor 310 is used as a touch panel 340. Any one of the pressure sensors described in regard to the embodiments described above and modifications thereof are used as the pressure sensor 310. In the touch panel 340, the pressure sensor 310 is mounted at least one of in a display and outside a display.

The touch panel 340 includes a plurality of first interconnections 346, a plurality of second interconnections 347, a plurality of pressure sensors 310, and a control unit 341, for example.

In this example, the plurality of first interconnections 346 are aligned along the Y-axis direction. Each of the plurality of first interconnections 346 extends along the X-axis direction. The plurality of second interconnections 347 are aligned along the X-axis direction. Each of the plurality of second interconnections 347 extends along the Y-axis direction.

Each of the plurality of pressure sensors 310 is provided in the intersection portion of each of the plurality of first interconnections 346 and each of the plurality of second interconnections 347. One pressure sensor 310 forms one sensing element 310e for sensing. Here, the intersection portion includes the position where the first interconnection 346 and the second interconnection 347 cross each other and a region around this.

One end 310a of each of the plurality of pressure sensors 310 is connected to each of the plurality of first interconnections 346. The other end 310b of each of the plurality of pressure sensors 310 is connected to each of the plurality of second interconnections 347.

The control unit 341 is connected to the plurality of first interconnections 346 and the plurality of second interconnections 347.

The control unit 341 includes a circuit for the first interconnection 346d connected to the plurality of first interconnections 346, a circuit for the second interconnection 347d connected to the plurality of second interconnections 347, and a control circuit 345 connected to the circuit for the first interconnection 346d and the circuit for the second interconnection 347d, for example.

The pressure sensor 310 can make high-sensitivity pressure sensing with a small size. Thus, a high-definition touch panel can be provided.

The pressure sensors according to the embodiments described above can be used for various pressure sensor devices such as atmospheric pressure sensors and air pressure sensors for tires, as well as the uses mentioned above.

The embodiment can provide a strain sensing element, a pressure sensor, a microphone, a blood pressure sensor, and a touch panel of high sensitivity.

In the specification of this application, "perpendicular" and "parallel" refer to not only strictly perpendicular and strictly parallel but also include, for example, the variation due to manufacturing processes, etc. It is sufficient to be substantially perpendicular and substantially parallel.

Hereinabove, embodiments of the invention are described with reference to specific examples. However, the invention is not limited to these specific examples. For example, one skilled in the art may appropriately select specific configurations of components of strain sensing elements, pressure sensors, microphones, blood pressure sensors, and touch panels such as supports, film units, sensing units, sensing elements, magnetic layers, magnetic films, and spacer layers from known art and similarly practice the invention. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all strain sensing elements, pressure sensors, microphones, blood pressure sensors, and touch panels practicable by an appropriate design modification by one skilled in the art based on the strain sensing elements, pressure sensors, microphones, blood pressure sensors, and touch panels described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A strain sensing element comprising:
a film unit having a film surface and being deformable; and
a sensing unit including a first sensing element and a second sensing element,
the first sensing element being provided between a part of the film unit and the second sensing element,
the first sensing element including a first magnetic layer, a second magnetic layer provided apart from the first magnetic layer in a first direction crossing the film surface, and a first spacer layer provided between the first magnetic layer and the second magnetic layer, a magnetization of the first magnetic layer being configured to change in accordance with a deformation of the film unit,
the second sensing element including a third magnetic layer, a fourth magnetic layer provided apart from the third magnetic layer in the first direction, and a second spacer layer provided between the third magnetic layer and the fourth magnetic layer, a magnetization of the third magnetic layer being configured to change in accordance with the deformation of the film unit,
wherein
a magnetization of the second magnetic layer and a magnetization of the fourth magnetic layer are fixed,
the fourth magnetic layer is disposed between the third magnetic layer and the film unit, and
the second magnetic layer is disposed between the first magnetic layer and the film unit.

2. The element according to claim 1, further comprising:
a first electrode; and
a second electrode,
the sensing unit being provided between the first electrode and the second electrode,
a current flowing between the first electrode and the second electrode being configured to flow between the first magnetic layer and the second magnetic layer, and
the current being configured to flow between the third magnetic layer and the fourth magnetic layer.

3. A pressure sensor comprising:
the strain sensing element according to claim 1; and
a support supporting the film unit.

4. A strain sensing element comprising:
a film unit having a film surface and being deformable; and
a sensing unit including a first sensing element and a second sensing element,
the first sensing element being provided between a part of the film unit and the second sensing element,
the first sensing element including a first magnetic layer, a second magnetic layer provided apart from the first magnetic layer in a first direction crossing the film surface, and a first spacer layer provided between the first magnetic layer and the second magnetic layer, a magnetization of the first magnetic layer being configured to change in accordance with a deformation of the film unit,
the second sensing element including a third magnetic layer, a fourth magnetic layer provided apart from the third magnetic layer in the first direction, and a second spacer layer provided between the third magnetic layer and the fourth magnetic layer, a magnetization of the third magnetic layer being configured to change in accordance with the deformation of the film unit,
wherein
a magnetization of the second magnetic layer and a magnetization of the fourth magnetic layer are fixed,
the third magnetic layer is disposed between the fourth magnetic layer and the film unit, and
the first magnetic layer is disposed between the second magnetic layer and the film unit.

5. A microphone comprising the pressure sensor according to claim 3.

6. A strain sensing element comprising:
a film unit having a film surface and being deformable; and
a sensing unit including a first sensing element and a second sensing element,
the first sensing element being provided between a part of the film unit and the second sensing element,
the first sensing element including a first magnetic layer, a second magnetic layer provided apart from the first magnetic layer in a first direction crossing the film surface, and a first spacer layer provided between the first magnetic layer and the second magnetic layer, a magnetization of the first magnetic layer being configured to change in accordance with a deformation of the film unit,
the second sensing element including a third magnetic layer, a fourth magnetic layer provided apart from the third magnetic layer in the first direction, and a second spacer layer provided between the third magnetic layer and the fourth magnetic layer, a magnetization of the third magnetic layer being configured to change in accordance with the deformation of the film unit,
wherein
a magnetization of the second magnetic layer and a magnetization of the fourth magnetic layer are fixed,
the fourth magnetic layer is disposed between the third magnetic layer and the film unit, and
the first magnetic layer is disposed between the second magnetic layer and the film unit.

7. The element according to claim 1, wherein
the third magnetic layer is disposed between the fourth magnetic layer and the film unit, and
the second magnetic layer is disposed between the first magnetic layer and the film unit.

8. The element according to claim 1, wherein a distance between the first magnetic layer and the third magnetic layer is not more than 1/5 of a thickness along the first direction of the film unit.

9. The element according to claim 1, wherein the sensing unit further includes a first hard bias layer arranged with the first sensing element in a second direction crossing the first direction.

10. The element according to claim 1, wherein the sensing unit further includes a first shield layer arranged with the first sensing element in a second direction crossing the first direction.

11. The element according to claim 1, wherein the sensing unit further includes a second shield layer provided between the first sensing element and the second sensing element.

12. The element according to claim 1, wherein the sensing unit further includes an interposition layer provided between the first sensing element and the second sensing element.

13. The element according to claim 1, wherein
the sensing unit is provided in a plurality,
the plurality of sensing units are provided on the film unit, and
the sensing units are apart from each other in a direction crossing the first direction.

14. The element according to claim 13, wherein the sensing units are electrically connected in series.

15. The element according to claim 13, wherein the sensing units are electrically connected in parallel.

16. The element according to claim 13, wherein
the sensing units are electrically connected to one another and
a number of the sensing units electrically connected is not less than 7 and not more than 200.

17. A blood pressure sensor comprising the pressure sensor according to claim 3.

18. A touch panel comprising the pressure sensor according to claim 3.

* * * * *